(12) United States Patent
Kerek

(10) Patent No.: US 9,688,856 B2
(45) Date of Patent: Jun. 27, 2017

(54) BIOLOGICALLY ACTIVE SILICIC ACID

(75) Inventor: Franz Kerek, Munich (DE)

(73) Assignee: Sinatur GmbH, Munich (DE)

( * ) Notice: Subject to any disclaimer, the term of this patent is extended or adjusted under 35 U.S.C. 154(b) by 484 days.

(21) Appl. No.: 13/057,128

(22) PCT Filed: Jul. 31, 2009

(86) PCT No.: PCT/EP2009/005717
§ 371 (c)(1),
(2), (4) Date: Jun. 3, 2011

(87) PCT Pub. No.: WO2010/012507
PCT Pub. Date: Feb. 4, 2010

(65) Prior Publication Data
US 2011/0229577 A1    Sep. 22, 2011

Related U.S. Application Data

(60) Provisional application No. 61/136,016, filed on Aug. 6, 2008.

(30) Foreign Application Priority Data

Aug. 1, 2008   (EP) .................................... 08075683

(51) Int. Cl.
| | | |
|---|---|---|
| A61K 9/14 | (2006.01) |
| A61K 33/00 | (2006.01) |
| C08G 77/00 | (2006.01) |
| C08L 83/02 | (2006.01) |
| B82Y 5/00 | (2011.01) |
| C08G 77/02 | (2006.01) |

(52) U.S. Cl.
CPC ................ C08L 83/02 (2013.01); A61K 9/14 (2013.01); A61K 33/00 (2013.01); B82Y 5/00 (2013.01); C08G 77/02 (2013.01)

(58) Field of Classification Search
None
See application file for complete search history.

(56) References Cited

U.S. PATENT DOCUMENTS

| 5,534,509 | A | 7/1996 | Konishi |
| 7,915,198 | B2 | 3/2011 | Kros |
| 2004/0248995 | A1 * | 12/2004 | Glaubitt ................. B82Y 30/00 516/34 |
| 2004/0258929 | A1 * | 12/2004 | Glaubitt ................. C03C 17/007 428/446 |
| 2005/0002970 | A1 * | 1/2005 | Ketelson et al. ............. 424/400 |
| 2007/0098807 | A1 | 5/2007 | Babich et al. |

FOREIGN PATENT DOCUMENTS

| DE | 10146687 C1 * | 6/2003 | ........... C03C 17/007 |
| EP | WO9901377 A1 * | 1/1999 | |

OTHER PUBLICATIONS

Geddes, C.D., et al., "1- and 2-Photon Fluorescence Anisotropy Decay in Silicon Alkoxide Sol-Gels: Interpretation in Terms of Self-assembled Nanoparticles", 2002, J. Phys. Chem. B, pp. 3835-3841.*
Lopez, P.J., et al., "Mimicking Biogenic Silica Nanostructures Formation", 2005, Current Nanoscience, pp. 73-83.*
Schwarz, J.A., et al., "Surfaces of Nanoparticles and Porous Materials", 2002, Marcel Dekker Inc., pp. 138-139.*
International Search Report for PCT Application No. PCT/EP2009/005717 issued Oct. 12, 2009.
Written Opinion for PCT Application No. PCT/EP2009/005717 issued Oct. 12, 2009.
International Preliminary Report on Patentability for PCT/EP2009/005717 issued Feb. 1, 2011.
Iler, Chapter 3—"Polymerization of Silica" 1979.
Khamova et al. "Investigation of the Structuring in the Sol-Gel Systems Based on Tetraethoxysilane" Glass Physics Chemistry 2006 vol. 32(4), 448-459.

* cited by examiner

*Primary Examiner* — Michael G Hartley
*Assistant Examiner* — Lance Rider
(74) *Attorney, Agent, or Firm* — Dinsmore & Shohl LLP

(57) ABSTRACT

The present invention relates to low-molar mass condensed derivatives of silicic acid of sub-nano particle size characterized by particular structure and specific biological activities. Preparation methods and applications are presented for the here disclosed sub-nano silicic acid (SNSA) which interact with bio-molecules and modify significantly their structure and biological function. Preferred field of application of the inventive silicic acid derivatives is to modulate the structure and biological function of proteins particularly of those involved in reversible phosphorylation within biological signal transduction or membrane transport processes. Structure of the substances, methods for the preparation and stabilization, as well as pharmaceutical compositions comprising the substances and methods of application in the prevention, diagnosis and therapy of diseases are disclosed.

14 Claims, 33 Drawing Sheets

Speroidal sub-nano silicic acid 1.45 nm diameter

Figure 9

Intra-molecular interaction of SNSA with proteins

Protein structure modified by Interaction of SNSA

Figure 11:
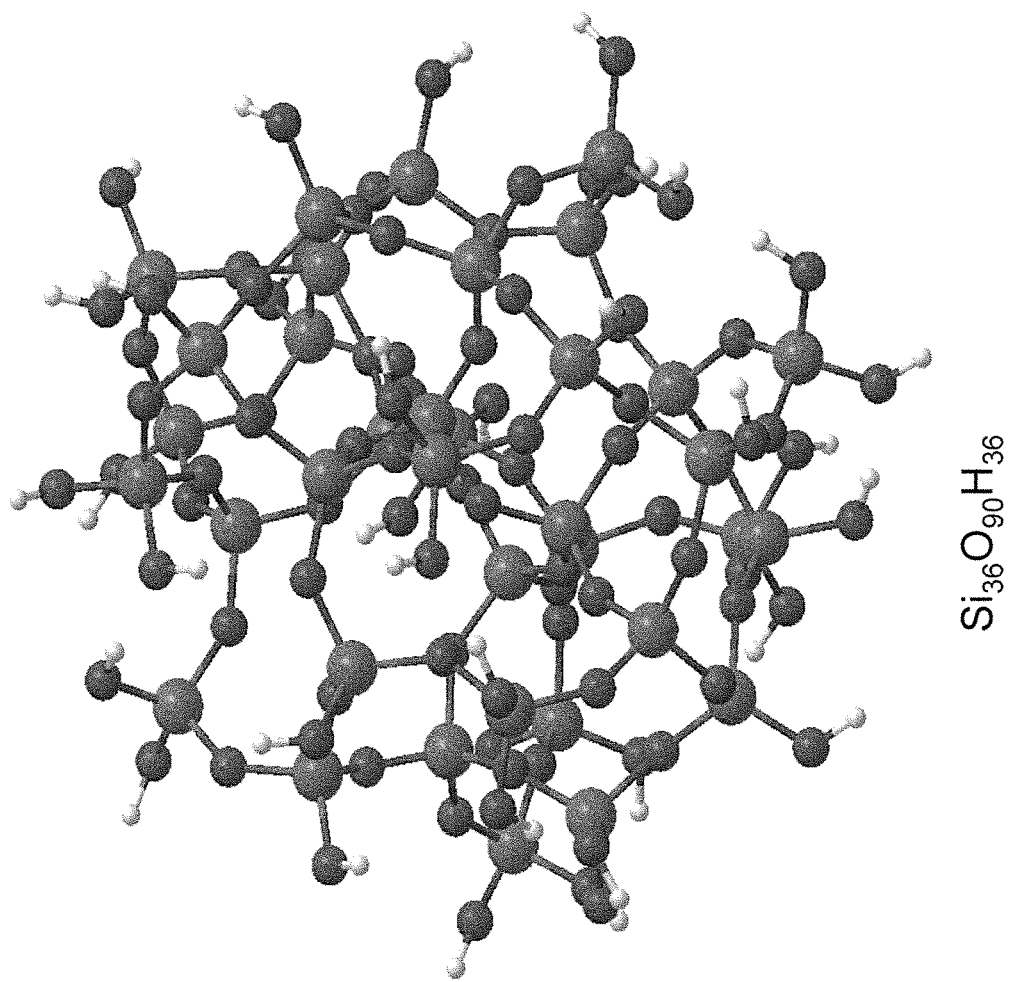

Figure 11     $Si_{36}O_{90}H_{36}$ $Si_{46}O_{115}H_{46}$ $Si_{42}O_{100}H_{32}$ Figure 33
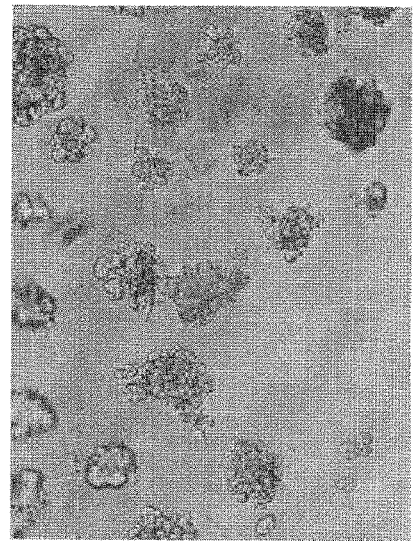
SNSA 2 µg/ml weak inhibition
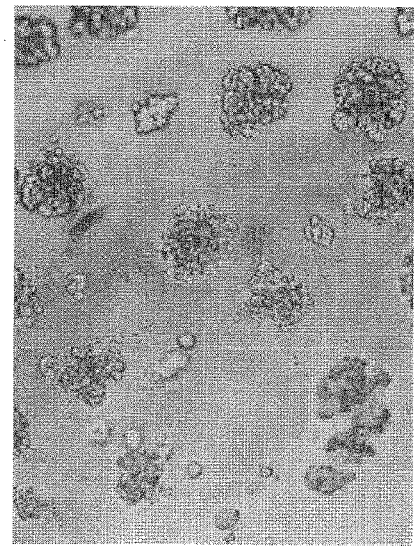
SNSA 10µg/ml inhibits efficiently the branching of breast cancer cells 435S
CONTROL: Branching of breast cancer cells 435S
CONCLUSION:
-SNSA inhibits at > 3µg/ml branching of breast cancer cells 435S

BIOLOGICALLY ACTIVE SILICIC ACID

REFERENCE TO RELATED APPLICATION

This application is a U.S. National Stage of PCT/EP2009/005717, filed Jul. 31, 2009, which claims priority to U.S. Provisional Patent Application Ser. No. 61/136,016, filed Aug. 6, 2008 and EP 08075683.6, filed Aug. 1, 2008. The entire content of each application is incorporated herein by reference.

1 FIELD OF THE INVENTION

The present invention relates to low-molar mass condensed derivatives of silicic acid characterised by particular structure and remarkable biological activities. Applications of the here disclosed silicic acid that interact with biomolecules and modify significantly their structure and biological function are disclosed. The preferred field of application of the inventive silicic acid is to modulate the structure and biological function of proteins, particularly of those involved in reversible phosphorylation within biological signal transduction or membrane transport processes. The structure of the substance, methods of preparation and stabilization, pharmaceutical compositions comprising the substance and methods of application in the prevention, diagnosis and therapy of diseases are disclosed.

2 BACKGROUND OF THE INVENTION

Protein phosphorylation is a decisively important biochemical step within biological processes like: signal-transduction, membrane transport or muscle contraction. The phosphorylation is accomplished by chemical binding of a phosphate moiety to a hydroxy-amino-acid (like tyrosine or serine) of the protein chain. Phosphorylation modifies the structure and biological activity of a protein, usually in a reversible manner since the decoupling of the phosphate moiety reforms the original structure.

Specific promoters of protein phosphorylation are the protein-kinases (PK) which transfer a phosphate group from adenosine-triphosphate (ATP) to the protein substrate. Protein-phosphatases (PP) act in the contrary by splitting off the protein-bonded phosphate group. These converse functions of protein-kinases and phosphatases balances and regulates several complex cellular processes such as signal-transduction and membrane-transport.

Dysfunction of certain protein-phosphorylation processes and of the connected signalling cascades have been identified as crucial factors in several diseases. Purposeful modulation of reversible phosphorylation processes is considered therefore a promising approach to find novel therapeutics for diseases like cancer.

This concept is confirmed by recent achievements in tumour therapy with monoclonal antibodies which block the tumour-growth-promoting protein-kinases HER-2 and HER-3 in breast cancer. This tumour-suppressive action of the antibody protein is however limited in time while the host organism identifies it as antigenic protein and generates anti-antibodies to neutralize it. Providing non-antigenic drug substances for the targeted suppression or modulation of certain protein kinases/phosphatases remains an unmet medical need.

Members of the P-type ATPase (adenosine-triphosphatase) super-family are structurally related proteins involved in transport across biological membranes using energy resulting from the hydrolysis of adenosine triphosphate (ATP). According to their function as trans-membrane "ion transporters" these ATPases are classified as membrane "ion pumps". Actually, each pumping cycle involves a phosphorylation and subsequent de-phosphorylation of the ATPase protein.

Several diseases are connected with the defective function of a certain ATPase pump, which suggests to explore the therapeutic potential of drug substances inhibiting or modulating this enzyme. Despite considerable progress in structural elucidation of ATPases, their mechanism of action and their modulation by drug substances is not fully elucidated.

One typical P-type ATPase is the Na,K-ATPase or sodium pump, which controls ionic homeostasis as well as a broad spectrum of cellular functions such as: membrane potential, pH, temperature or water osmosis. The sodium pump is involved in the regulation of important physiological processes like: muscle contraction, nervous signal transmission, renal sodium retention or vascular tone. Severe dysfunctions of the sodium pump are decisively involved in several pathologies like: essential hypertension or cardiac failure.

Prior art inhibitors of the Na,K-ATPase are the cardiac steroids of herbal origin applied since a long time for the treatment of cardiac insufficiency. However their high toxicity with lethal dose $LD_{50}$ in the domain of 0.1-0.25 mg/kg body mass in human, narrows considerably their therapeutic dose range. Thus, for the cardiotonic steroid Digoxin the daily administration of 4-5 mg/patient is well tolerated but, 8-10 mg/patient/day may cause fatal toxicity. Finding of non-toxic sodium pump inhibitors is of major therapeutic interest in the treatment of cardiac insufficiency, essential hypertension and related diseases.

Candidate non-toxic modulators of the sodium pump could be the putative endogenous digitalis-like factors (EDLFs). Their existence is supported by a consistent body of experimental data but the structure of EDLFs was up to now not disclosed. Recent data demonstrated convincingly the role of Na,K-ATPase as a signalling transducer at the level of cell membranes, which suggest a novel field of potential therapeutic applications of the sodium pump modulating agents (Xie, Z., Askhari, A.; Eur. J. Biochem. 2002, 269, 2434-2439).

$H^+$/K-ATPase or proton pump is another member of the ATPase family which transports a hydrogen ion ($H^+$) from the cytoplasm in exchange for one potassium ion ($K^+$) retrieved from the gastric lumen. Proton pump inhibitors (PPI) that directly bind to and inactivate the $H^+/K^+$ ATPase are disclosed in the prior art as therapeutics to treat gastric hyperacidity e.g.: omeprazole, esomeprazole, lansoprazole, pantoprazole and rabeprazole (U.S. Pat. No. 5,232,706). However, chronic administration of these PPI drugs produces side effects like: constipation, cough, dizziness or back pain. Increased susceptibility to bacterial infection due to the enhanced pH value (>4) is a further side effect caused by chronic use of synthetic proton pump inhibitory drugs.

Calcium homeostasis inside eukaryotic cells is maintained by ubiquitously distributed Ca-ATPase enzymes known as Ca pumps. Plasma membrane Ca-ATPase generally counteracts the influx of free $Ca^{2+}$ ions through calcium channels and thus exerts an essential role in controlling enzymatic reactions and a broad spectrum of intracellular signalling processes. In muscle cells, the Ca-ATPase pumps back $Ca^{2+}$ ions into the sarcoplasmic reticulum SR which stores Ca during muscle relaxation. This data strongly suggests that Ca-pump-modulating substances could have therapeutic applications e.g. in muscle contraction pathologies, but prior art inhibitors like thapsigargin are of limited applicability due to their advanced cellular toxicity.

Several vanadium compounds were identified as prior art inhibitors of the Na,K-ATPase, H/K-ATPase, Ca-ATPase and of other P-type ATPase enzymes. Most frequently applied are: meta-vanadate $(VO_3)_n^-$ or decavanadates $[V_{10}O_{28}]^{6-}$ which inhibit ATPases with $IC_{50}$ (half-inhibitory concentration) values in the micro- and sub-micro-molar range but the results are not reproducible due to instant structural modification of vanadates. Decavanadate, considered the V oligomer of biochemical relevance is not stable at physiologic pH but, once formed, its disintegration is slow enough to allow the study of its effects. Despite their questionable structures, vanadates or their peroxidated derivatives the "pervanadates" have extended laboratory applications due to their very efficient inhibition of protein phosphatases which is of primary importance in investigating the complementary kinases.

Vanadate ions mimic surprisingly the rapid actions of insulin in various cell types. When administered orally to hyperglycaemic rats, vanadate stimulates glucose uptake and metabolism, and leads to normo-glycemic states. In addition, vanadate restores tissue responsiveness to insulin and hepatic glycogen levels as well as activates new synthesis of key enzymes for carbohydrate metabolism. Clinical benefits of vanadium compounds in the therapy of diabetes have been confirmed but only by short time administration in human.

Despite this emerging interest for the insulin-mimetic use of the vanadium compounds in diabetes, the toxicology of vanadium derivatives causes concern. Gastrointestinal disturbances were reported as a common toxic effect in humans and animal experiments with higher doses revealed severe signs of renal and hepatic toxicity. Long-term use of vanadium is a major concern due its progressive tissue accumulation mostly in kidney, spleen, testes, liver and bone and the production of toxic effects. The toxicity depends on the oxidation state and coordination geometry of vanadium in the order: pervanadate>vanadates>vanadyl as well as on the mode of administration [Domingo, J. L.: Vanadium and Diabetes. What about vanadium toxicity?" *Mol. Cell. Biochemistry* 2000, 203, 185-187].

The ABC (ATP binding-cassette) transporter proteins form an important class of membrane proteins associated with multiple cellular functions, including the elimination of xenobiotics. Although these ATP-driven efflux pumps are essential in the homeostasis of normal cells, their activity is less desired for instance by the chemo-therapy of cancer patients. This is because a survival strategy of cancer cells is to over-express ABC type multidrug-efflux pumps (MDR) making the tumours resistant to cancer drugs. Applying the cytostatic drug in greater extent is only a transient solution since it will intensify dramatically the toxic side effects. Selective inhibition of certain ATPase driven multi drug efflux pumps could provide important benefits in the cancer therapy but prior art MDR inhibitors are less efficient.

Object of the present invention is to provide new pharmaceutically active substances which are useful for prophylaxis, diagnosis and treatment of various diseases such as hypertension, diabetes, bone diseases, cardiovascular diseases, neurodegenerative pathologies and diseases, cancer, hyperacidity, osteoporosis, dental calculus, Alzheimer disease, Creutzfeld-Jakob disease and wound healing.

This object is solved by the teaching of the independent claims. Preferred embodiments are disclosed in the description, the dependent claims, the figures and the examples.

3 DESCRIPTION OF SILICIC ACID

Silica, the combination of silicon with oxygen is by far the most abundant component of the earth's crust. In its broad connotation the word "silica" includes silicon dioxide in all its chemically combined forms in which the silicon atom is surrounded by oxygen atoms. Silicon dioxide $SiO_2$, commonly found as crystalline quartz is actually the anhydride of the ortho-silicic acid with the formula $Si(OH)_4$. Despite the ubiquitous presence of ortho-silicic acid in the living world actually not a single biological molecule has been identified which contains silicon or needs this element.

Ortho-silicic acid is prepared by treatment of alkali silicates with cation-exchanger resin or by hydrolysis of tetra-alkyl-ortho-silicates such as tetra-ethyl-ortho-silicate (TEOS). Freshly prepared solutions of silicic acid are very unstable while rapidly polymerised forming colloid particles, amorphous gel and finally a porous or dense solid material. By the successive elimination of water between silicic acid and its homologue derivatives a multitude of linear, branched, cyclic and multi-cyclic condensation products are formed as exemplified in FIG. 1. The low molar mass n≤20 condensation products are classified as oligomers where n notes the number of condensed SiOx units. These simple oligomeric condensation products of ortho-silicic acid are described by classical chemical formula but their individual isolation is a very difficult issue.

Figure 1:
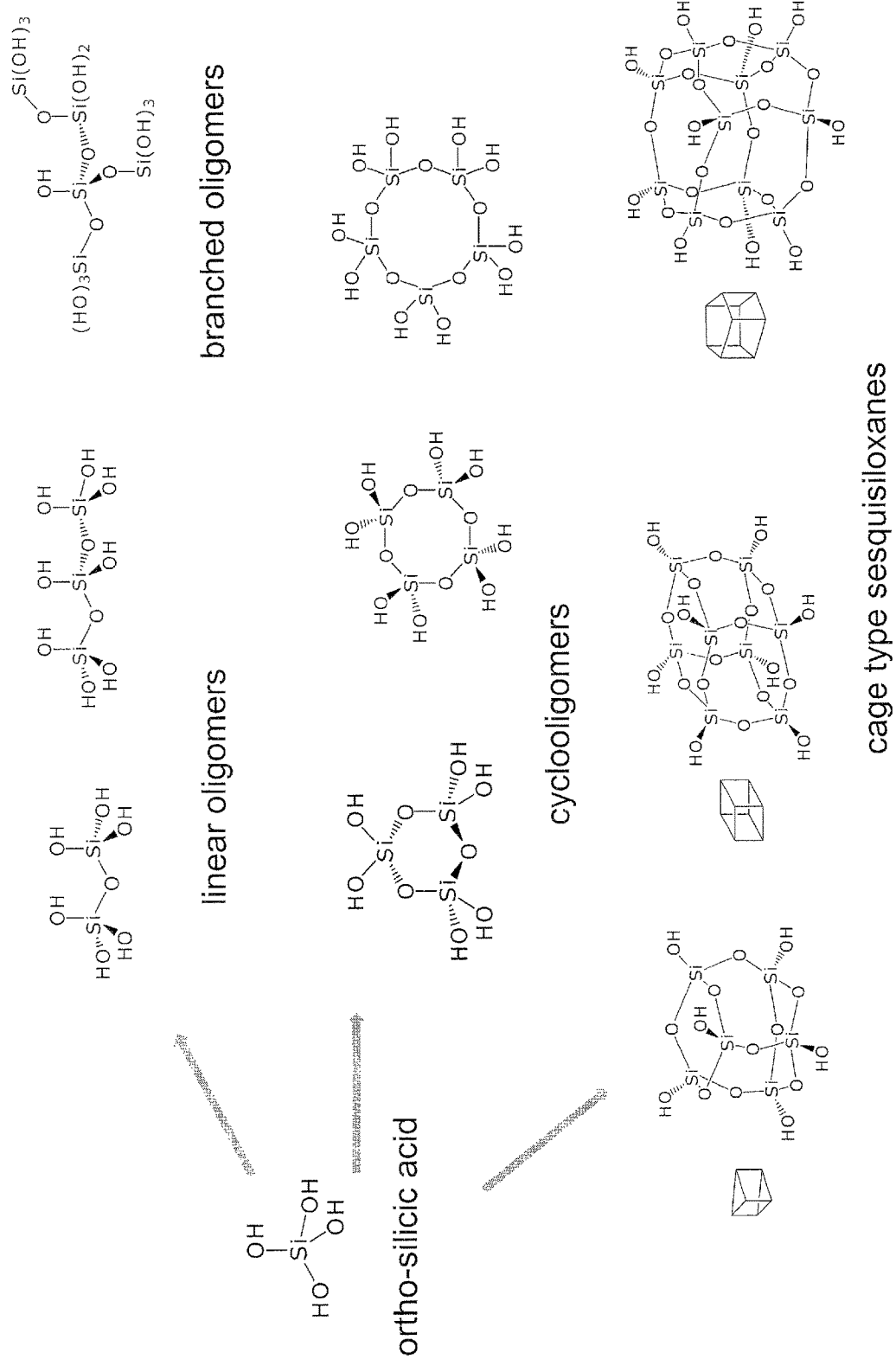

General formula of these condensation products is $[SiO_x(OH)_{4-2x}]_n$ where "n" stands for the number of the condensed $SiO_x(OH)_{4-2x}$ units and x has values between 1-2. Thus, x=1 in the formula of simple cyclo-silica derivatives like the cyclo-trisilicic: $[Si_3O_3(OH)_6]$ with n=3, cyclo-tetrasilicic $[Si_4O_4(OH)_8]$ with n=4 or cyclo-pentasilicic acid $[Si_5O_5(OH)_{10}]$ with n=5. Structure of individual species is assigned by $^{29}Si$ NMR spectra and by transformation in stable derivatives. FIG. 1 gives an overview of the prior art small molar mass condensed silicic acid species including multiple condensed silicate cages like prismatic hexamer $[Si_6O_9(OH)_6]$, cubic octamer $[Si_8O_{12}(OH)_8]$ or prismatic decamer $[Si_{10}O_{20}(OH)_{10}]$ with x=1.5.

Figure 2:
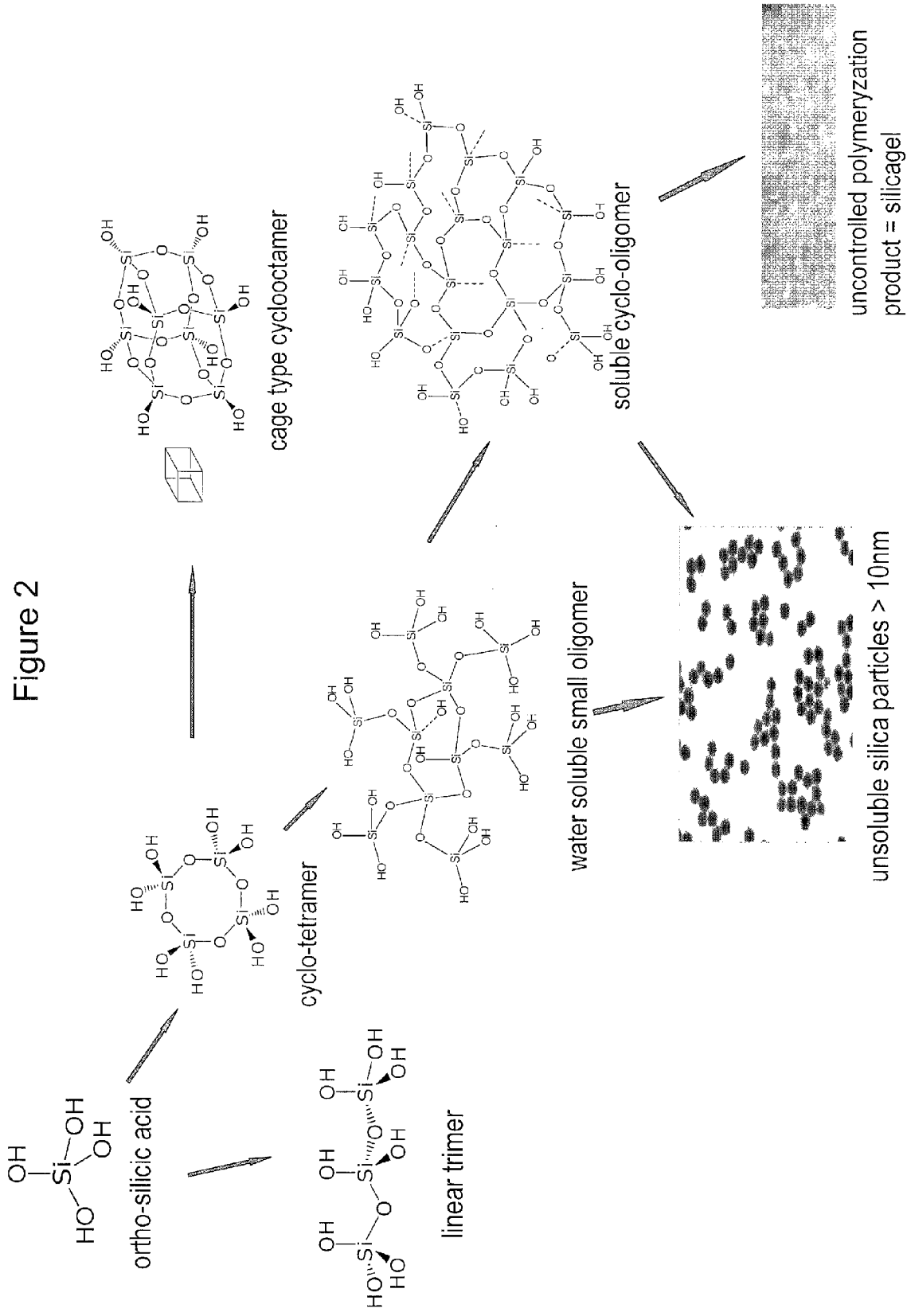

The next advanced (n>10) condensation products of the silicic acid, are considered generally as very unstable because they enter instantaneously further polymerisations with building of silica particles and amorphous gel (FIG. 2). The intermediate formation of higher oligomeric or low polymeric silica species of sub-particle size was assumed but less intensively investigated in detail. Actually the multiple condensation products are forming some equilibrium mixtures with distribution dependent on concentration, temperature and pH. Owing to their marked instability and the less controllable composition these sub-colloidal ($\phi$<5 nm) polymerised silicic acid species were considered to have only limited practical importance.

Further advanced polymerization products of silicic acid derivatives with n>2,000 are the nano-particles with diameter $\phi$>5 nm. They are described as solid nano- or microparticles and characterised by specific physicochemical properties. In watery medium silica nano-particles form colloidal suspensions with extended technical utilizations [U.S. Pat. No. 3,702,866; U.S. Pat. No. 3,707,979; U.S. Pat. No. 4,061,724]. Similarly broad technical applications have the solid silica particles with narrowly controlled internal cavities such as the zeolites.

Silica nano-particles with $\phi$>10 nm are currently being evaluated as inert solid carrier beads to which proteins may be attached. This physical adsorption or even chemical bonding of the protein to the large silica nano-particle can provide remarkable effects by interactions with immune cells and effectors. The ordered bonding of several antigenic proteins to the surface of a large silica particle can enhance dramatically the immune response elicited by the antigen

[Tan, W. et al "Bionanotechnology Based on Silica Nanoparticles" Medicinal Research Review 2004, 24, 621-638].

However, this prior art bonding of proteins to large silica nano-particles can also initiate by heterogenous nucleation the unwanted aggregation of the proteins. Assembly processes and structural changes by the aggregation cause the loss of the biological properties of the proteins. Uncontrolled aggregation of proteins is a major concern in several pathologies like the formation of the amyloid-plaque in Alzheimer disease and should be avoided.

A group of patents by Nippon Zoki [U.S. Pat. Nos. 5,534,509; 5,685,896 and 5,807,951] claim a biological regulating function for polymeric silica with preferred molar weight in the range of between 20,000-1,000,000 g/mol (Da), equivalent to degree of polymerization (DP) in the range of between 490-16,500. However, in this preferred molecular weight range of the cited invention, the disclosed compounds must be almost colloidal silica particles or even insoluble gels. It is in serious doubt that such large-dimension colloidal particles and insoluble gels can provide the claimed bio-regulatory activities. Significantly, in the 15 years from the first filing, neither scientific reports nor practical applications have confirmed the biological activities claimed for these silica polymers.

4 SUMMARY OF THE INVENTION

The present invention relates to particularly structured biological active silicic acids with dimensions below that of nano-sized silica particles, classified accordingly as sub-nano silicic acids (SNSA). This classification reflects their dimension $\phi$ and degree of polymerization n in the general formula I, which is below that of the nano-sized silica particles with diameter $\phi > 5$ nm and n>2,000.

General formula (I) of the silicic acids SNSA of the invention is:

$$[SiO_x(OH)_{4-2x}]_n \quad \text{(I)}$$

wherein
the Si atoms are $Q^1$, $Q^2$, $Q^3$ and $Q^4$ type Si atoms and
n represents an integer between 12 and 2000 and
x represents a number between 1.2 and 1.8 and
wherein the substance consists of an inner core and an outer shell and
wherein more than 75% of the $Q^4$ type Si atoms are contained in the inner core and more than 75% of $Q^3$ and $Q^2$ and $Q^1$ type Si atoms are contained in the outer shell.

Structurally the inventive substance is described as condensed silicic acid molecules with molecular diameter ($\phi$) in the range of $0.3 < \phi < 5$ nm, preferably $0.6 < \phi < 3$ nm. The number "n" of the condensed silica ($SiO_x$) units or more precisely described as $[SiO_x(OH)_{4-2x}]_n$ units of the inventive biological active silicic, acids is in the range of $12 < n < 2000$, preferably $20 < n < 300$. Accordingly the biologically active sub-nano silicic acids of the invention have a molecular mass in the range of 0.7-140 kg/mol (kD), preferably in the range of 1.4-20 kg/mol (kDa).

An essential structural feature of the inventive substance is the spheroidal or almost spheroidal shape of the molecule with densely and evenly distributed free Si—OH bonds disposed on the "outer shell" of the molecule. The unusually high number of free Si—OH (silanol) groups on the outer shell of the inventive molecules provides their high solubility (>5% m/m) in water and which also justifies their classification as silicic "acid" due to their significantly higher acidity in comparison with that of the orthosilicic acid. According to the current invention this almost spheroidal structure with high number of free Si—OH (silanol) groups on the outer shell is optimally accomplished by a surprisingly narrow range of the number "n" of the condensed $(SiOx)_n$ units. Optimal range for the stability of the almost spheroidal form with highest surface density of the silanol bonds is accomplished at discrete values of number "n" of condensed $[SiO_x(OH)_{4-2x}]_n$ units in the range of 12 to 2,000, preferably in the range of 16 to 1000, 19 to 400 and most preferably with a maximum stability range in the 28 to 128 range of n values.

Furthermore, the invention discloses methods for the preparation of the bioactive silicic acids of formula (I) preferably by synthesis from large scale accessible precursors as well as for the stabilization and chemical derivatization of the biologically active inventive substance.

The substance of the invention is able to modify the structure and activity of proteins preferably of that involved in reversible phosphorylation within signal transduction and membrane transport processes. The fields of application for the inventive silicic acids are the therapy of diseases caused by or connected to the defective function of reversible phosphorylation in certain signalling proteins and transport ATPases or ATP driven efflux pumps. The inventive substance provides substantial technical progress in comparison with prior art agents like vanadates used to modulate protein phosphorylation or to inhibit P-type ATPases as well as cardiac steroids which inhibit Na,K-ATPase in human. Although similar in their activity the inventive silica substance provides a decisive advantage for medicinal applications in comparison with toxic, prior art vanadates or cardiac steroids.

The inventive compound interacts with ATPase pumps and with some of the connected ions, preferably cations. Through the potent inhibition of ATPase enzymes the inventive substances provide novel approaches for the therapy of pathologies caused by or connected with the defective function these membrane pumps as is the case for gastric hyperacidity modulated by H/K-ATPase or for various cardiovascular pathologies like hypertension with strong involvement of the Na,K-ATPase. By influencing of the ATP controlled transport proteins, the inventive substance can modulate the elimination of metabolites and of xenobiotic substances as in the case of ABC transporters.

An important inventive application of the substance is provided by its particular ability to interact with proteins or definite structural domains of proteins. The inter- or intramolecular interaction promoted by the inventive silicic acid substances can change the structure and the biological function of the bio-molecule, preferably of a protein or glyco-protein.

Due to the dense and even distribution of free silanol groups on the external surface or outer shell of the inventive silicic acid substances, the chemical and biological properties of the inventive substances are significantly influenced by pH and ionic strengths. This structural dependence of the inventive substance from the concentration of alkali ions provides the mechanism of the biological active silicic acid substances to regulate intra and inter-cellular ionic concentrations by the here disclosed feed-back mechanism. Due to the particular interaction of the inventive silicic acid with a protein and modification of its tertiary structure and biological properties the substance of the invention can be applied in the diagnosis, prevention and therapy of diseases as exemplified, but not exhaustively listed, as: hypertension, gastric hyperacidity or diabetes. Further therapeutic application fields for the inventive substance include bone disease, cardiovascular and neurodegenerative pathologies.

Practical application of the inventive substances concerns modulation of biochemical and physiological processes by interaction with proteins, preferably with membrane-, receptor- and signalling-proteins. The herein disclosed ability of the inventive substance to influence the reversible phosphorylation by modifying the structure and properties of certain protein-kinases or phosphatases allows its application in the therapy of certain diseases which are caused by or connected to defective phosphorylation processes. This mechanism could explain the herein disclosed ability of the inventive substances to reduce significantly the pathology symptoms of diabetes providing a novel approach for the therapy of this disease.

Consistent experimental proofs are provided herein for the finding that the sub-nano silicic acids (SNSA) of general formula (I) with the inventive structure and biological activities provide a significant technical progress in comparison with prior art ATPase pump inhibitory substances such as the toxic vanadium derivatives or the cardiac steroids for Na,K-ATPase or the H/K-ATPase inhibitory anti-acid drugs.

5 DETAILED DESCRIPTION OF THE PREFERRED EMBODIMENTS

The object of the present invention is to provide substances which interact specifically with bio-molecules such as proteins by causing specific modifications to their structure and biological function. The main targets of the inventive substances disclosed herein are proteins preferably those involved in reversible phosphorylation processes within cellular signalling and membrane transport.

A solution is provided by the substances of the present invention which are multiple condensed (polymerized) water soluble silicic acids of dimensions below that of the silica nano-particles with diameter φ>5 nm and accordingly the inventive substances are classified as sub-nano silicic acids (SNSA). The particular dimension and molecular structure of the inventive substances make them able to interact specifically with a larger bio-molecule, preferably a protein by modifying appropriately its structure and biological function. This finding is the more surprising since hitherto no structure-specific biological activities were identified neither for mono silicic acid nor for its oligo- or polymeric-condensed derivatives. The current invention discloses: structure and characteristics of the substance of general formula (I), methods of its preparation and stabilization, pharmaceutical compositions comprising at least one substance of general formula (I) and methods of its application in the prevention, diagnosis and therapy of diseases.

It is important to mention that the inventive silicic acid substances overcome the disadvantages of the prior art compounds like: vanadates, cardiac steroids, anti-acid- or anti-cancer-drugs, inhibitors of the ATPases, of drug-efflux pumps and monoclonal antibody based therapeutics. These prior art compounds have been described to interact with proteins preferably with those involved in phosphorylation and membrane transport processes like protein-kinases and phosphatases or with ATPase enzymes an ATP-driven ABC drug efflux pumps. However, the therapeutic application of prior art agents is considerably limited due to their toxicity, frequency of untoward effects or low selectivity. The toxic potential (Tp) of the instant SNSA is at least one order of magnitude lower than that of prior art agents and up to now no undesired effects of the inventive silicic acid SNSA have been identified.

5.1 Structure

For the detailed structural description of the inventive substance the usual notation $Q^s$ (s=0-4) is applied to designate the bonding-type of the individual Si atoms. In this classification the $Q^4$ type Si atoms are linked via adjacent oxygen atom(s) to 4 neighbouring Si atoms, the $Q^3$ to 3, the $Q^2$ to 2 while $Q^1$ is linked to only 1 Si atom through the adjacent oxygen atom. The remaining valences of the Si atoms are involved in Si—OH (silanol) bond(s). Thus the $Q^3$ type Si atom is involved in a single —Si—OH bond, the $Q^2$ type Si in 2 geminal type $Si(OH)_2$ bonds. The $Q^1$ type Si atom bears three —OH bonds —$Si(OH)_3$, silicic acid with $Q^0$ type Si-atom four: $Si(OH)_4$ while $Q^4$ type Si atoms have no —OH groups.

The present invention relates to substances of the general formula (I)

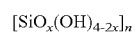

wherein
the Si atoms are $Q^1$, $Q^2$, $Q^3$ and $Q^4$ type Si atoms and
n represents an integer between 12 and 2000 and
x represents a number between 1.2 and 1.8 and
wherein the substance consists of an inner core and an outer shell and
wherein more than 75% of the $Q^4$ type Si atoms are contained in the inner core and more than 75% of $Q^3$ and $Q^2$ and $Q^1$ type Si atoms are contained in the outer shell.

That means, it is essential to the inventive substances of general formula (I) that they consist of an inner core comprising more than 75% of all $Q^4$ type Si atoms and an external shell or outer shell consisting of more than 75% of all Si atoms of type $Q^3$ and $Q^2$ and $Q^1$ altogether Thus, the inventive substances are built up as a layered structure, made up of an internal core consisting of $Q^4$ type Si atoms in more than 75% extent and the external shell consisting of $Q^3$ and $Q^2$ and $Q^1$ type Si atoms in more than 75% extent.

Consequently the internal part of the SNSA substance is defined as an inner core which contains more than 75%, preferably more than 80% and most preferred more than 85% of the $Q^4$ type Si atoms.

Accordingly, the outer shell is defined as the part of the SNSA substance which comprises more than 75% of $Q^3$ and $Q^2$ and $Q^1$ type Si atoms.

Figure 3:
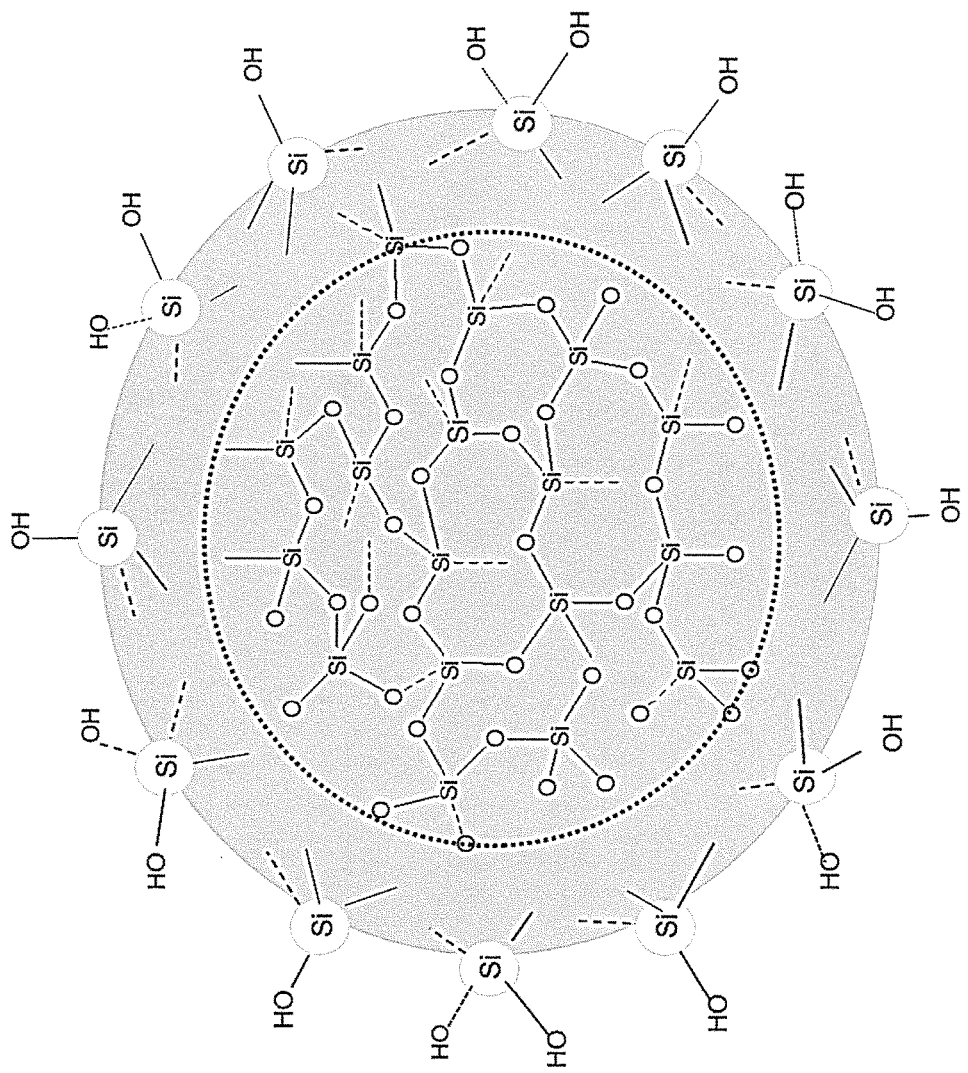

The structural design of the inventive SNSA substances with spheroidal form and with an internal core predominated by $Q^4$ type Si atoms and the external shell of $Q^3$ and $Q^2$ Si atoms is illustrated by FIG. 3.

Figure 4:
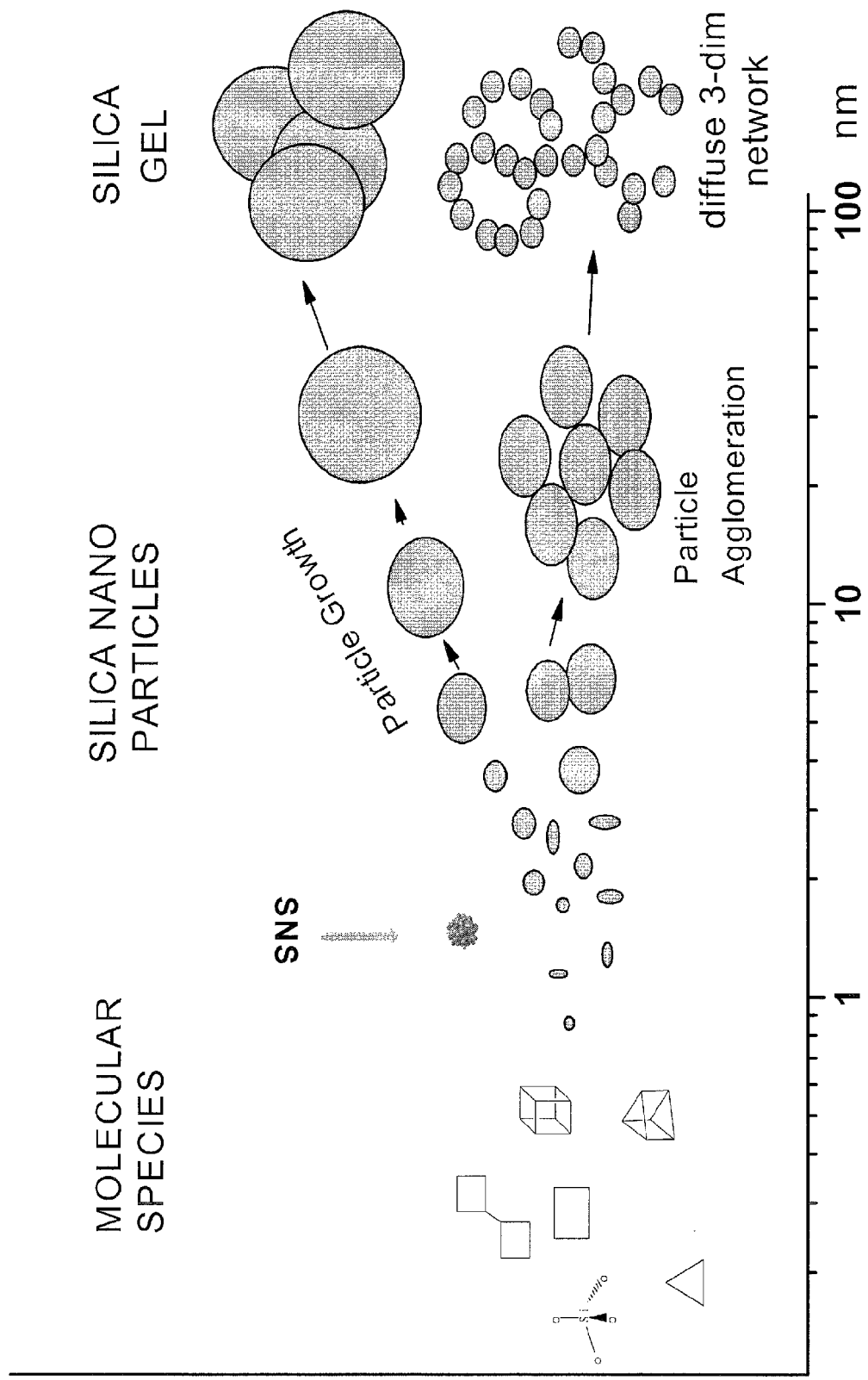

The substances of the invention are particularly structured, low molar mass condensation silicic acids distinguished by their long-term stability and low level toxicity. Their localisation in context of other substances generated by successive oligo-, and polymerization of the ortho-silicic acid and derivatives is shown in FIG. 4. This diagram gives a dimensional overview of the growth of condensation products from simple oligomeric molecular species to high molar mass polymerized silica particles and gel.

Classification of the silicic acid condensation products according to characteristics (dimension, molar mass, polymerization degree, solubility) is given in Table 1.

TABLE 1

Dimensional classification of the silica polymerization products

| Class | Diameter Φ (nm) | (SiOx)n n | Molar mass kg/mol (kDa) | Solubility in water |
|---|---|---|---|---|
| Oligomeric molecules | <0.3 nm | ≤12 | <0.7 | soluble |
| Sub-nano silicic acid (SNSA) Biological active SNSA | 0.3-0.6 nm | 12-20 | 0.7-1.4 | well soluble |
| Sub-nano condensed silicic acid (SNSA) most preferred range Biological active SNSA | 0.6-3 nm | 20-300 | 1.4-20 | well soluble |
| Sub-nano condensed silicic acid (SNSA) Biological active SNSA | 3-5 nm | 300-2,000 | 20-140 | soluble to moderate soluble |
| Polymerized silica nano-particles | 5-50 nm | 2,000-10,000 | 140-600 | colloidal particles |
| High polymeric solid particles/amorphous gel | >50 nm | >10,000 | >600 | insoluble |

These structural limits correspond mainly with generally accepted borderlines but define now more exactly the less precisely described sub-nano particle domain.

Accordingly the inventive biologically active substances belong to the larger class defined as Sub-Nano-Silicic Acid (SNSA) which is an intermediate domain between oligomeric condensed silica species with $\phi \leq 0.3$ nm preferably $\phi \leq 0.6$ nm and that of silica nano-particles $\phi > 5$ nm preferably $\phi > 3$ nm. (Table 1)

Thus, the sub-nano size silica particles of the present invention have a diameter of 0.3 nm to 10 nm, preferably 0.3 nm to 5 nm and most preferred a diameter of 0.6 nm to 3 nm.

It is important to note that the sub-nano-particle domain with $12 \leq n \leq 2000$ and even in the small range of $20 \leq n \leq 300$ comprises actually a very high number of possible homologues and structural isomers in geometrical progression with increasing polymerization degree "n". The here described inventive biologically active SNSA substances constitute only a discrete, very narrow subset of the nearly infinite structural alternatives conceivable in the sub-nano-particle domain.

Thus, the sub-nano-particle size condensed silicic acid molecular species of the present invention have in the chemical formula $[SiO_x(OH)_{4-2x}]_n$ a degree of polymerisation of $12 \leq n \leq 2000$, preferably $14 \leq n \leq 1500$, more preferably $18 \leq n \leq 500$, still more preferably $19 \leq n \leq 400$, and most preferred $20 \leq n \leq 300$. X refers in general to a number between 1.0 and 2.0 as specified below.

In regard to the inventive compounds x is in the range of 1.2 to 1.8, preferably in the range of 1.3 to 1.7, more preferable in the range of 1.4 to 1.6 and most preferred in the range of 1.45 to 1.55. For the optimal case with x=1.5, the formula $[SiO_{1.5}(OH)]_n$ will be obtained.

As "substances of the invention" are classified only the molecular species which are stable, biological active and which can be described by the structural criteria (C1-C12) as disclosed herein. The discovery of the surprisingly stable, biological active species in the domain below the borderline of $\phi \leq 5$ nm, preferably of $\phi \leq 3$ nm diameter and molar mass $\leq 120$ kg/mol (kDa), preferably $\leq 20$ kg/mol (kDa) is an important technical progress in comparison with the prior art described very instable silica species in this domain, which lacked any signs of biological activity.

Figure 5:
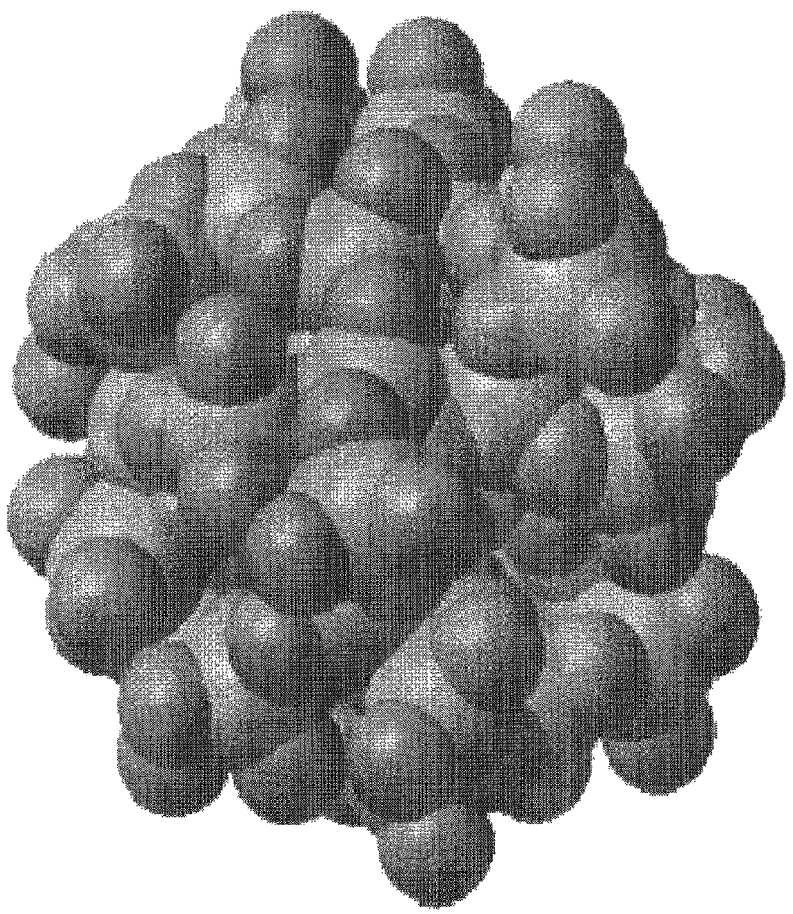

Structural criteria (C1-C12) which apply for the classification of the inventive SNSA species of general formula (I) and which distinguish them from the large variety of randomly structured silica species are defined by the invention and described as follows:

C1 The spheroidal form or almost spheroidal form with molecular diameter $\phi$(nm) in the 0.3 nm$\leq\phi\leq$5 nm preferably of 0.6 nm$\leq\phi\leq$3 nm range. Approximation with a spheroidal or almost spheroidal form reflects the tendency to a symmetrical or at least even disposal of the Si—O—Si and Si—OH bonds. Although the inventive substances do not have a rigorous structural symmetry, their structural elements are nearly symmetrically arranged including the preferably equalised, regular alternating distribution of the Si—OH groups on the outer shell. FIG. 5 illustrates the spheroidal shape of the inventive silicic acid molecule with equalised distribution of the free Si—OH groups on the outer shell.

C2 Molar mass in the 0.7-140 kg/mol (kDa) range, preferred in the 1.0-100 kg/mol (kDa) range, more preferred in the 1.2-70 kg/mol (kDa) range, still more preferred in the 1.3 to 40 kDa range and most preferably in the 1.4-20 kg/mol (kDa) range or domain which justifies to characterize the inventive substances as molecular species C3 Polymerization degree=number "n" of the condensed silica units which is in the $12 \leq n \leq 2,000$ range, preferably $16 \leq n \leq 1200$, more preferably $17 \leq n \leq 700$, still more preferably $19 \leq n \leq 400$, and most preferred in the $20 \leq n \leq 300$ range. Moreover water soluble substances of the general formula (I) are preferred. Solubility in water is provided by the substances in the range n=16 to n=1200.

Molecular dimensions and stability of the here disclosed silicic acid were characterized by physical methods like: dynamic light scattering (DLS), Nuclear Magnetic Resonance (NMR) Size Exclusion Chromatography (SEC), Viscosimetry, Infrared (IR) and Raman spectroscopy, Fluorescence spectroscopy, Transmission Electron Microscopy (TEM), N2 sorption isotherms and other techniques as illustrated by the examples of the present application.

C4 The numerical ratio between the sum of the $Q^3$, $Q^2$ and $Q^1$ type Si atoms altogether and the $Q^4$ type Si atoms is between 1.5 and 2.5, preferably between 1.75 and 2.25, more preferably 1.9 and 2.1 and most preferably almost 2.

Almost all of the $Q^1$ type Si atoms are contained in the outer shell. The ratio of the $Q^1$ type Si atoms is less than 30%, preferably less than 20%, more preferably less than 12% and most preferably less than 6% of the $Q^2$ all Si atoms. Accordingly, if not otherwise specified the $Q^1$ Si atoms are included in the sum of the $Q^2$ Si atoms.

The numerical ratio between the $Q^3$ and $Q^2$ type (including $Q^1$) atoms is between 0.5 and 1.5, preferably between 0.65 and 1.35, more preferably between 0.8 and 1.2 and most preferably between 0.9 and 1.1.

At least 75%, preferably 80% and more preferably 85% of all $Q^4$ type Si atoms are contained in the inner core.

At least 75%, preferably 80% and more preferably 85% of all $Q^3$ and $Q^2$ type Si atoms are contained in the outer shell.

C5 The balanced ratio of the Si atoms of type $Q^4$, $Q^3$ and $Q^2$ is considered a preferred embodiment of the inventive silica structure and of the correlated biological activities. Balanced means identical or very close to a 1:1:1 ratio of the $Q^4$:$Q^3$:$Q^2$ type Si atoms while close to is defined as a deviation of a maximum of 30%, preferred of 20% and more preferable of a maximum of 10% deviation from the ideal balanced 1:1:1 proportion. Thus, the admitted deviation from the ideal balanced ratio of the Si atoms of type $Q^4$, $Q^3$ and $Q^2$ is maximum 1:0.7:0.7 to 1:1.3:1.3, preferably 1:0.8: 0.8 to 1:1.2:1.2 and more preferably 1:0.9:0.9 to 1:1.1:1.1. Balanced distribution of the Si atoms of types $Q^4$:$Q^3$:$Q^2$ with a nearly 1:1:1 ratio is supported by the $^{29}$Si nmr spectra.

C6 Chemical formula of the inventive biological active SNSA molecular species with the ideal balanced, nearly (1:1:1) ratio is described by formula $[Si\,O_{1.5}(OH)]_n$. This general formula is an analogue to that of the multiple condensed silicate cages (FIG. 1) like the prismatic hexamer $[Si_6O_9(OH)_6]$, cubic octamer $[Si_8O_{12}(OH)_8]$ or prismatic decamer $[Si_{10}O_{20}(OH)_{10}]$ in the domain n≤10. Since these prior art multi-cyclic silica cage species with the analogue general formula manifest no biological activities the here disclosed biological active sub-nano silicic acids in the domain 12<n<2000 accomplish an important technical progress.

According to the balanced, optimally (1:1:1) ratio, the number of the free silanol (Si—OH) groups is nearly equal with the total number of Si atoms. This inventive high number of free silanol groups justifies definitely the term "silicic acid" for the substance of the invention. Moreover this high number "n" of the free (Si)—OH groups enables the preferred structural embodiment of the sub-nano spheroidal silicic acid of the invention. This condition is furthermore essential for the optimal inventive interaction of the SNSA substances with bio-molecules, preferably with proteins.

C7 The inner core of the inventive structure is formed by a more or less compact silica framework ($SiO_2$) of $Q^4$ Si atoms. Assembly of this inner core is started with a central seed unit which can be: mono-silicic acid or its simple linear or cyclic derivates with 3 to 6 Si-atoms, preferably 4 or 5 Si atoms. Alternatively a cage type multicyclic silica unit, like the prismatic-hexameric, cubic-octameric or the prismatic-decameric silicate frame can serve as seed unit.

Figure 6:
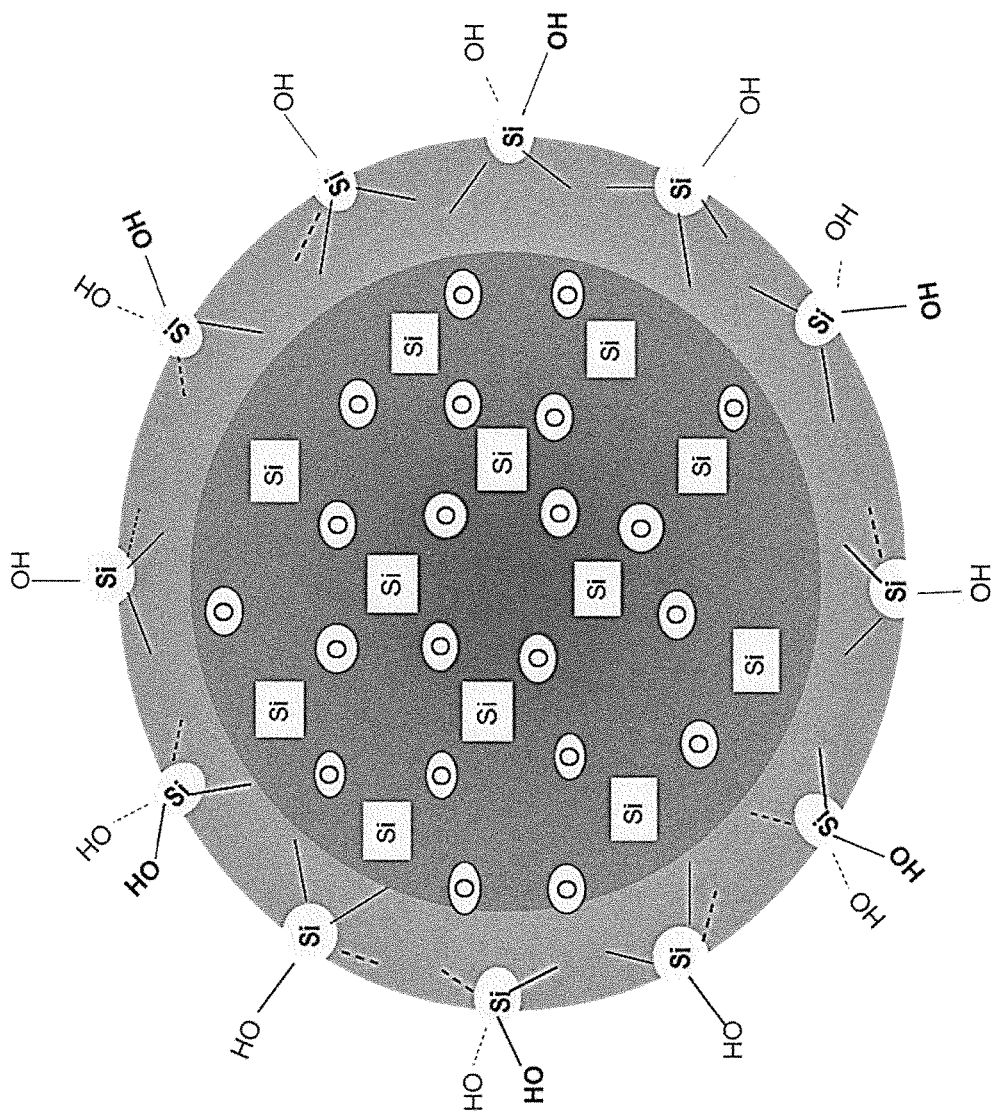

C8 Internal shell(s) of similarly $Q^4$ type Si atoms were assembled adjacent to the seed unit. Starting with a cyclo-silica seed unit each $Q^2$ type Si atom will condense with either 2 silicic acid units thus each successive shell contains twice of the Si atoms of the precedent level in a geometric progression. Starting with a cage type silica as seed with $Q^3$ Si atoms, the adjacent shell will have the same number of Si atoms. These are of $Q^3$ type at first thus can condense with either 3 mono silicic acid units. Linearly condensed silicic acid oligomers generate a different progression in accordance with their mixed $Q^2$ and $Q^1$ type Si atoms. The here outlined growth patterns of the inner shells with $Q^4$ type Si atoms is illustrated in FIG. 6. In almost all embodiments of the inventive structures the number and type of the Si atoms in a layer are determined by the number and type of the Si atoms in the previous layer. Similar numerical limitations exist by the construction of the outer shell with $Q^3$ and $Q^2$ Si atoms. This means that some numerical values e.g. those which form a geometrical progression were predetermined in the construction of the layers as disclosed by the examples.

Accordingly only some discrete values from all integers of the domain of n between 12 and 2000 are preferred for the fulfilment of the inventive structural criteria C1-C12. That means, only some preferred discrete values of numbers n of condensed silicic acid units in the smallest range of 20 to 300 or the largest range of 12 to 2000 are more preferred than others.

Surprisingly the biologically active inventive SNSA are characterized by a narrow distribution of the molecular diameter values as evidenced by sharp peak(s) in the Dynamic Light Scattering (DLS) spectrum. This means that products formed by the method of this invention correspond to a very narrow dispersion of the molar masses as further confirmed by size exclusion chromatography (SEC). Embodiments of the inventive structure for discrete numerical values of "n" are described by examples illustrating further regularities of the molecular construction.

Above disclosed structural characteristics are determined according to this invention by several factors preferably by the specific preparative conditions (concentrations, pH value, temperature, mixing intensity, duration) of the synthesis phases. These parameters are set differentially for the "induction" phase of the synthesis, where the seed for the SNSA is generated. For the "condensation" phase, the operating conditions are specifically adjusted, whereby the controlled growth of the molecule takes place. The values and the dynamics (variation along the duration of the phase), of the operating parameters within this phase, result in the formation of SNSA characterized by very narrow distribution of the degree of condensation "n", around discrete values, which are thermodynamically favoured, under the prevailing operating conditions.

The conditions of the "stabilization" phase are tailored such as to stop the growth of the SNSA and confer to the product a degree of stability, which is definitely higher the ones known in the art. Here disclosed preparation methods are quite different from previous art, which produce much larger molecular masses and much broader Gaussian distribution of the degrees of condensation "n" of the silica units.

It should be mentioned however that the inventive synthesis disclosed herein always produces a mixture of inventive substances and each of these substances are defined by the limitations as disclosed in claim 1. Thus it is clear to a skilled person that not only one compound with a single value of n is synthesized. The inventive substances are classified as mixtures with a narrow distribution of the n values within the maximum range of n=12 to 2000, preferably within the range of n=16 to 1200, more preferably within the range of n=18 to 500, still more preferably within the range of n=19 to 400, and most preferably within the range of n=20 to 300.

Thus one important aspect of the invention in contrast to the inactive polymerised and/or colloidal silica particles of the state of the art is that the inventive substances have a narrow distribution of the n values within the ranges disclosed herein. The inventive substances clearly do not have something like a Gaussian distribution over the maximum range of n=12 to n=2000. When using analytical methods such as dynamic light scattering (DLS) or size exclusion chromatography (SEC) for analysing the inventive substances, narrow distributions of the molecular diameter ϕ and of the molar mass Mr of the inventive substances corresponding to a single discrete n value falling within the ranges disclosed herein can be detected, wherein the n values differ about 25%, preferably about 20% and more preferably about 15% around one specific preferred n value. Thus within the maximum range of n=12 to n=2000 the inventive substances are synthesized with a relatively narrow distribution of 25%, preferably 20% and more preferably 15% around a single discrete n value. When carrying out the inventive synthesis of the inventive substances it could be that for instance a substance having an n value of n=36 or n=45 or n=92 or n=96 or n=180 or n=192 or n=288 or n=360 or n=450 or n=552 or n=654 or n=720 or n=810 or n=990 is the most preferred compound in the mixture of inventive substances while the other compounds of the mixture of inventive substances are not distributed equally or in a Gaussian distribution within the range from $12 \leq n \leq 2000$, rather narrow distribution of compounds having an n value within a range differing not more than 25%, preferably not more than 20% and more preferably not more than 15% from compound having the preferred n value is found. If for example an inventive mixture is obtained wherein the most preferred n value is 96 and about 25% of all inventive substances have this n value the remaining 75% of the substances do not have n values from 12 to 2000, instead the n values are narrowly distributed around the preferred n value of 96. A "narrow" distribution means that the n values have a value of around ±25%, preferably ±20% and more preferably ±15% around the most preferred n value. Concerning the above example wherein the most preferred n value is 96 for about 25% of the inventive substances, the remaining 75% of the inventive substances will have n values between 72 and 120 (25% distribution), preferably n values between 77 and 115 (20% distribution) and more preferred n values between 82 and 110 (15% distribution).

Thus as used herein the term "narrow distribution" refers to a distribution of the inventive substances around one discrete most preferred n value within a range of distribution (ROD) of ROD=n−0.25n to n+0.25n, preferably ROD=n−0.20n to n+0.20n and more preferably ROD=n−0.15n to n+0.15n. In case a definition with an absolute number is preferred, the range of distribution can be defined as: ROD=n−125 to n+125, preferably ROD=n−100 to n+100 and more preferably ROD=n−75 to n+75 for n values between 600 and 2000 or ROD=n−60 to n+60, preferably ROD=n−40 to n+40 and more preferably ROD=n−20 to n+20 for n values between 300 and 600 or ROD=n−30 to n+30, preferably ROD=n−20 to n+20 and more preferably ROD=n−10 to n+10 for n values between 30 and 300.

Moreover it has to be stated that the formation of substances with a specific and preferred discrete n value can be supported by the reaction parameters and depending on the reaction time and temperature and concentration substances with preferred n values in the lower range of n=12 to n=300 are formed while other reaction parameters to lead to preferred n values in the upper range of n=300 to n=1000 or 1500 or 2000.

However, regardless of the specific preferred number for n, all inventive mixtures within the ranges disclosed and defined herein are working examples and show the disclosed and proven activity as mentioned and evidenced herein.

C9 Building pattern units with 4 and 5 Si atoms containing cyclo-silica rings are preferred by the construction of the inner and of the outer shells in the assembly of the inventive substance. Other patterns are not excluded but cyclo-silica units with 3 Si atoms make the structure too dense and tensioned. Involvement of 6 Si atoms containing rings is not excluded but larger cyclo-silica units reduce the compactness and stability of the whole structural frame. It is assumed that a compact constitution of the structural assembly lacking strained structural elements as well as without internal cavities or large holes provides the optimal overall stability of the molecule.

C10 An external surface with dense and evenly distributed high free Si—OH groups is a decisive structural requirement for the accomplishment of the preferred interaction of the inventive SNSA species with bio-molecules, preferably proteins. The free OH groups bond to the silica framework of the external shell built up by $Q^3$ and $Q^2$ type Si atoms connected with Si—O—Si bonds. Since each $Q^3$ type Si atom has one —OH and each $Q^2$ type Si atom 2 —OH groups the total number of Si—OH (silanol) groups is 50% higher than of the Si atoms in the external shell. For the whole sub-nano silica molecule the number of silanol groups equals the "n" of the Si atoms in accordance with the most preferred general formula $[SiO_{1.5}(OH)]_n$.

The density of the Si—OH groups on the surface of the inventive SNSA is defined by $\alpha_{OH}$ expressed as number of Si—OH groups per square nanometer ($nm^2$) of the surface. The here presented data is calculated with the surface area $A=R^2\ 4\pi$ of the sphere defined by the external Si-atoms. Calculation with the VdW (Van der Waals) surface is adequate for the assessment of the molecular dimension but less so for the SiOH density.

The density of silanol groups on the external shell of the inventive silicic acid provide mean values of $\alpha_{OH}$>2.5 preferably $\alpha_{OH}$>3.5 free Si—OH groups/$nm^2$. Silanol group values for amorphous silica $\alpha_{OH}$ were determined by chemical derivatization of the free silanol groups obtaining density values in the range of 3.0 to 6.0 groups/$nm^2$. However these $\alpha_{OH}$ values by solid particles reflect the sum of internal & external Si—OH groups thus the density of free OH groups on the external surface is significantly lower.

In comparison with the amorphous silica particles with internal and external Si—OH groups the contribution of the internal Si—OH groups in the inventive silicic acid molecule is rather reduced. By the dense and even disposal of the free Si—OH groups bonded to the $Q^3\ Q^2$ and $Q^1$ Si atoms of the external shell (FIG. 7) the inventive biological active silicic acid provides a definite technical progress in comparison with previous art silica particles with a high proportion of internal silanol groups.

Computational model data indicate that the partition of the Si—OH groups with regularly alternating $^3Q$ and $^2Q$ type Si—OH groups on the external surface is more favoured as their unordered random disposal. Moreover, this structural particularity has a significant contribution for the optimal embodiment of the inventive interaction with bio-molecules, preferably with proteins. Ratio of the $^3Q$ and $^2Q$ type Si—OH groups on the external surface of the inventive molecule was investigated by IR spectroscopic methods as disclosed in the examples.

C11 Discrete values of n, were revealed surprisingly by calculation of the surface density of the Si—OH groups/$nm^2$ on the external surface defined by the Si atoms of the outer shell. The density of the Si—OH groups as a function of the polymerization degree is not a constant value or did not show a linear variation. The invention discloses the surprising existence of some discrete polymerization degree values "n". These discrete n values with elevated silanol density values are disclosed in examples of the present description.

C12 It is important to mention that the fulfilment of the main structural criteria C1-C10 is essential for the inventive stability of the substances of general formula (I) which are the first stable silicic acid compounds identified in the range as disclosed herein. The fulfilment of the structural criteria for stability is an essential feature of the inventive substances regarding their inventive medicinal application in the treatment, prophylaxis and diagnosis of various diseases.

Calculation of the silanol density on the outer shell of the inventive silicic acids for a nearly balanced ratio of the $Q^4:Q^3$ and $Q^2$ Si atoms shows a non linear variation as function of the n values in the general formula (I). This suggest that some discrete "n" values are better suited for the accomplishment of the dense distribution of the silanol groups as others from the range of $18<n<300$.

5.2 Preparation and Properties
Preparation of the Substances with Formula (I)

$$[SiO_x(OH)_{4-2x}]_n$$

where n represents an integer between 12 and 2000 and
X represents a number between 1.2 and 1.8.
comprising the steps:
- a) admixing the inorganic silicon compound or a tetra-alkyl-ortho-silicate with water or water-solvent mixture
- b) carrying out an induction phase at a pH value in the range of 6.2-4.5 under stirring for less than 60 minutes,
- c) conducting a condensation phase at a pH in the range of 4.5-3.8 with a fine tuned, slow decrease of the pH along a linear gradient and
- d) conducting a stabilization phase by rapid change of the pH value of the solution either to pH 2.1±0.3 or to a pH>8.4, while the temperature during the complete preparation should be in the range between 4° C. and 80° C.

The slow decrease of the pH value along a linear gradient according to step c) is performed for a time of at least 5 minutes.

A further aspect of the present invention relates to substances available according to the above described method.

Important embodiment of the invention is the selective synthesis of the biologically active SNSA derivatives starting preferably from a largely accessible silicon compound. The invention also comprises methods for the isolation of the biologically active SNSA fraction from the bulk of randomly condensed low molar mass silicic acid synthetic mixtures or biological extracts.

Preparation of the inventive biologically active silicic acid is accomplished by synthetic methods starting from large scale available inorganic silicon compounds, such as silica, alkaline silicates or silicon-halogenides like Si-tetrachloride. Another type of starting material for the synthesis are some silicon-organic derivatives such as the tetra-alkoxy-ortho-silicates e.g. tetra-ethyl ortho-silicate (TEOS) or tetra-methyl ortho-silicate (TMOS) or alternately some hydrolysable Si-complexes with poly-hydroxy-compounds.

One preferred embodiment is the multi-parameter controlled transformation of the "in situ" synthesized mono-silicic acid into the inventive substance. However the mono-silicic acid provided by prior art methods i.e. by: protonation of alkaline silicates or by similar methods is instantaneously transformed in high degree polymerization products as described in the literature.

The invention discloses methods to transform with high yields the in situ prepared silicic acid into the inventive biological active sub-nano silicic acid SNSA, avoiding the spontaneous polymerization of the starting material. Each inventive method comprises the: (i) "induction phase" which involves the induction of the purposeful low-molar mass condensation (ii) "condensation phase" conducted for selective high yield preparation of the inventive SNSA and to avoid the uncontrolled random polymerization and (iii) "stabilization phase" in which the product is adequately stabilized.

Selectivity and high yield of the inventive preparation methods of SNSA are accomplished by rigorously controlled concentration, pH, temperature and duration of each reaction step. Working parameters were defined differentially for each phase of the manufacture. Thus the selective hydrolysis and transformation of tetra-alkyl ortho-silicates $Si(OR)_4$ in the inventive SNSA comprises the "induction" the "condensation" and the "stabilization" phases which are rigorously conducted and controlled.

One preferred embodiment is the transformation of tetra-alkyl ortho-silicates with formula $Si(OR)_4$ where R=methyl, ethyl, propyl; or butyl with concentration of the starting material in the 0.02-0.6 mol*$L^{-1}$ range. Inventive preparations from Si-tetra-alkyl ortho-silicates are conducted according to the invention to provide the purposeful transformation of this "in situ" generated silicic acid into the inventive substance and to prevent its uncontrolled polymerization.

For the "induction phase" of the reaction between the tetra-alkyl ortho-silicate and water, or water with alcohol, pH values in the range of 4.5-6.2, preferably of 5.4±0.4 were applied. This induction phase is of short duration and takes not longer than 60 minutes, preferably as short as 10 minutes and is recommended to be conducted under vigorous stirring. During the next "condensation phase" the pH should be in the range of 4.5-3.8 with a finely tuned, slow decrease along a linear gradient with a time duration of at least 5 minutes.

An important inventive contribution is the rigorous control of the temperature during all phases of the synthesis and stabilization of the inventive substance. Preferred temperature range of the induction phase is between 4-50° C. preferably in the range of 15-40° C. Deviation from the prescribed pH or temperature value and devolution may change significantly the composition and activity of the product. Stopping of the condensation process to prevent the higher degree polymerization of the inventive silica is accomplished by rapid change of the pH value of the solution either to pH 2.1±0.3 or to pH≤8.5.

Similar phases of the induction, polymerization and stabilization are defined in the inventive preparation of the sub-nano silicic acid started from another large scale silicon compounds such as alkaline silicates preferably sodium silicate or from amorphous silica or from silicate minerals.

5.3 Characterization
DLS and Zeta Potential

Dynamic light scattering (DLS) measurement of the condensed silicic acid species according to the invention showed the existence of stable species in the preferred diameter range of 0.6<φ<3.0 nm. Applying Dynamic Light Scattering and Zeta potential measurements the size of SNSA the stability of the system dependant on pH and concentration was established in detail. The DLS technique in combination with the Zeta potential assessment were successfully applied to control the formation of associated/aggregated particles of higher φ>3.0 nm dimension.

It is known that the stability of nanosized particles with respect to aggregation depends on the balance between attractive London-Van der Waals and repulsive electrostatic forces. The electrostatic repulsion depends on the ionic strength and on the surface potential (Nernst potential), which can be altered by adjusting the pH value of the suspension. While the Nernst potential is experimentally not accessible, the electrokinetic potential at the shear plane, the zeta (ζ) potential, can be monitored. Dispersions are typically regarded to be stable when the zeta potential is higher than ca. |30 mV|, whereas particles tend to form aggregates near the iso-electric point (IEP), which is defined as the pH at which the zeta potential is zero. Therefore, the zeta potential measurements in suspensions containing SNSA particles were investigated at controlled pH values.

Dynamic light scattering measurement of the condensed silicic acid species according to the invention showed the existence of stable species in the preferred diameter range of $0.6 < \phi < 3.0$ nm.

Size exclusion chromatography relies on separating silicic acid oligomers and polymers in solution on the basis of their molecular sizes. The method was applied to characterize the inventive substance in comparison with monomeric and polymeric silicic acid samples. The use of silica based gels is not recommended due to the very strong irreversible interaction with the biological active silicic acid. Very good and reproducible results were obtained with organic polymer based gels as stationary phase in a high performance size exclusion chromatography device. Refractive index based detector systems were applied since the inventive substance has no measurable absorption in the UV-vis region.

Low molar mass condensed silicic acid species disclosed by the invention are well soluble in water the solutions are colloidal and are remarkably stable for long term storage at room temperature at certain pH values. Its stability in the basic pH range between 8.5-13.0 is caused by the repulsion of the negatively ionized Si—O groups which impedes further condensations. Experimental Zeta potential measurements on the biological active SNSA provided values at ca. (−50 mV) confirming that the species are negatively surface charged that very stable and do not agglomerate.

Surprisingly the inventive sub-nano-spheroidal condensed silicic acid is remarkably stable also in the acidic range preferably at pH 1.8-2.2. Its low tendency for polymerization in the specified acidic pH range may be explained by the reduced tendency for condensation around the zero charge point at pH ~2.0 According to their stability both in the basic and in a narrow acidic range as above specified the here disclosed sub-nano silicic acid derivatives represent a definite technical progress to the prior art, low molecular condensed very unstable silicic acid species which polymerize spontaneously to insoluble silica particles and silicagel.

The charge dependent stability of the here described silicic acid is particularly influenced by the disposal of the free Si—OH groups in the external surface. In basic pH medium this provides a symmetrical and dense partition of the negative charges on the external surface. Thus, all the molecules will have a mutual repulsion and their solution will remain very stable. This negatively charged cover is a very efficient protection in preventing the aggregation and transformation of the particles of the inventive substance.

Besides the above outlined electrostatic factors the inventive substance has more profound structural grounds for its outstanding thermodynamic stability. Actually the silicic acid of the invention is built up by a compact internal silica core with predominantly Q4 type Si—O bonds and surrounded by the outer shell with the preferably maximum number of free Si—OH groups displayed on the surface. Inter-conversion of free silanol (Si—OH) bonds to condensed (Si—O—Si) groups may occur within the molecule but these influence less the overall preferred stability of the spheroidal shape than external disposal of the Si—OH groups.

The low negative zeta value (−50 mV) shows that the particles are very stable and have negative surface charge. If the zeta value is approaching 0, this means that the particles are not stable and tend to agglomerate, but this is not the case for the inventive biological active SNSA silicic acid. If the Zeta value is increasing than the particle size will increase too; the zeta value depends on the type of the solvents, pH of the measured solution, and concentration and type of solid particles. In the current case, the zeta value is very negative and the pH is about 9-9.5. A series of samples have been measured and compared at either constant concentration or constant pH. A complete reproducibility of the measured Zeta values and hydrodynamic diameters of the SNSA particles have been achieved. This means that the particles are negatively surface charged and are very stable and do not agglomerate at the conditions specified above.

Stability on Inert Supports

Energetic removal of water from the solution of the inventive substances, performed by heating, advanced vacuum drying, lyophillisation and other procedures can lead to a dramatic loss of the biological activities. Probable causes are the multiple intermolecular elimination (condensation) of water with building of covalent Si—O—Si bonds and formation of larger particles with n much higher than 2000.

The present invention discloses that the activity of the inventive SNSA substances can be fully maintained if the drying is performed with or on an inert support. Suitable support materials for the invention are water soluble, pharmaceutically neutral solids or non-volatile liquids, Preferred support materials are multiple hydroxylated organic substances such as polyols e.g. ethylene glycol, propylene glycol, glycerol, sorbitol, mannitol, dulcitol, pentaerythritol. Most preferred support materials are those which are already authorized for pharmaceutical formulations as neutral supports and described by the chapter "Pharmaceutical formulations" of the present invention. Preferably any suitable carrier can be used that does not initiate or support or catalyse the dehydration under simultaneous formation of Si—O—Si bonds. Such preferred supports are neutral substances preferably without positively and negatively charged functional groups.

Long-term stability of the inventive silicic acid in its watery solution or on neutral supports was investigated by periodical assessment of DLS and zeta potential as well as by ATPase inhibitory measurements. It was confirmed that SNSA solution are stable for several month storage at room temperature. Moreover, the activity of SNSA on the inventive support materials is fully conserved for at least 24 months. This long-term stability of the inventive substances on the inert supports according to the invention provides the optimal forms for their inventive applications in prevention and therapy of diseases.

Aggregation Sub-nano condensed silica species according to invention can form aggregates considered as reversible if the initial species may be reformed by physical treatment (heat, ultrasound) or by chemical agents (pH change, dilutions, salts). Transformation of SNSA in higher molar mass species by formation of novel (Si—O—Si) bonds between silanol groups can be irreversible if it leads to formation of insoluble silica particles. This process is favoured by increased ionic concentration of the solution, i.e. by adding of inorganic salts.

Viscosity: is a very sensitive method to study the process of transforming mono-silicic acid in oligomers and polymers. It is possible to establish the dimension of the dispersed particles in the colloid solutions of silica classified as sol.

NMR

Nuclear magnetic resonance (NMR) spectroscopy is based on the response of the nuclear spins to radio-waves under an external magnetic field and is very applicable for studying the first and the second coordination sphere of a certain type of atom. NMR is observed only for those atomic nuclei having non-zero spin; however almost for each chemical element there is an isotope that meets this requirement. The magic-angle-spinning technique allows the successful application of NMR spectroscopy not only to liquids but also to solids. Hence, NMR is widely used for studying the structure of intermediate species in solidification processes of nanoparticles, external and internal surface active sites of porous nanomaterials, atomic coordination and guest-host interactions. Information about the connectivity of the Si atoms can be obtained from the measurement of the $^{29}$Si NMR spectra.

This is expressed by the fraction $Q^s$ where "s" indicates the number of siloxane (O—Si—) bonds and "4-s" gives the number of Si—OH (silanol) groups. In the $^{29}$Si NMR spectra of the biological active silicic acid chemical shift values corresponding to $Q^4$, $Q^3$, $Q^2$ and $Q^1$ type Si atoms are found. These data confirm the inventive structure with the internal core built up preferably by quaternary ($Q^4$) Si atoms and the external shell with $Q^3$, $Q^2$ and $Q^1$ type Si atoms. The ration of the integrated Gaussian curves pleads for the balanced ratio of the $Q^4$, $Q^3$ and $Q^2$ type Si atoms IR and Raman Spectroscopy Fourier Transform infrared (FTIR) and Raman spectroscopy are the two principle varieties of vibrational spectroscopy with electromagnetic radiation. FTIR spectroscopy is based on absorption of infrared radiation from atomic vibrations, whereas Raman spectroscopy consists in inelastic visible/near-visible light from atomic vibrations. Both techniques provide information on short- and intermediate-range ordering, i.e. the geometry of silica representing the atomic nearest neighbourhood and the manner of linkage of these polyhedra into larger clusters.

Infrared (FTIR) and Raman spectroscopy provide excellent tools for structure analysis of silica nanoparticles based on the different response to the incident radiation from characteristic atomic clusters distinguishable on sub-nanometric scale. Among the various spectroscopic methods Raman spectroscopy compares favorably with its ability to detect amorphous substance and to fingerprint different crystalline silica materials. Additionally, the Raman scattering cross section from organic molecules is very high, while water is poor inelastic light-scatterer, make Raman spectroscopy promising as a method for probing the structure of crystalline nanoparticles stabilized in water.

Raman spectroscopy is applied to probe the degree of structural disorder in micron-sized self-assemblies of closely packed nanoparticles. Insights into structural defects are gained from the spectra collected from the samples. The Raman scattering near 960 cm$^{-1}$ is indicative for point defects in the silicon-oxygen framework (violated Si—O—Si linkages), while the domain structures in the nanoparticles are quantified by fitting the shape of the multi-component band in the range 250-650 cm$^{-1}$, generated by SiO$_4$-ring modes. The main spectral features of amorphous silica are a broad band near 450 cm$^{-1}$ and signals at 495 cm$^{-1}$ and 606 cm$^{-1}$, generated by 6-, 4- and 3-membered rings, respectively.

FTIR spectroscopy alone can unambiguously identify various types of surface hydroxyl groups and thus to quantify the number of the corresponding active sites. Commonly, the O—H bond stretching mode of the surface OH groups is used to analyze the acid sites. A sharp IR peak is observed in the range 3550-3800 cm$^{-1}$, the one near 3745 cm$^{-1}$ arises from terminal silanol group and near 3615 cm$^{-1}$ generated by Si(OH) acid sites.

Fluorescence

Preparation of the inventive silicic acid is monitored by fluorescence spectroscopy. This assay is based on the observation that polymerization of silica produces a fluorescence shift and intensity enhancement in spectrum of the specific indicator PDMPO [2-(4-pyridil)-5-((4-2-dimethylaminoethylcarbamoyl)methoxy)-phenyl-oxazole]. This assumed that the fluorescence shift is due to an interaction between PDMPO and polymeric silicic acid Practically, the fluorescence emission intensity at 510 nm (338 nm exc.) of PDMPO is used to monitor the polymerization of the silicic acid within the preparation of the inventive substance.

Safety

Silicic acid derivatives according to the invention have LD$_{50}$ values in the range of 240-300 mg/kg body weight assessed in mice and rat by intravenous and intraperitoneal single dose administration. Acute toxicity values of cardiotonic steroids are several order of magnitudes higher, e.g. LD$_{50}$=0.1 mg/kg body weight for Digoxin. The lethal dose of digitalis glycosides is about 20 times the maintenance dose which illustrates the narrow range between therapeutic and toxic doses.

Reduced toxicity of the inventive silicic acid is the main advantage of the disclosed substance in comparison with prior art vanadates or cardiac steroids The definitely lower toxicity of the inventive substance in comparison with prior art vanadates provides an essential advantage for human therapeutic applications of the novel compounds.

5.4 Biological Activity

Interaction with Proteins

Figure 8:
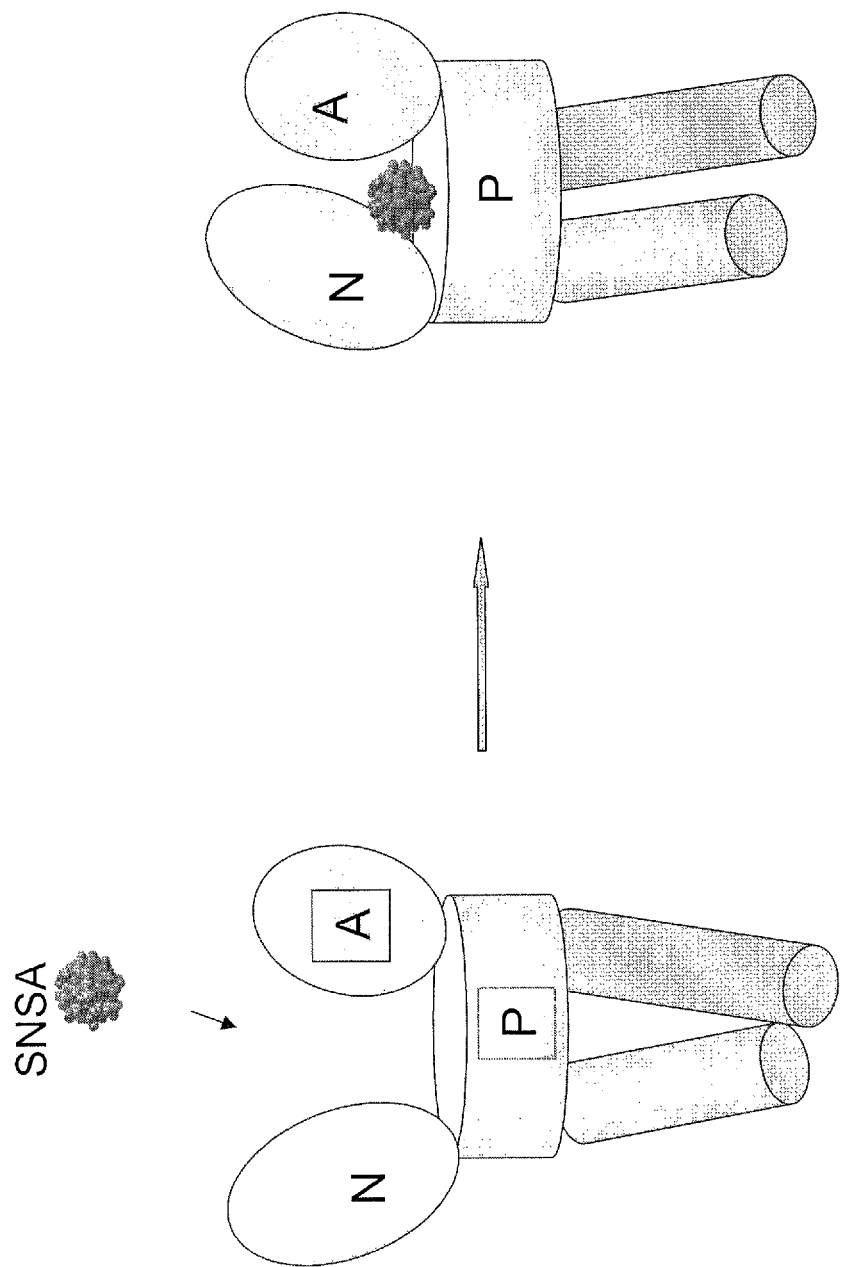

Important practical embodiment of the here disclosed sub-nano condensed silicic acids results from their inventive ability to interact with proteins i.e. with certain structural domains of a protein illustrated in FIG. 8 and FIG. 9. This interaction modifies the structure of the targeted protein and changes its biological properties. A possible mechanism is to impede the access of an agonist to the active site of an enzyme or to close an open instable conformation of a protein. The inventive SNSA could inhibit an ATP fuelled enzyme by stabilizing a closed conformation with unexposed active site, e.g. to impede the addition of the phosphate moiety (FIG. 8).

A preferred embodiment of the invention is the interaction of the here described substance SNSA with proteins directly involved in reversible phosphorylation processes within signal transduction and membrane transport. The internal structural modifications of a protein produced by the intermolecular interaction of its domains with SNSA are able to change specifically certain biological activities. This inventive modulation of structural and biological activities provides a definite technical progress in comparison with prior art interaction with silica nano-particles of large diameter. Further significant progress is the homogenous art of the inventive interaction in contrast to the previous art heterogenous interaction with large, non soluble solid silica particles.

An essential structural feature of the particularly condensed silicic acids is their nearly spheroidal shape and the display of almost all free Si—OH bonds on the surface of the molecule as illustrated in FIG. 5. The sub-nano-silicic acid molecules according to the invention with preferred diameter in the 0.6<ϕ<3 nm range are able to display almost all Si—OH groups on the outer surface. Due to the compact internal silica core (with no Si—OH bonds) and the dense, outward directed Si—OH bonds on the external surface, the substance of the invention is optimally designed to interact with bio-molecules preferably with proteins.

Figure 10:
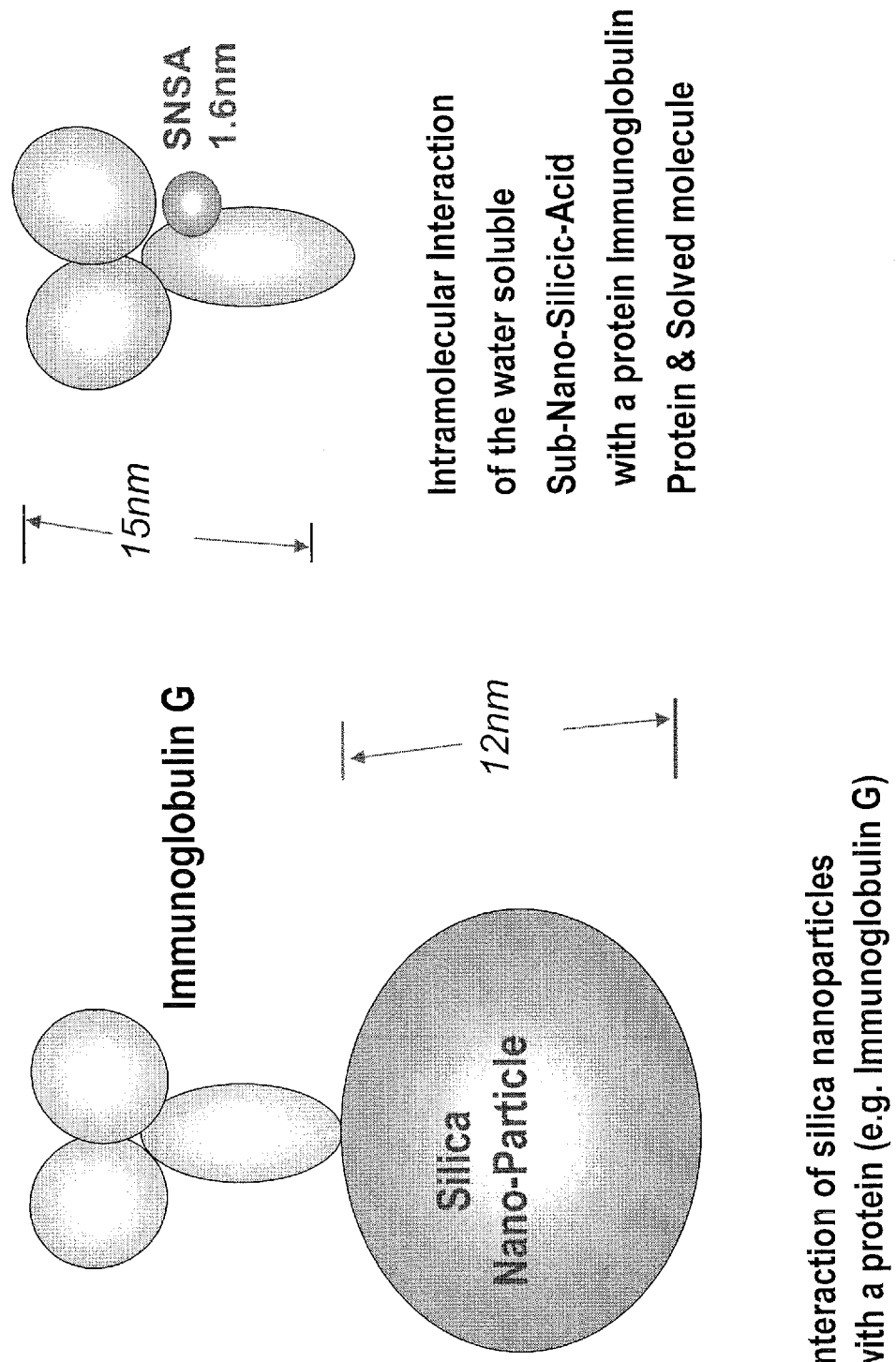

With their preferred molecular diameter ϕ≤3 nm the condensed silicic acids of the invention are significantly smaller than almost all proteins. Interaction of SNSA with a larger protein molecule may be classified as intra-molecular, e.g. if SNSA bonds to a defined internal domain of the protein or bridge two or more domains within the same molecule. Another preferred embodiment is the SNSA molecule interacting "inter-molecularly" e.g. by bridging together two similar or different protein molecules. Both preferred embodiments are a significant technical progress in comparison with the previous art interaction of proteins with large ($\phi$>10 nm) silica nano-particle as solid carriers as illustrated by FIG. 10. In dimension the inventive substance with $\phi$<5 nm is generally smaller than the proteins with which it interacts. Accordingly the substance SNSA will be involved rather in some intra-molecular interactions, with or between some well defined structural domains of the protein. This inventive mode of interaction comprises an obvious technical progress in comparison with prior art interaction of silica nano-particles with proteins.

The small spheroidal form with compact internal core and highest density of free Si—OH bonds on the external shell provides the basic prerequisite for the inventive interaction with proteins or other bio-molecules. FIG. 8 illustrates the assumed interaction of the inventive molecule with the domain-P and domain-N of the P-type ATPases.

Prior art vanadates able to interact with proteins involved in reversible phosphorylation silica nano particles applied to interact with proteins are classified as carriers since their dimension $\phi$>>5 nm is comparable but usually much higher than simple proteins dimensions which exclude their intra-molecular Human carbonic anhydrase III (hCA III), which is the most stable of the protein variants, establishes a dynamic equilibrium between bound and unbound protein following mixture with silica particles.

Na,K-ATPase

The here disclosed sub-nano-silicic acids SNSA were identified as potent inorganic inhibitors of Na,K-ATPase and several type II P-type ATPases in the sub-micromolar range. SNSA factors were found to bind to the intracellular side of the Na,K-ATPase and the inhibition is not competitive with ouabain binding. The inventive mechanism of interaction of the sub-nano-silicic acid with the protein domains "N" (nucleotide binding) and domain "P" (phosphate binding) is illustrated in FIG. 8. The inventive SNSA interacts with the Na,K-ATPase in the E1 conformation of the ion pump and induces a conformational rearrangement that causes a change of the equilibrium dissociation constant for one of the first two intracellular cation binding sites. The mechanism of intervention of the inventive SNSA with the phosphorylation cycle of the Na,K-aTPase is illustrated in FIG. 9. The MCS inhibited state was found to have bound one cation ($H^+$, $Na^+$ or $K^+$) in one of the two unspecific binding sites, and at high $Na^+$ concentrations another $Na^+$ ion was bound to the highly Na+-selective ion-binding site.

Ca-ATPase

The inventive substance SNSA inhibits the Ca-ATPase pump of the endoplasmic reticulum (SERCA) with $IC_{50}$ ~50-80 nM. This provides a significant progress in comparison with previous art SERCA inhibitors in the micromolar (μM) range like: cyclopiazonic acid, 2,5-di-(tert-butyl)-1,4-benzohydroquinone (tBuBHQ) or the cyclo-oxygenase-2 inhibitor celecoxib, curcumin and melittin. Although the inventive silicic acid is less potent than the previous art SERCA inhibitor thapsigargin ($IC_{50}$ in sub-nano-molar range) the here disclosed SNSA provides the advantage of its 1000 fold lower acute toxicity.

Inhibition of SR Ca-ATPase by the SNSA is similarly due to the interaction of the inventive agent with the protein domains However, when fitted with a Hill function, the Hill coefficient, $n_H$=2.56, was significantly higher than in the case of the Na,K-ATPases which indicates that a different inhibitory mechanism may occur.

Differences to the mechanism of the sodium pump inhibition may arise from the small but significant interaction of the inventive SNSA with the involved alkali ions.

H-ATPase

The inventive substance SNSA inhibits the gastric $H^+/K^+$-ATPase (gastric proton pump) with a potency of $IC_{50}$ ~80 nM. This enzyme is concentrated in parietal cells from where it secretes $H^+$ into the lumen of gastric glands in electroneutral exchange. The inventive silicic acid SNSA is disclosed as a reversible $H^+/K^+$-ATPase inhibitor with a high potency which makes it a hot anti-acid drug candidate. Its pharmacological action, by reversible interaction with the membrane pump makes it able to reduce gastric acidity after binding to the target protein. This represents an important technical progress in comparison with prior art synthetic proton pump inhibitors (PPI), e.g. omeprazole, a substituted benzimidazole that reacts covalently with the enzyme and especially that which binds reversibly and noncovalently to the enzyme.

Inhibition of Protein Phosphatases PTEN

The here disclosed sub-nanosilicic acid SNSA inhibits the tumour suppressor PTEN (phosphatase and tensin homologue deleted on chromosome 10). This is a tyrosine phosphatase with dual activity, dephosphorylating both protein and lipid substrates. It has high specificity towards 3-phosphorylated phosphoinositides (PI) e.g. PtdIns(3)P, PtdIns(3,4)P2 and PtdIns(3,4,5)P3. By reducing the intracellular PtdIns(3,4,5)P3 level, PTEN counteracts the PI3K, thereby terminating certain downstream signalling pathways leading to apoptosis.

One effector of PI3K/PTEN signalling responsible for some of those effects is protein kinase B (PKB/Akt), a mammalian homologue of the viral oncoprotein v-akt. PKB is recruited to the plasma membrane in response to growth factor stimulation via the binding of PI(3,4,5)P3 to its PH domain which leads to its phosphorylation. PKB contains two distinct sites, threonine-308 (T308) and serine-473 (S473) that are phosphorylated by kinases which in turn are activated by PI(3,4,5)P3. The phosphorylation of PKB is susceptible to PI3K-inhibitors such as LY294002 and Wortmannin. On the other hand, PTEN-inhibiting compounds result in increased PKB phosphorylation.

As disclosed in the examples 120 μg/ml of SNSA leads to an up-regulation of PKB phosphorylation which may be explained as an inhibitory effect on the protein phosphatases PTEN. The effect is very similar to that provided by vanadates with the essential advantage of the significantly lower toxicity of the inventive agent.

Biological Assay of SNSA

The here disclosed biologically active sub-nano silicic acid SNSA shows a specific, dose dependent interference with the reaction between Immunoglobulins such as human IgG and Protein A. This very surprising reaction is demonstrated by the ELISA technique on plates coated with IgG protein in a concentration of 0.2 to 4 μg/ml. Treating these plates with Protein A coupled with alkaline phosphatase and stained after the PBS-Tween washing with PDNP the developed colour at 405 nm shows constant optical density (OD) values considered as control.

Treating the IgG coated and washed plates with increasing amount of SNSA for 1 h followed by the same procedure as by control (washing, saturation with BSA, treatment with Protein A etc. resulted in a dose dependent increase of the measured optical density value as illustrated by attached examples. The enhancement is linear in the 10-300 ng/ml domain which offers a suitable method for sensitive assay of the inventive SNSA substance including in biological fluids 5.5 Therapy Applications It was found that the inventive substances and the pharmaceutical formulations containing the inventive substances are highly useful as pharmaceutically active agents or ingredients and can be used for medical treatment, prophylaxis and diagnosis in the field of medicine.

Moreover the substances of general formula (I) are useful for inhibiting-type ATPases, especially of Na,K-ATPase, Ca-ATPase or H/K-ATPase or modulating the activity of kinases and phosphatases such as the Protein Kinase B/PTEN system. Furthermore remarked is the activity of the substance of general formula (I) on ATP-bonding cassette proteins essentially involved in enhanced resistance developed by organisms again drugs such as antibiotics and cytostatics which is a serious concern of current medicine.

These activities makes the inventive substances highly potential drugs and diagnostic compounds for treatment of hypertension, diabetes, bone diseases, cardiovascular diseases, neurodegenerative pathologies, cancer, hyperacidity, osteoporosis, dental calculus, Alzheimer disease, Creutzfeld-Jacob, wound healing.

Moreover the inventive substances are useful for appetite control, wound healing and for prophylaxis of hypertension, diabetes, bone diseases, cardiovascular diseases, neurodegenerative pathologies, cancer, hyperacidity and osteoporosis as well as for the preparation of a composition for diagnosis of hypertension, diabetes, bone diseases, cardiovascular diseases, neurodegenerative pathologies and diseases, cancer and hyperacidity.

Hyperacidity

Substances of this invention are very potent non-toxic inhibitors of the H/K-ATPase providing $IC_{50}=0.8$ µg/ml corresponding to submicromolar range. SNSA was found to reduce gastric acid secretion response due to 4-methylhistamine. The inventive substances SNSA are active by oral and parenteral administration in mammals such as rats and dogs throughout a dosage range of 0.01-25 mg/kg. The inventive substances acts not by anticholinergic mechanism thus side effects of current anti-acid drugs such as dryness of mouth and blurred vision are not expected. Substances of the present invention are therefore useful in management and treatment of gastric hyperacidity.

Gastro esophageal reflux disorder (GERD) is a frequent pathology connected to meals which manifests when the lower esophageal sphincter does not remain closed and acid from the stomach can reflux or flow back into the esophagus. Though the root causes are often unclear, perhaps the most prevalent acid reflux cause is by overproduction of gastric acid. Intake of the inventive sub-nano silicic acid SNSA preferably after meals in amounts of 0.1-80 mg/kg body weight reduces very efficaciously the manifestation of gastric reflux disorders (GERD).

Hypertension,

Hypertension is a major therapeutic challenge to health care providers. It is a major risk factor for cardiovascular morbidity, heart failure, heart attack, stroke, and kidney failure. Anti-hypertensive therapy is effective in reducing or eliminating the increased morbidity/mortality associated with hypertension.

The instant silicic acid substances are disclosed to have a definite therapeutic potential to treat essential hypertension. Their primary target of intervention in the pathophysiology of hypertension the Na,K-ATPases, at cardio-vascular and renal level, or on further, up to now less identified targets.

According to experimental observations SNSA enhances the urinary excretion of Na+ inhibiting the renal sodium pump which restores Na ions in the plasma. By inhibition of the renal Na,K-ATPase by hypertensive patients and the subsequent diuresis helps to restore the normal plasma volume and blood pressure.

Parallel inhibition of the Na,K-ATPases of the blood vessels and the heart respectively may lead to a hypertensive effect which may compete the hypotensive effect by natriuresis and diuresis.

Silicic acids of the present invention are disclosed to reduce the arterial blood pressure in hypertensive rats which leads to the conclusion that they act selectively on the renal Na,K-ATPases as on the blood vessel or criac sodium pumps.

Diabetes

Insulin binds to a receptor on the plasma membrane of target cells, and when this insulin-receptor complex forms glucose is allowed to enter into the target cell where it is used as an energy source or is converted into glycogen for energy storage. The insulin receptor is a protein consisting of two copies of two different peptide units, alpha and beta. One insulin molecule is required to bind to each alpha subunit, and after this occurs, the β subunits then transmit a signal that causes the cytoplasmic end of the receptor protein to change shape. This change causes a cytoplasmic protein kinase active site to be exposed which causes the phosphorylation of an insulin receptor substrate which initiates other reactions that lead to the uptake of glucose by the cell.

Administration of the inventive substance to diabetic mice db/revealed its remarkable anti-diabetic potential. Testing was performed in comparison with the bis-L-Glutamin-Vanadate complexes VGlu2 and the therapeutically used diabetes drug Rosglitazone. Silicic acid derivative SNSA according the invention produced a significant reduction of the glucose level similarly to the diabetes-drug Rosglitazone and of the used Vanadium-Glutamate complex VGlu2. These data demonstrated that the inventive substance could have an advantage over the inorganic salts as potential anti-diabetic agents.

Possible mechanism of SNSA may be the insulin-mimetic action by interaction with the Insulin receptor (IR) as suggested by the attached examples. This may involve inhibition of the phosphotyrosine phosphatase PTP1B coupled to the insulin receptor. This phosphatase reduces the degree of phosphorylation of the insulin receptor which decreases insulin signalling and insulin sensitivity. Inhibition of PTP1B mimics the effects of insulin Appetite Control The inventive silicic acid was found to reduce the food intake of experimental animals (rats) in comparison with control. The mechanism of action of the observed physiological effects can be that SNSA reduces the production of ghrellin in stomach. Alternatively the biological active SNSA may influence the AMP-dependent protein kinase (AMPK) which is a key signalling component in the ghrelin-NPY pathway. Modulation of this or of one of the coupled phosphatases involved in regulating of these signalling pathways is suggested to be the target of this novel therapeutic strategy to control appetite very efficiently.

Overall, the results of animal experiments with the inventive silicic acid indicate that it provides a very promising strategy to both improve glucose tolerance and promote weight loss, a potential advantage over most other current drugs for type 2 diabetes which promote weight gain.

Cancer

Sub-Nano-condensed silicic acid of the invention is remarked by its low level toxicity manifested in vitro on cell cultures of various type. The viability of Jurkat cells, human and murine T-lymphocytes, dendritic cells and macrophages is not significantly altered by SNSA in up to 50 µMolar concentration.

Cancer cells in culture react in different manner with the inventive SNSA substance. Standard HeLa or mouse MP cells were inhibited with IC50 values in the range of 0.1 to 20 Mol range.

Previous studies have shown that agents that increase intracellular free $Ca^{2+}$ ($Ca_i$) levels can activate apoptosis even in androgen-independent metastatic prostate cancer cells. Here disclosed SNSA is a potent inhibitor of a calcium ATPase pump that is crucial for maintaining calcium homeostasis and as such can induce apoptosis in all cell types. Whereas the volume of the tumours in the control mice grew by 165% over 12 days, the tumours in the SNSA-treated mice were reduced to 45% of their original volume.

Protein phosphatases such as Protein-Tyrosine-Phosphatases (PTPs) can have both inhibitory and stimulatory effects on cancer-associated signalling processes. Moreover protein phosphatases have very important roles in regulation of the adhesion, vascular transport, spreading and metastasis of cancer cells. Better understanding of these processes could identify novel therapeutic targets. Sub-nano-silicic acid of the invention was found to reduce efficiently the branching and spreading of aggressive cancer cells. This should offer novel therapeutic approaches to prevent and control cancer-metastasis with all its fatal consequences Drug Efflux Pump Here disclosed silicic acids SNSS inhibit very efficiently ATP-driven multi-drug efflux pumps such as the P-glyco-protein. This was confirmed in vitro by assessing the exclusion of fluorescent dyes from cancer cells with over-expressed efflux pumps. Efficient inhibition of efflux pumps makes the inventive substances suitable for application in chemo-therapy of cancer, to reduce the acquired resistance to cytotoxic agents which is a major concern. The mechanisms underlying the resistance appear to take advantage of functions involved in the control of cell homeostasis. The over-expression of P-glycoprotein, a plasma membrane drug efflux transporter that belongs to the ATP binding-cassette transporter family, represents one major mechanism by which tumors become multidrug resistant.

The pH gradient between the cytoplasm and intracellular organelles may be also involved in resistance to antitumor drugs. The suggested mechanisms are drug sequestration and neutralization in acidic organelles or in the acidic extracellular environment. Increased turnover of acidic vesicles may represent an additional important feature of the mechanism for chemo-resistance, both in cells over-expressing multidrug efflux transporters such as P-glycoprotein and in cells that do not express these efflux transporters. The involvement of acidic vesicles in resistance to cytotoxic drugs includes both an increased acidification of lysosomal-type vesicles, leading to sequestration of drugs in acidic organelles, and drug extrusion from the cell through a secretory pathway.

Osteoporosis, Dental Calculus

Silicic acids of the invention may act as a substrate for silica mineralization including hydroxyapatite nucleation. This finding opens the application of the inventive SNSA to promote the bone rebuilding and including formation of dental calculus.

Alzheimer by Aluminium Antagonism

A preferred embodiment of the inventive substance is to prevent the unwanted aggregation of proteins involved in pathologies like the formation of the amyloid-plaques in Alzheimer disease or prion aggregation in the Creutzfeld-Jakob disease. The element aluminium (Al) and it salts were identified as a neurotoxin and considered as one of the possible causal factors contributing to Alzheimer's disease. Daily intake of the inventive sub-nano-silicic acid SNSA in amounts of 0.1-15 mg/kg body weight was able to reduce in animal studies the uptake of Aluminium in the digestive tract and thus to slow the accumulation of this metal in the body, brain tissue included. Consumption of SNSA per oral intake reduced significantly (p=0.021) the urinary excretion of aluminium (87.0 to 54.2 nmol/mmol creatinine). The reduction in urinary aluminium supported the future longer-term use of the inventive silicic acid as non-invasive therapy for reducing the body burden of aluminium in Alzheimer's disease. These results confirmed that the here disclosed SNSA is a suitable bio-available form of nutritional supplementation of silicon affording a protective factor for preventing and curing neurodegenerative pathologies such as Alzheimer's or Creutzfeld-Jakob disease.

Wound Healing

Several growth factors, like epidermal growth factor (EGF), play an important role in wound healing by binding to growth factor receptors and changing their structure. These changes activate protein-kinases which causes the phosphorylation of many intracellular proteins like PI3Kinase (PI3K).

The inventive substances SNSA proved to improve the activity of the PI3 Kinases mostly by inhibiting of the conjugate phosphatases. This may allow to apply the here disclosed silicic acid SNSA to promote wound healing which is an unmet medical need.

5.6 Pharmaceutical Formulations

Here disclosed inventive applications in therapy and prevention of the silicic acid SNSA requires to provide it in stable pharmaceutical forms. Preferred embodiments of the present invention use SNSA on inert support materials which may be of inorganic or organic nature. Preferred materials are the pharmaceutically approved excipients like certain aliphatic polyols (such as mannitol, sorbitol, xylitol, pentaerythritol and threitol), sugar, starch or the like.

Suitable supports of the inventive application of the here disclosed silicic acid SNSA include sugars such as lactose, sucrose, mannitol and sorbitol, starches derived from wheat, corn rice and potato, and celluloses such as microcrystalline cellulose. The amount of supports in the composition can range from about 5 to about 95% by weight of the total composition, preferably from about 25 to about 75%, more preferably from about 30 to about 60% by weight, and most preferably from about 40 to 50% by weight.

Other inventive pharmaceutical formulations are based on the conjugates formed by the inventive substance SNSA with organic nitrogen containing compounds like amino-acids, amino sugars or amino-alcohols.

The compounds of the general formula (I) can also be administered in form of their pharmaceutically active salts optionally using substantially nontoxic pharmaceutically acceptable carrier, excipients, adjuvants or diluents. The medications of the present invention are prepared in a conventional solid or liquid carrier or diluents and a conventional pharmaceutically-made adjuvant at suitable dosage level in a known way. The preferred preparations and formulations are in administrable form which is suitable for oral application or via dermal or transdermal patch. These administrable forms, for example, include pills, tablets, film tablets, coated tablets, capsules, powders and deposits. Other oral administrable forms are also possible.

The inventive silicic acid substances or pharmaceutical preparations or formulations containing said substances may be administered by any appropriate means, including but not limited to inhalation, injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrically, intracutaneously, intravaginally, intravasally, intranasally, intrabuccally, percutaneously, sublingually, or any other means available within the pharmaceutical arts.

Within the disclosed methods the pharmaceutical compositions of the present invention, containing at least one substances of the general formula (I) or pharmaceutically acceptable salts thereof as an active ingredient will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active ingredient may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants that may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby is solidified.

Also included are solid form preparations which are intended to be converted, shortly before use, to liquid form preparations for either oral or parenteral administration. Such liquid forms include solutions, suspensions and emulsions.

One preferred form is a dermal or transdermal patch. The substances of the present invention may also be deliverable transdermally. The transdermal compositions may take the form of creams, lotions, aerosols and/or emulsions and can be included in a transdermal patch of the matrix or reservoir type as are conventional in the art for this purpose.

Suitable solvents for the inventive patch may be selected form purified water; ketones such as acetone, butanone, 2-pentanone, 3-pentanone; alcohols such as ethanol, propanol, isopropanol, butanol, isobutanol, sec.-butanol, tert.-butanol; esters such as acetic acid ethyl ester, acetic acid propyl ester and the like. Furthermore, mixtures of said solvents can also be used. Suitable co-solvents may be used together with the above-mentioned solvents or mixtures of solvents, said co-solvents may be selected from the group comprising lactic acid, salicylic acid, succinic acid, urea, Miglyor® 812 (Chemische Werke HOIs, Marl, Germany), triglycerides, ethyloleate, glycerylmonododecanoate, olein, oleate, Macrogol® 6000, and lecithin.

If present, the amount of solvents or the total amount of solvents and co-solvents in the adhesive can range from about 0.5 to 70% by weight of the adhesive, preferably from about 3 to about 60% by weight of the adhesive, more preferably from about 10 to about 50% by weight, even more preferably from about 20 to about 40% by weight, and most preferably from about 10 to about 30% by weight of the adhesive.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refer to the active ingredients dispersed or solubilised in a hydrophilic semi-solid matrix.

Powders for constitution refers to powder blends containing the active ingredients and suitable diluents which can be suspended in water or juices.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent.

Techniques for the formulation and administration of the inventive substances according to general formula (I) of the present invention may be found in "Remington's Pharmaceutical Sciences" Mack Publishing Co., Easton Pa. A suitable composition comprising at least one substance of the invention and/or pharmaceutically acceptable salts thereof may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

SNSA Improves the Efficacy of Protein Based Therapeutics

Therapeutic proteins conquered an important volume of the pharmaceutical market particularly in the antirheumatic and anti-cancer therapy domains. Their highly specific biological activity and the sharply defined therapeutic profile comprise major advantages in comparison to non-proteic drug substances. However protein drugs are bound inherently to major disadvantages which result from their biochemical nature. Small molar mass proteins such us oligo- or polypeptides have a reduced bioavailability since they are rapidly decomposed by the enzymatic network of the living organisms. Application of large molar mass proteins such us the protein based anti-rheumatic drugs is associated with enhanced frequency of infections and malignancy. Major detriment of protein based cancer therapeutics resides in their own immunogenicity i.e. they induce the production of anti-antibodies by the host organism which annihilate progressively the efficiency of a protein drug.

By its inventive interaction with peptides and proteins sub-nano-silicic acids are able according to the invention to modify substantially the structure and properties of several peptides and proteins. These interactions can influence significantly the bioavailability and biodegradation of therapeutic proteins with practical advantages in their medicinal applications.

Inventive applications of SNSA to improve the efficacy of protein therapeutics include but not exhaust combinations of SNSA with small polypeptides such as insulin, vaso-intestinal-peptide (VIP) or with monoclonal antibody based drugs such as: Abatacept, Adalimumab, Certolizumab, Etanercept, Golimumab, Infliximab in antirheumatic therapy or with anticancer drugs such as Cetuximab, Gemtuzumab, Herceptin, Ibritumomab or Rituximab.

SNSA as Nutritional Supplement for the Trace Element Silicon

Silicon is ubiquitous throughout biological systems with concentrations in the range of (0.05-3.5%) in living organisms. Various forms of silica, the combinations of Si an 0 are essential components of the solid structure of several algae sponges and plants. Silica has an essential role in animals during connective tissue synthesis and bone crystallization but the mechanism is less understood. The daily intake of silica by normal nutrition of man is approx. 20-50 mg Si and the same amount is eliminated in 24 h predominantly by urine. Principal sources of nutritional silicon are plants which contain and water and other beverages.

The decreased ability of elderly persons to assimilate silicon is tentatively correlated with their enhanced frequency to contract bone and connective tissue diseases. Although a clinical silicon deficiency has not yet been demonstrated in human the deficient ability of elderly organisms to assimilate silicon from nutrition is thoroughly demonstrated. The inventory sub-nano-silicic acid (SNSA) provides a natural silicic acid with excellent bioavailability since it diffuses across cell membranes and in most cell types the intracellular concentration equilibrates the extra-cellular environment.

6 BRIEF DESCRIPTION OF THE DRAWINGS

FIG. 1 Chemical structure of prior-art described: linear, branched cyclic, multi-cyclic cage-type condensed oligomeric derivatives of silicic acid FIG. 2 Scheme of the polymerization (polycondensation) of ortho-silicic acid which produces the unstable low molar mass oligomers and the water soluble higher oligomers which are rapidly transformed in solid particles or amorphous polymers (silicagel).

FIG. 3 Structural embodiment of the inventive substance with inner core constituted predominantly by $Q^4$ Si atoms and with outer shell(s) constituted by $Q^3$ and $Q^2$ type Si atoms and adjacent —OH groups.

FIG. 4. Dimensional overview on the whole field of condensed silicic acid derivatives with localization of SNSA in the range between low molar mass silicic acid species and the large >5 nm silica-particles.

FIG. 5 Spheroidal shape of the inventive sub-nano-silicic acid SNSA structure shown by a space-filled molecular model corresponding to an internal diameter of 1.45 nm.

FIG. 6 Scheme of the construction of inner shell of the inventive SNSA molecule starting with a cyclo-tetra silicic acid units. The first two layers contains 4+8=12 $Q^4$ type Si atoms forming a geometrical progression. which may be completed by altogether 24 ($Q^4+Q^3$) Si atoms.

Figure 7:
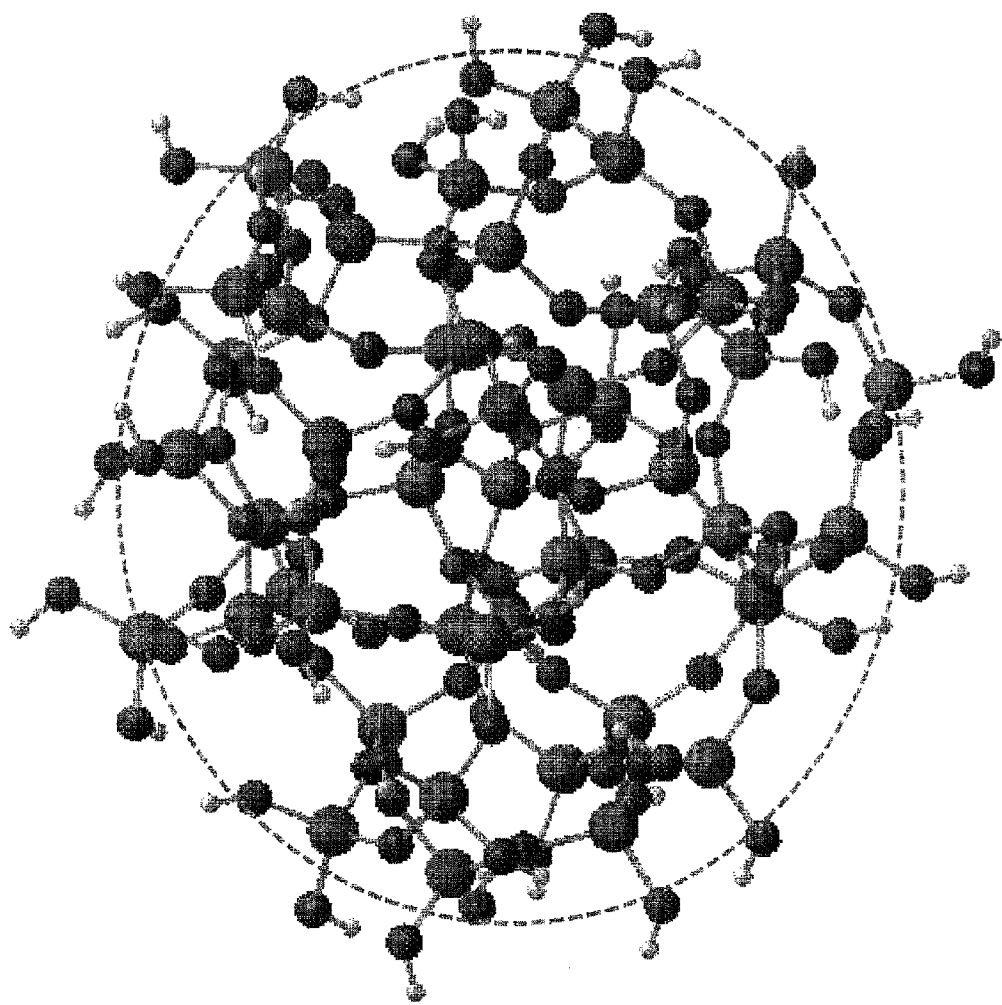

FIG. 7 The ball-stick model of a representative sub-nano-silicic acid molecule according to the invention illustrates the, equalized distribution of the Si—OH groups on the external surface of the spheroid. The Q3 and Q2 type Si atoms and the adjacent —OH groups are randomly distributed but statistically equalized, i.e. without any preference of selective spatial grouping.

FIG. 8 Inventive mechanism of the interaction of the silicic acid SNSA with the nucleotide (N) and phosphate-binding (P) domains of the ATPase Protein FIG. 9 Involvement of the inventive sub-nano-silicic acid SNSA (with diameter of 1.6 nm) in the intramolecular interaction within domains of the CA III protein (29 kDa)

FIG. 10 Comparison of the prior art interacrion of a silica nanoparticle with diameter of 12 nm and human Immunoglobulin IgG with the inventive interaction of SNSA and IgG.

Figure 12:
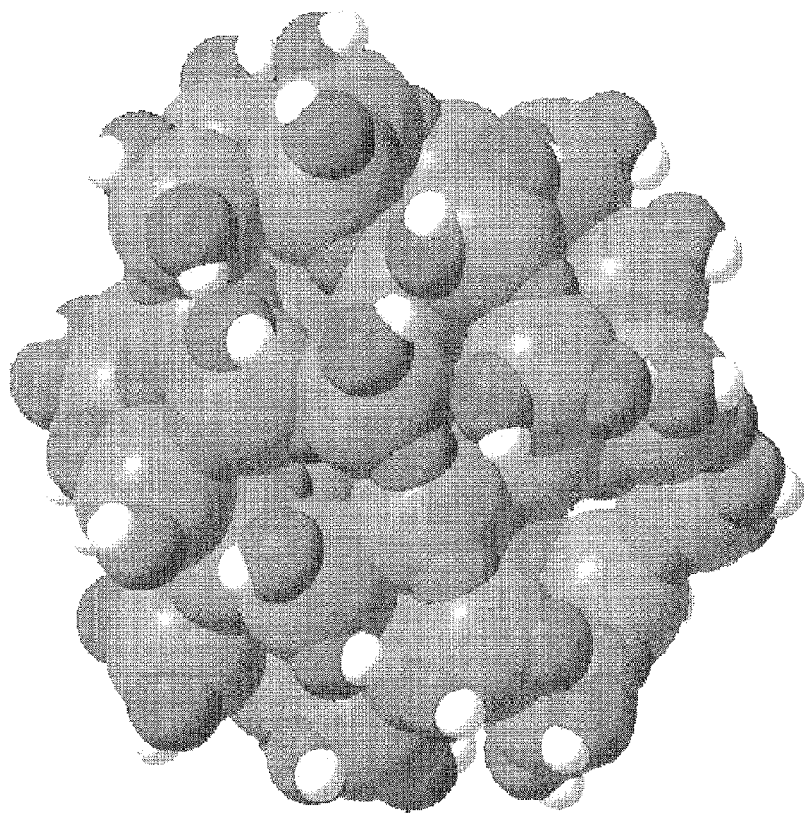
Figure 13:
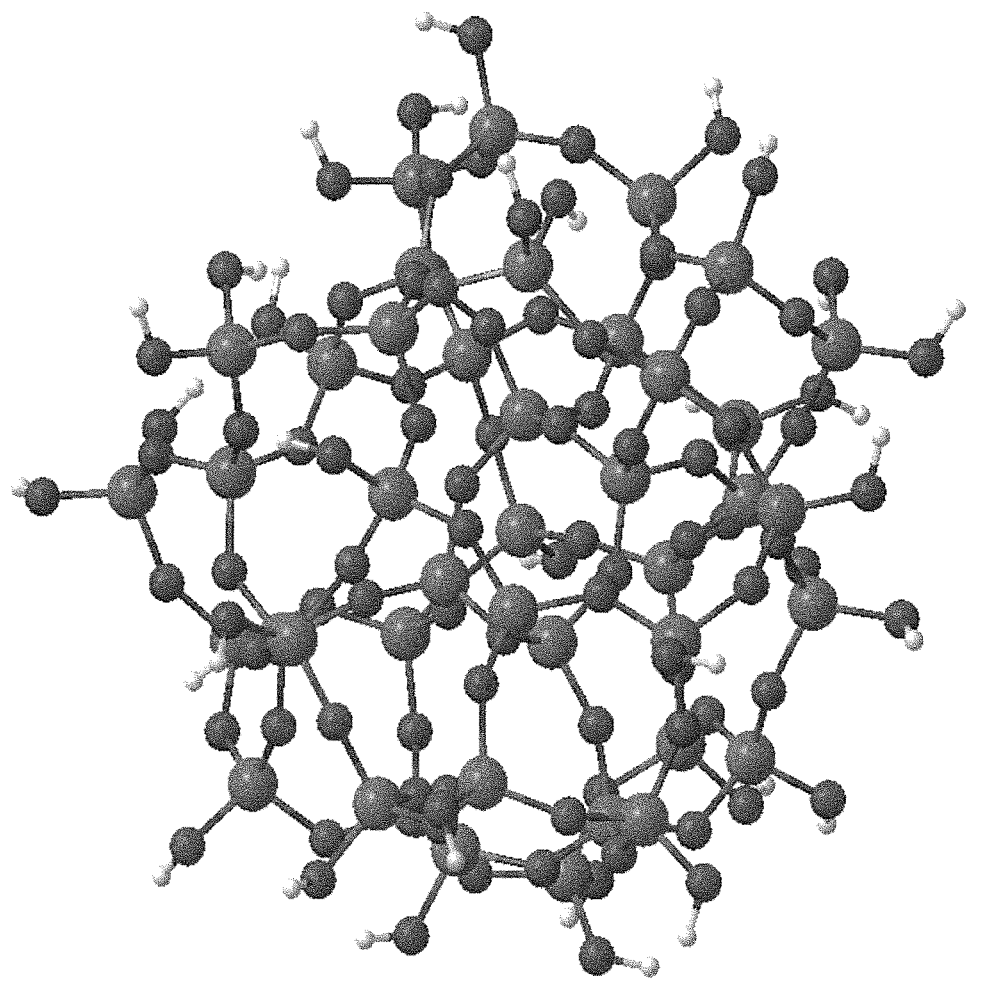
Figure 14:
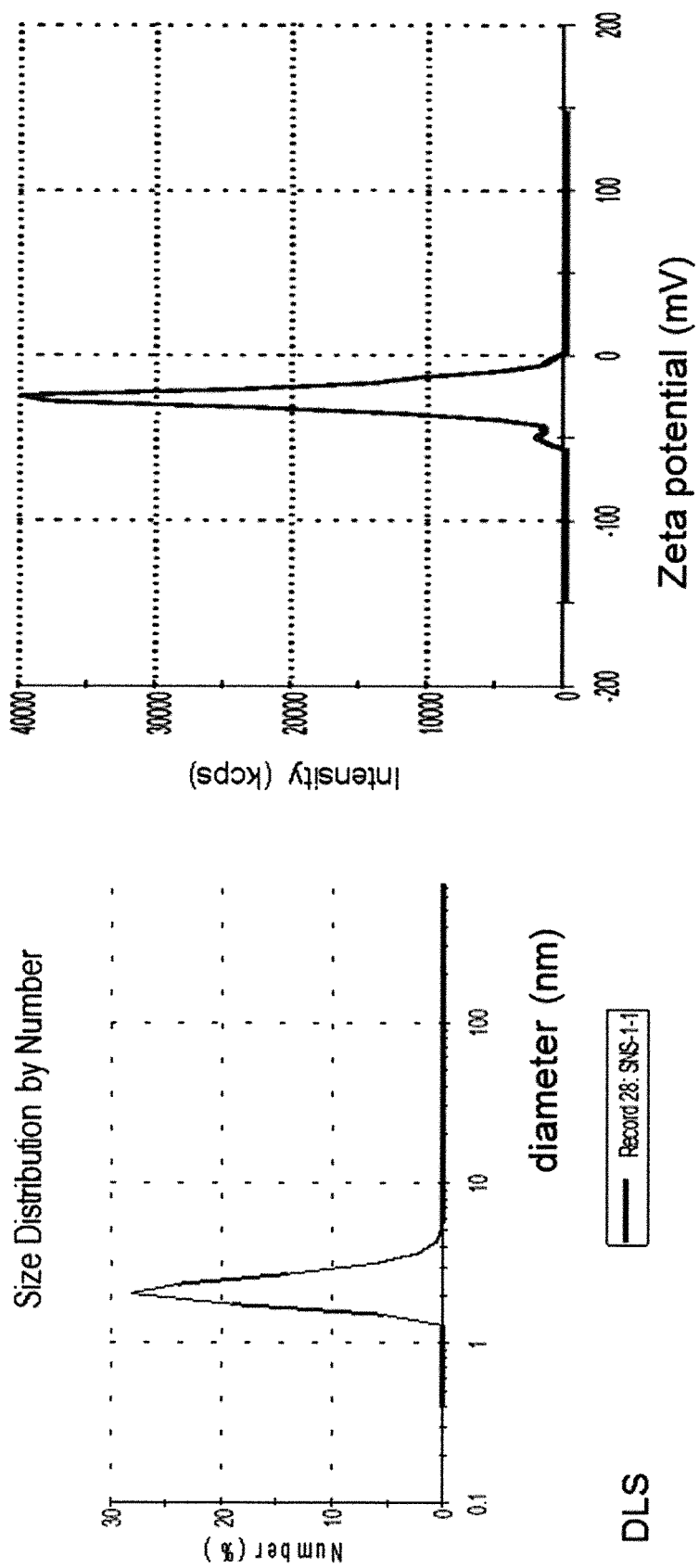

FIG. 11 Structural formula shown by stick-ball model of the inventive sub-nano-silicic acid with formula $Si_{36}O_{90}H_{36}$ FIG. 12 Molecular shape shown by space-fill model for the inventive silicic acid SNSA with formula $Si_{45}O_{115}H_{46}$ FIG. 13 Molecular structure shown by a ball-stick model of the inventive sub-nano-silicic acid with formula $Si_{42}O_{100}H_{32}$ FIG. 14 Dynamic Light scattering DLS diagram and Zeta potential of the SNSA b-118 with diameter 2.2 nm and corresponding to molar mass 6.2 kDA.

Figure 15:
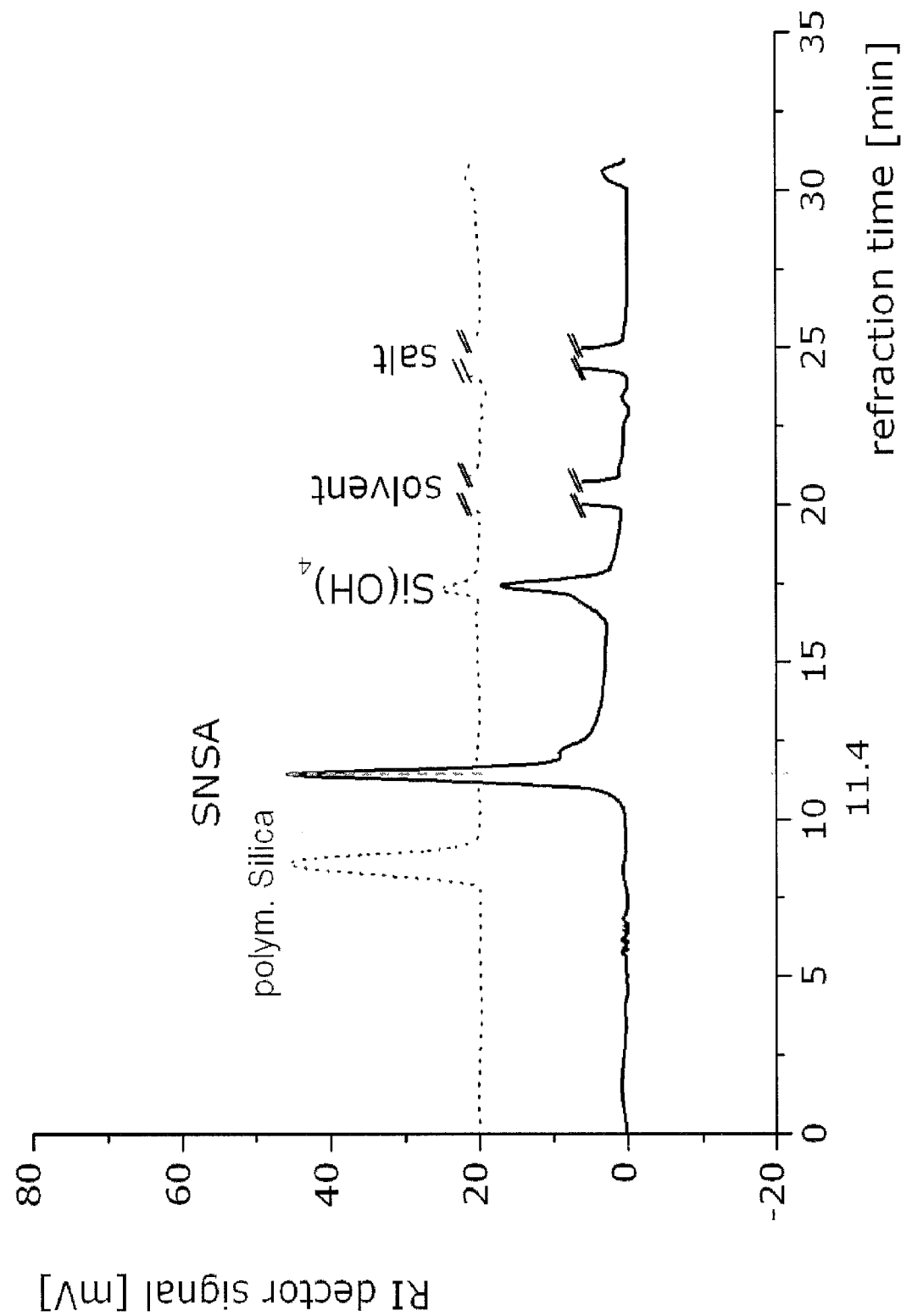
Figure 16:
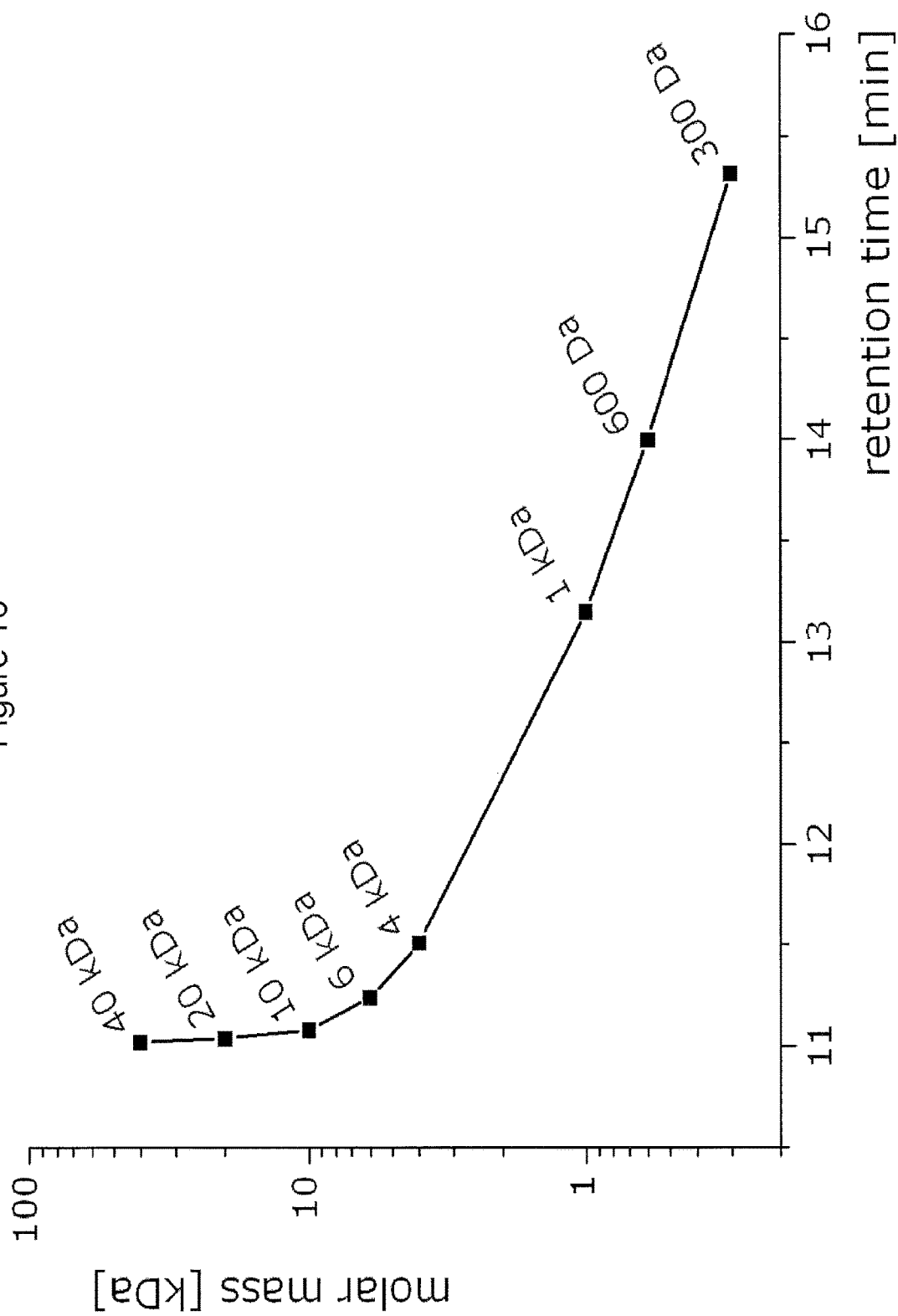
Figure 17:
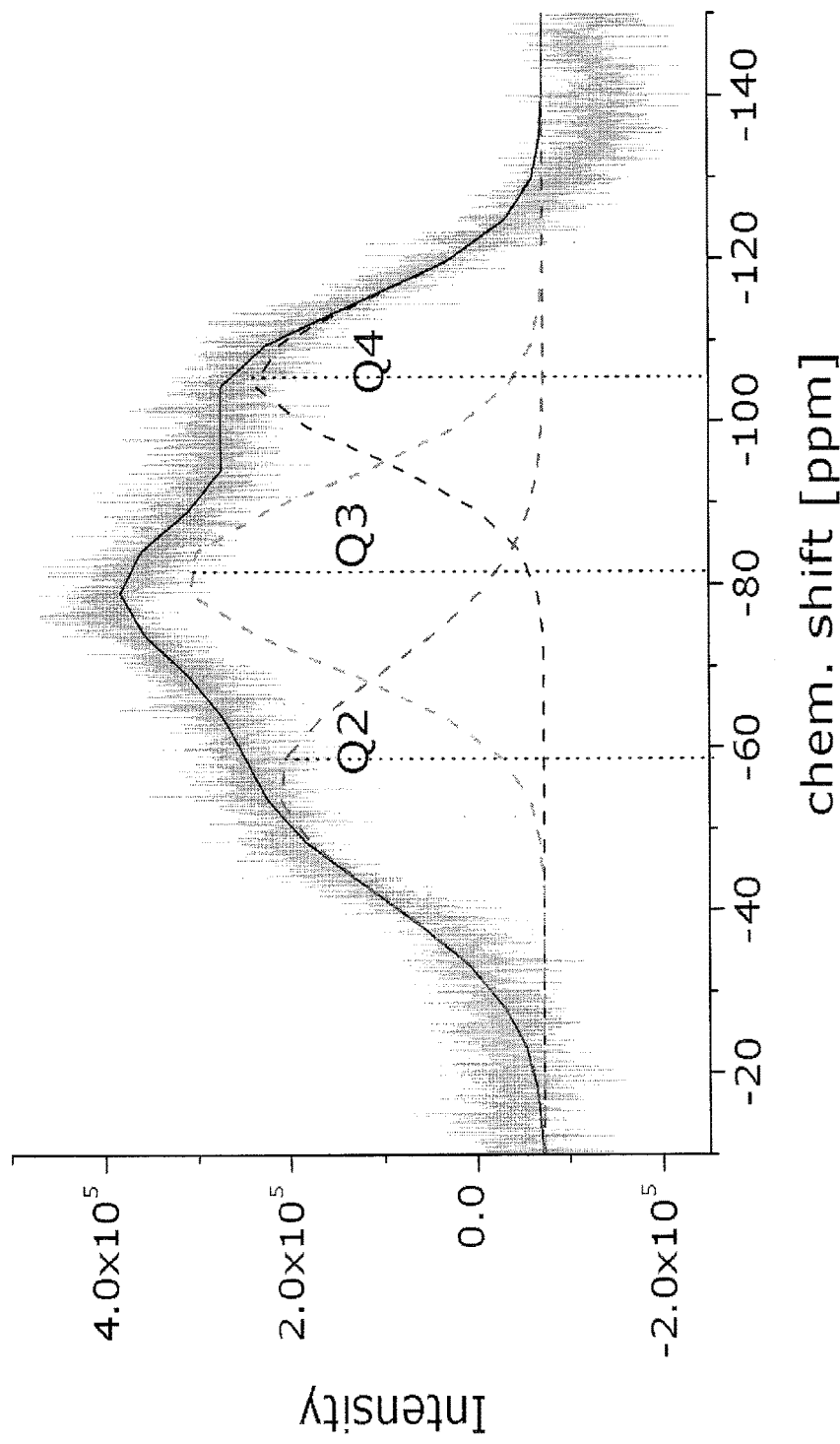
Figure 18:
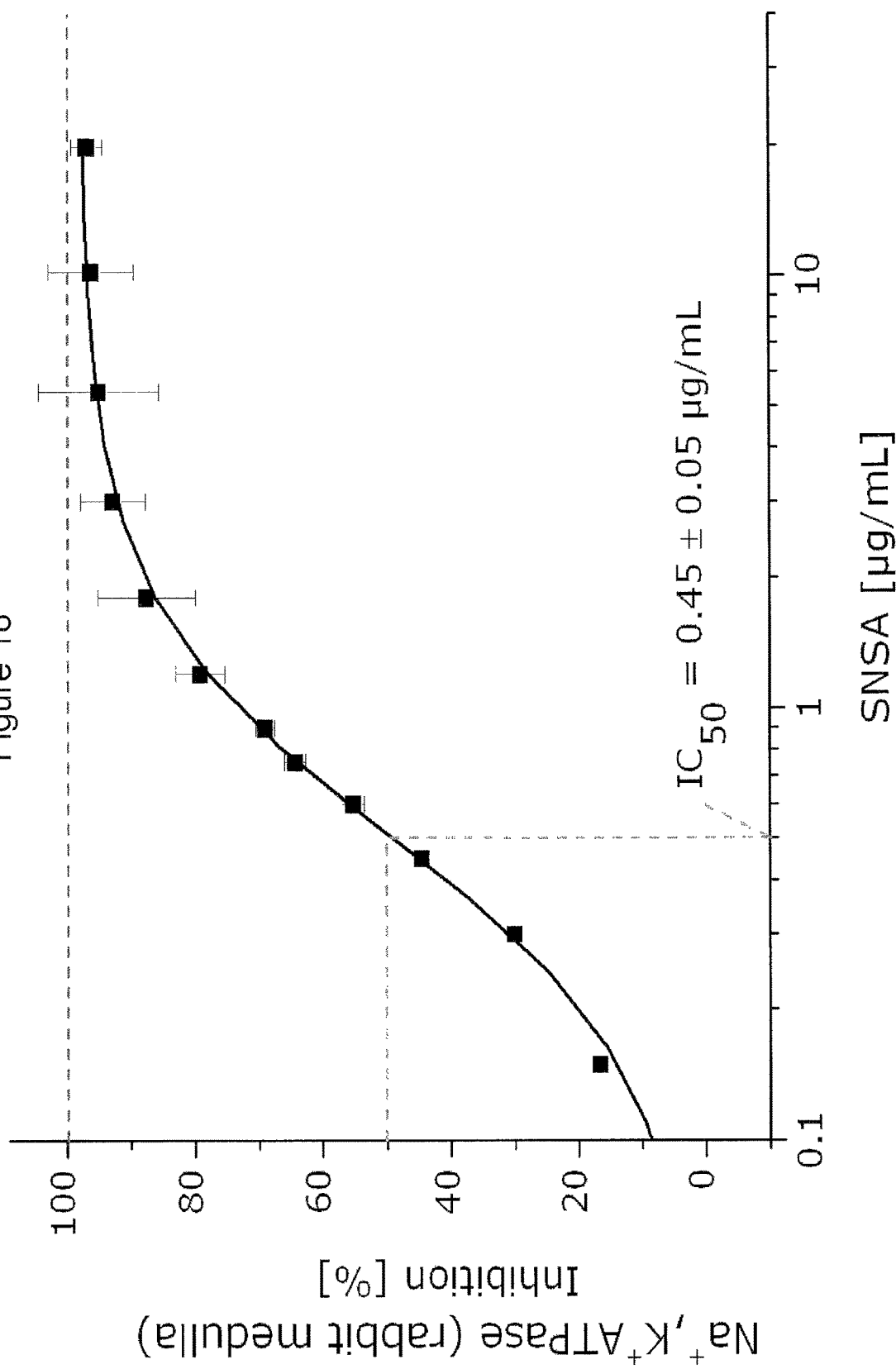

FIG. 15 Size Exclusion Chromatography diagram of SNSA (b-101) with molar mass of 4.2 kDa deduced form the standard curve value FIG. 16 Size Exclusion Chromatography Standard curve with PEG standards FIG. 17 The $^{29}$Si NMR spectrum of the inventive silicic acid SNSA (b101) in water recorded in a PTE nmr tube FIG. 18 Concentration dependent inhibition of the rabbit medula $Na^+,K^+$-ATPase by SNSA (b-118) with determination of the half-inhibition (IC50) value.

Figure 19:
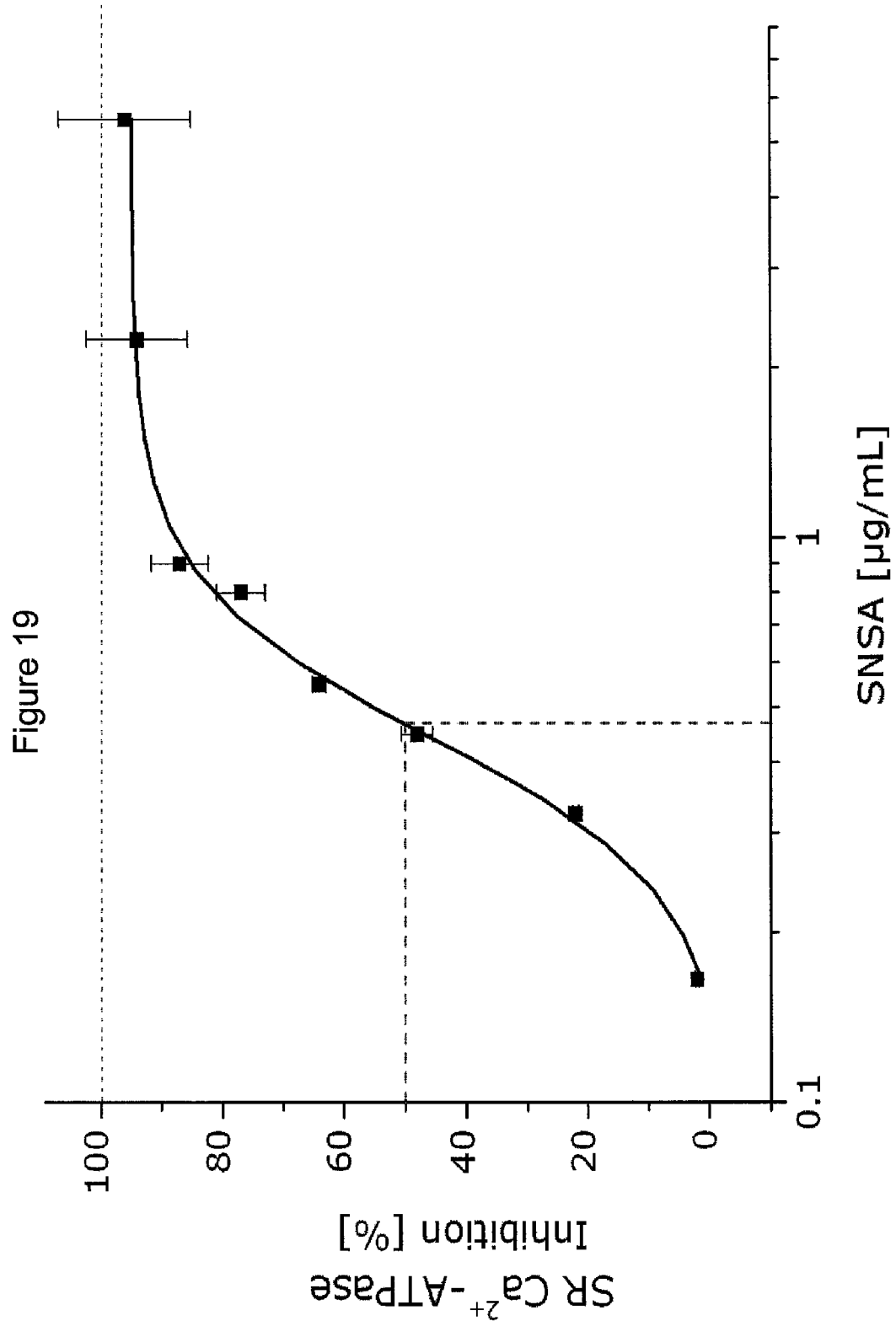

FIG. 19 Concentration dependent inhibition of SR $Ca^{2+}$-ATPase by SNS b-101 with determination of the half-inhibition (IC50) value.

Figure 20:
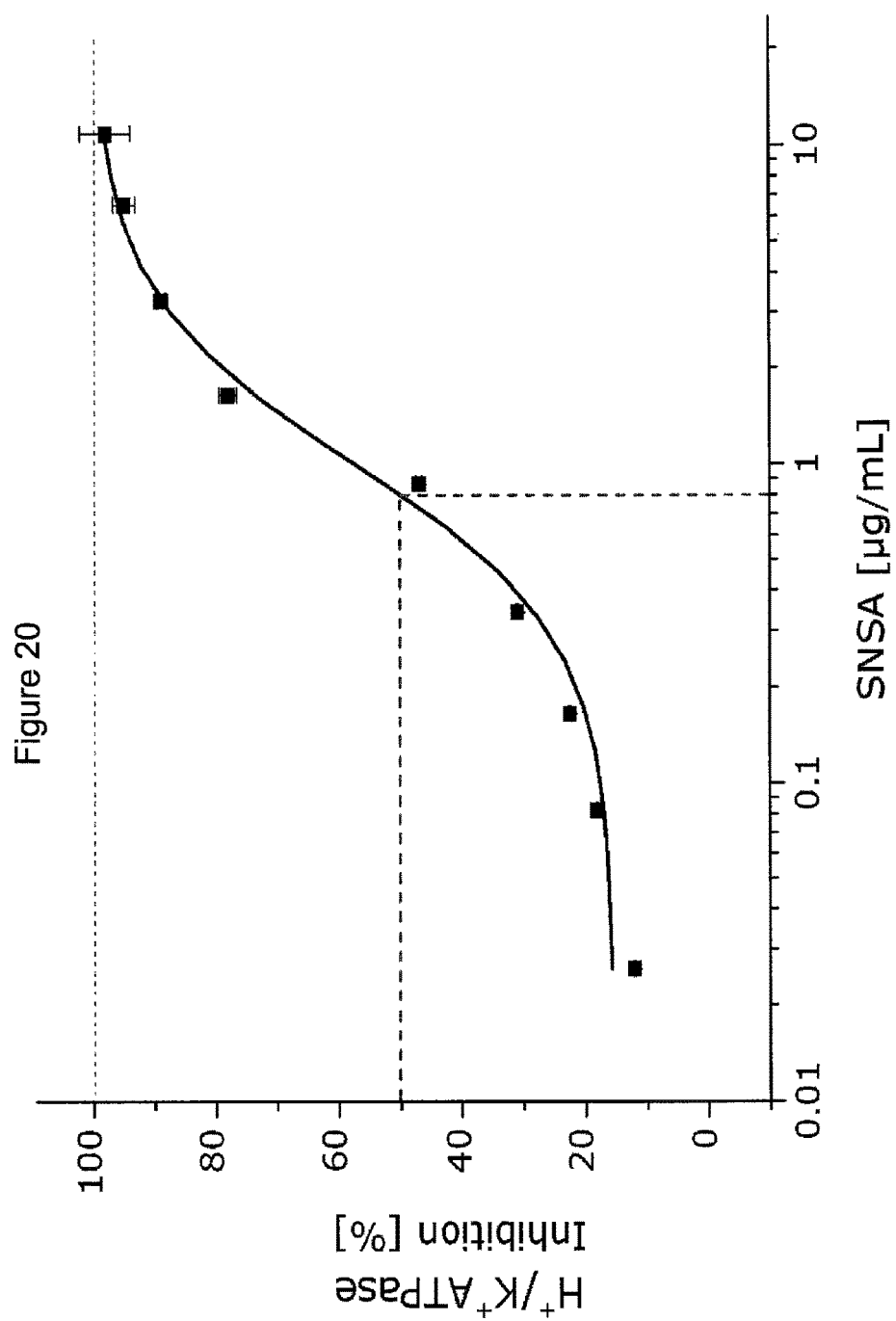
Figure 21:
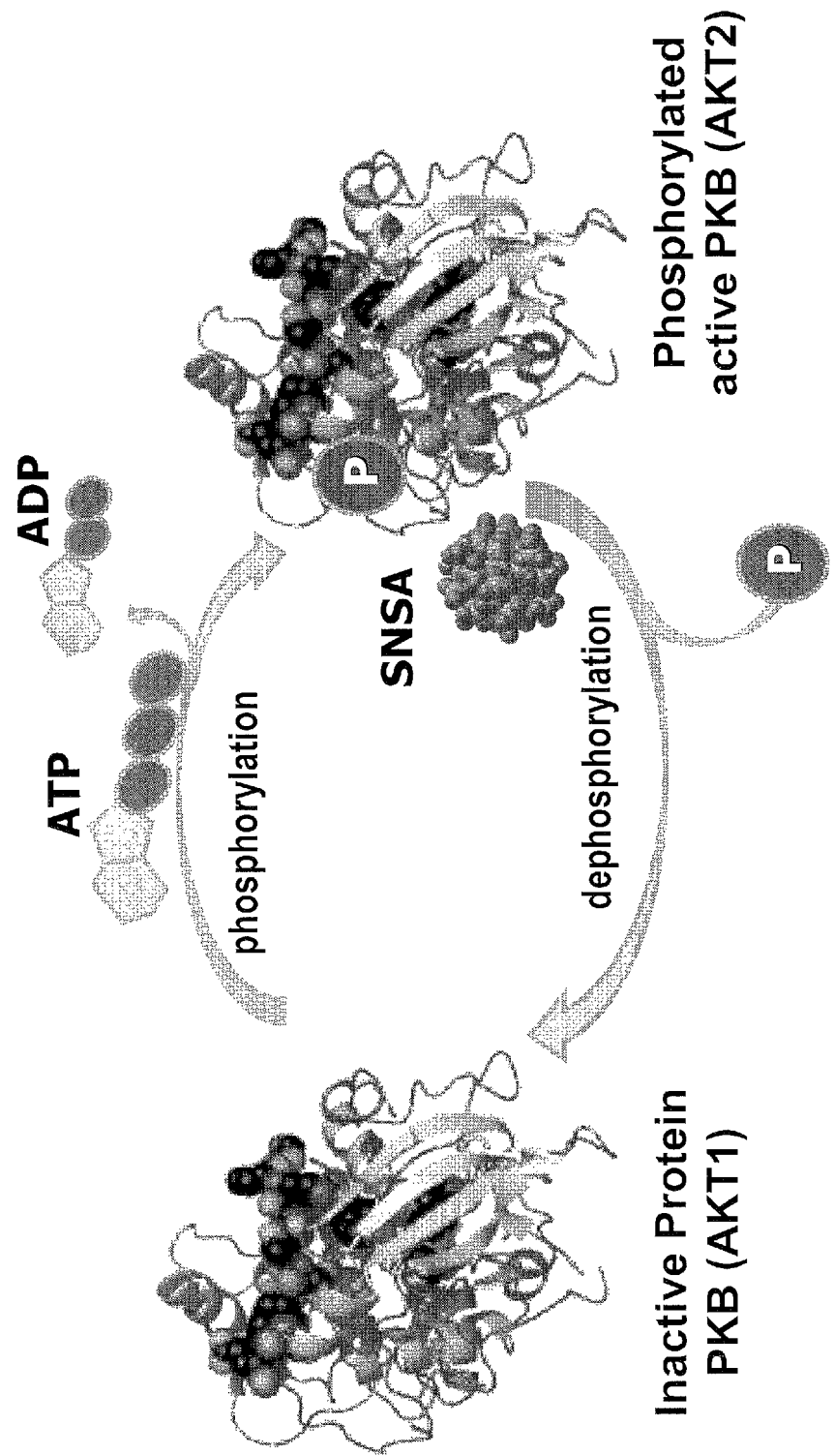

FIG. 20 The concentration dependent inhibition of $H^+/K^+$ ATPase by SNS b-101 with determination of the half-inhibition (IC50) value FIG. 21 Mechanism of the inventive interaction of SNSA with the phosphorylation-dephosphorylation process illustrated on the protein kinase PKB also known as AKT1 and AKT 2

Figure 22:
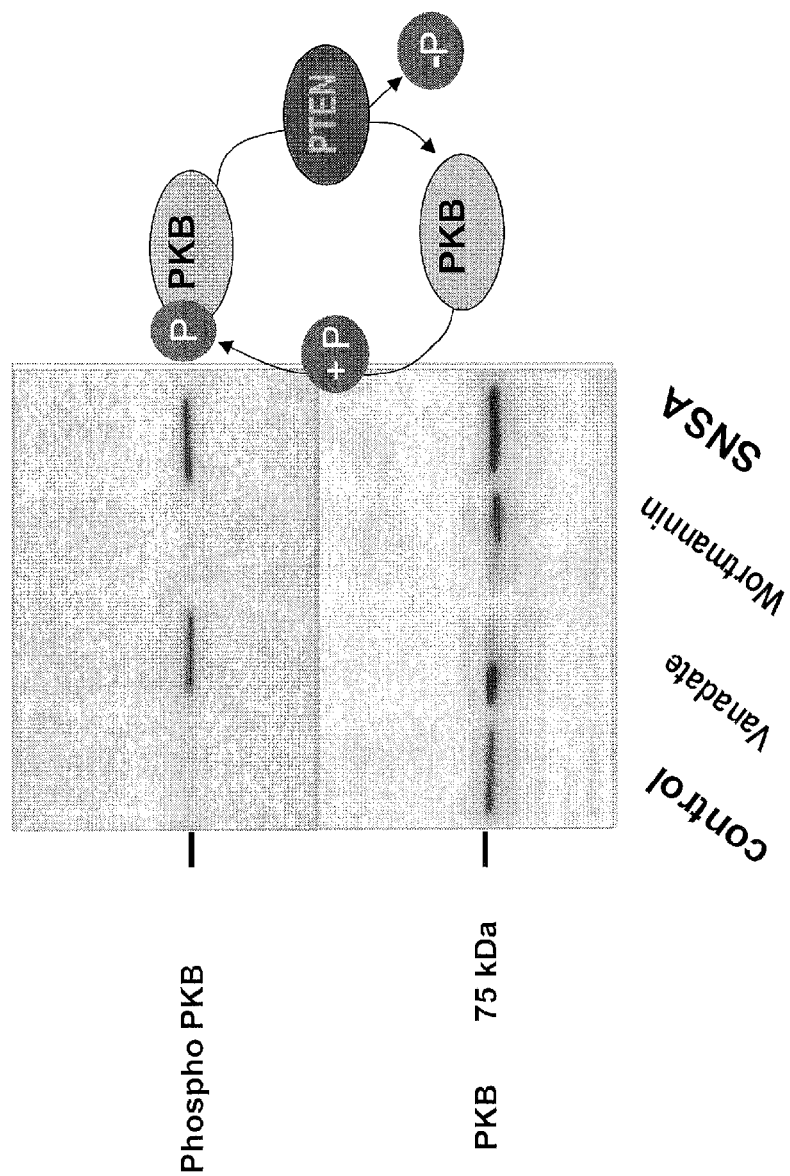

FIG. 22 Influence of SNSA on the PKB phosphorylation in THP1 cancer cells in comparison with sodium vanadate and pervanadates.

Figure 23:
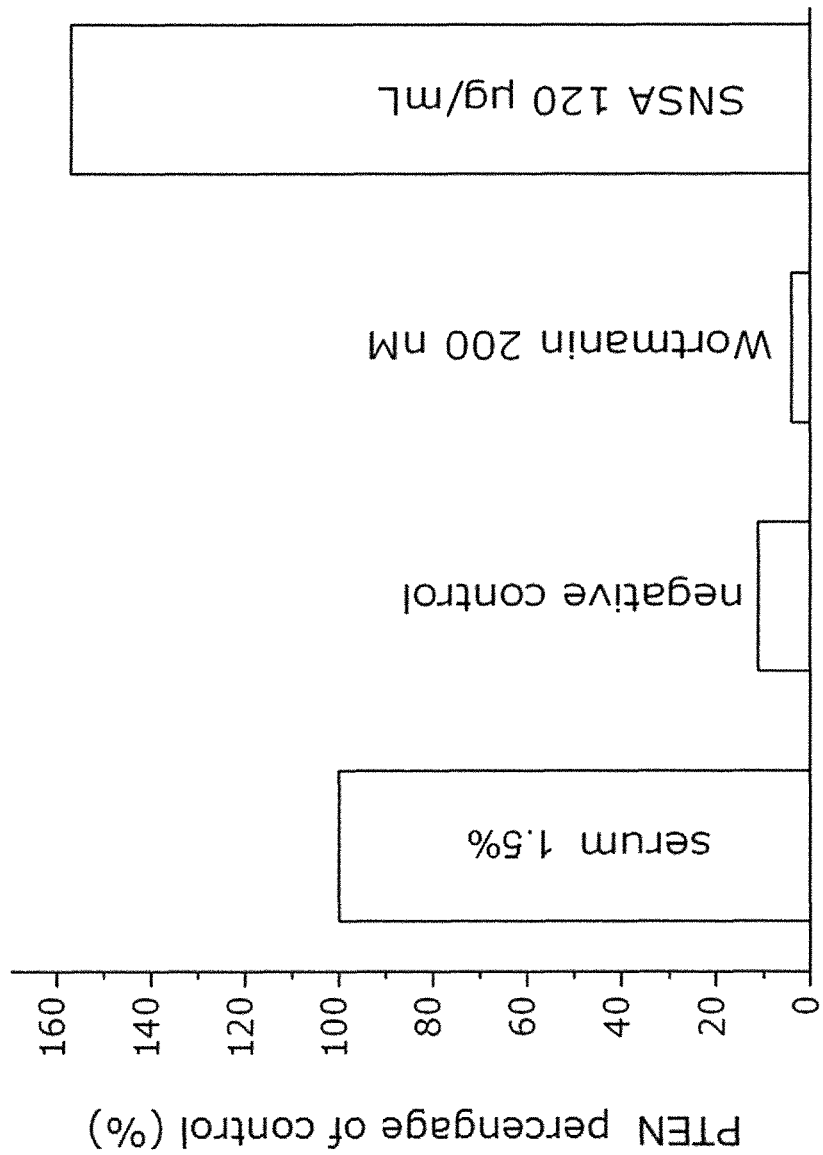
Figure 24:
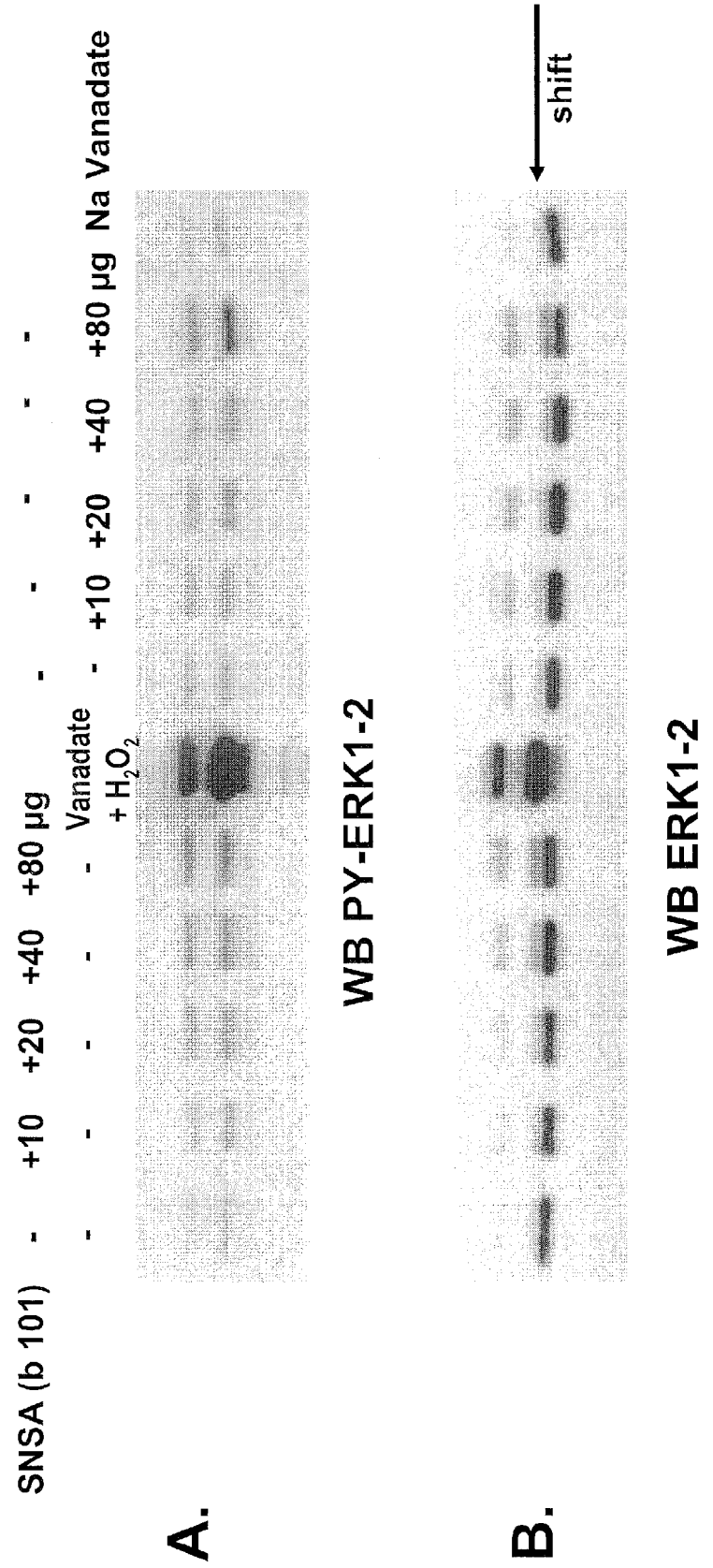

FIG. 23 Influence of SNSA on the protein phosphatases PTEN/AKT system as compared with Wortmanin a known AKT inhibitor Dose dependent enhancement of the Optical density by ELISA assessed influence of SNSA on the interaction between Fc and Protein A FIG. 24 Influence of SNSA on the ERK phosphorylation in THP1 cancer cells in comparison with sodium vanadate and its perhydrol complex.

Figure 25:
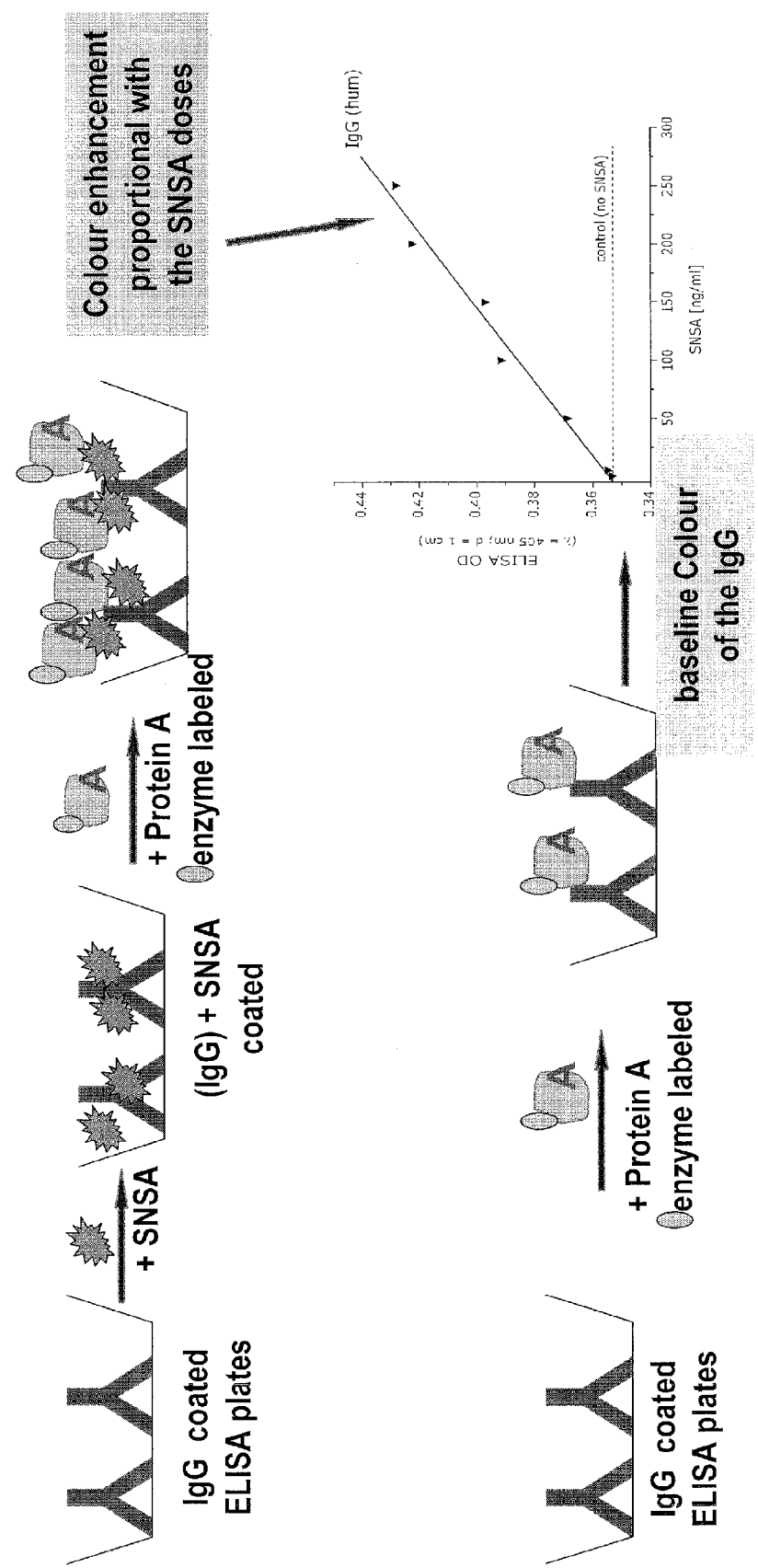
Figure 26:
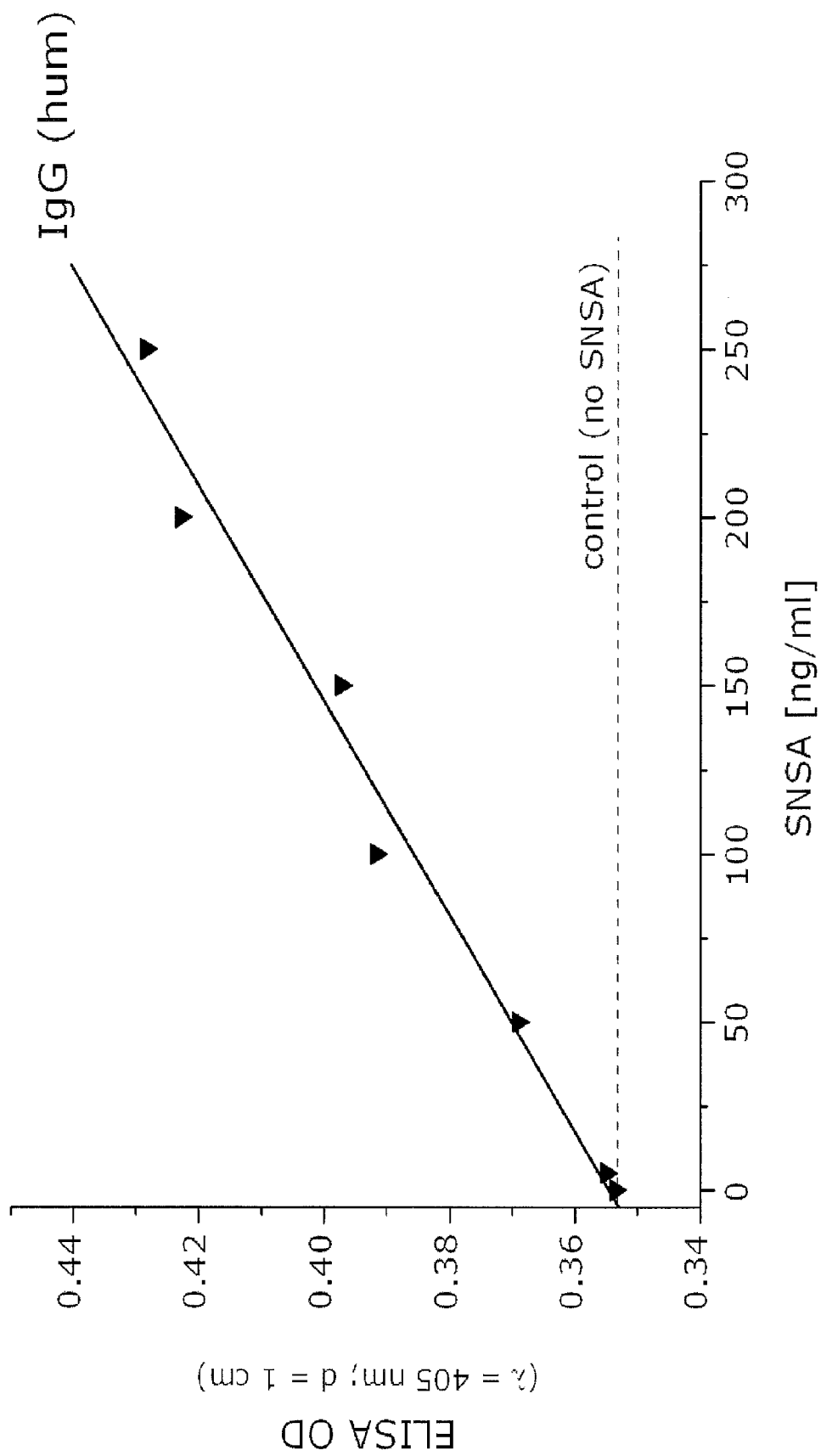

FIG. 25 Scheme of the ELISA assay of the inventive SNSA by its dose dependent influence of the interaction between IgG and enzyme labelled Protein A FIG. 26 Dose dependent increase of the optical density by the ELISA assessed influence of SNSA on the interaction between IgG and Protein A.

Figure 27:
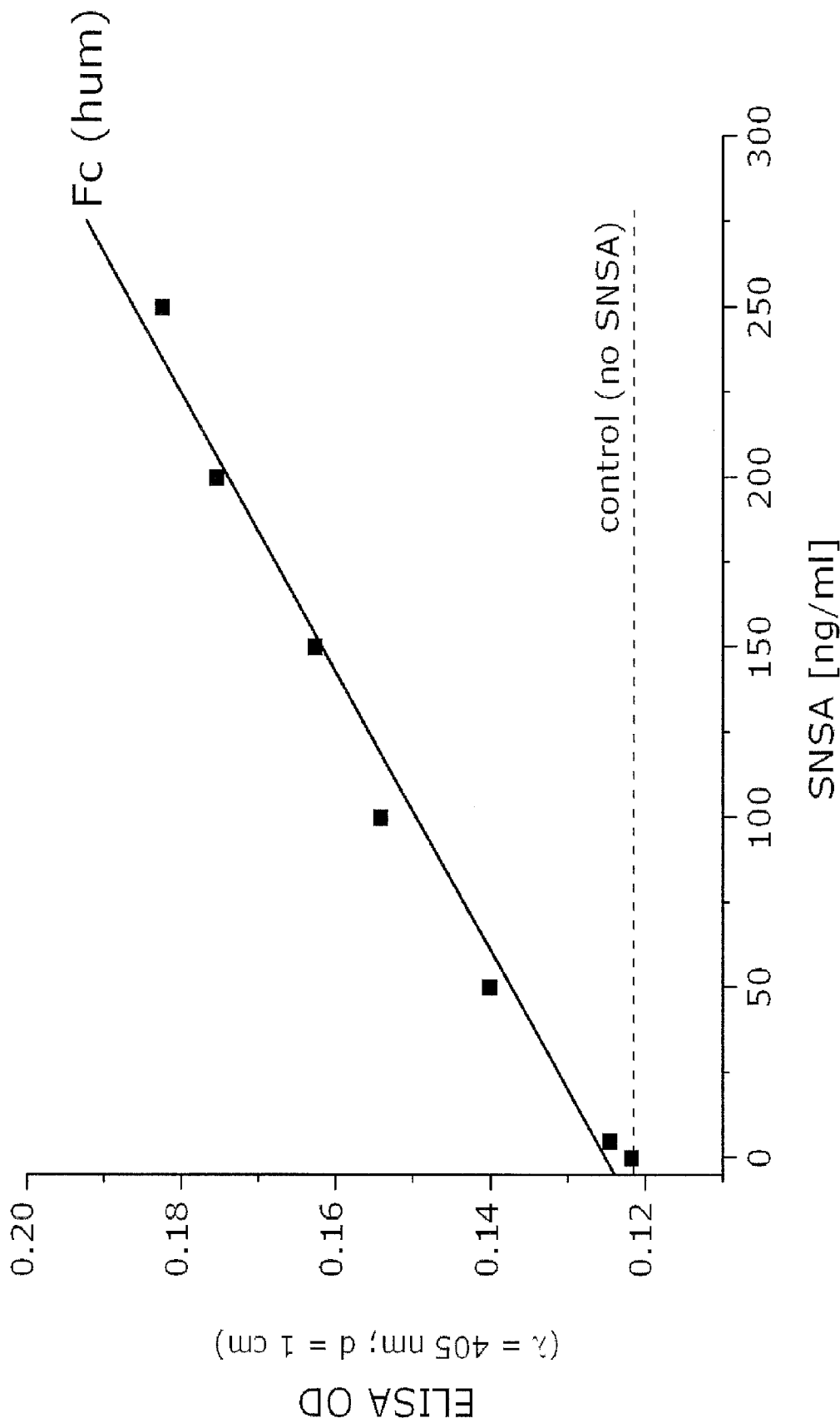

FIG. 27 Dose dependent increase of the optical density by the ELISA assessed influence of SNSA on the interaction between Fc and Protein A.

Figure 28:
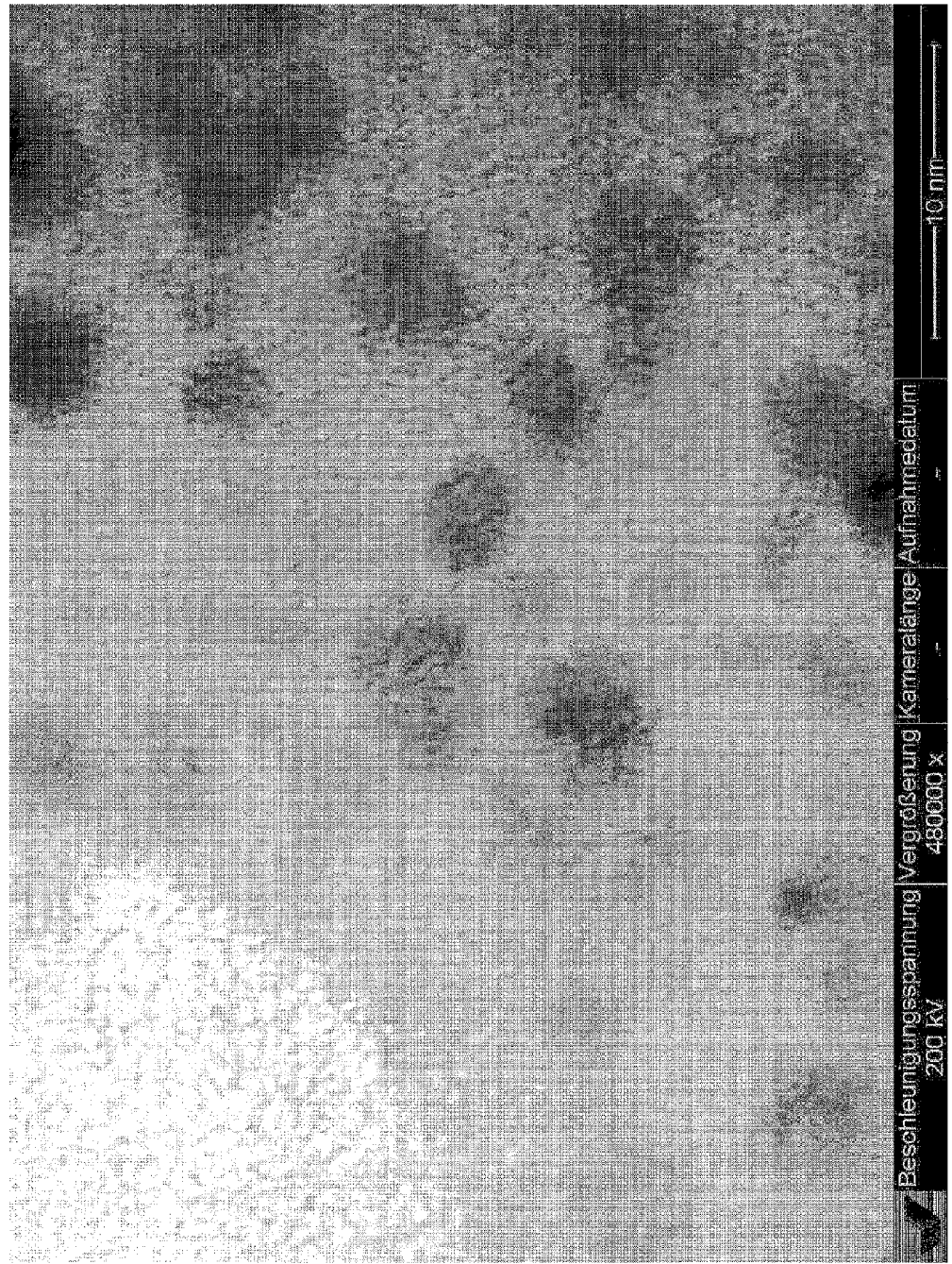

FIG. 28 Transmission electron microscopy image of SNSA (b-119) recorded with Philips CM 20 TEM, acceleration of 200 kV and 480,000× magnification.

Figure 29:
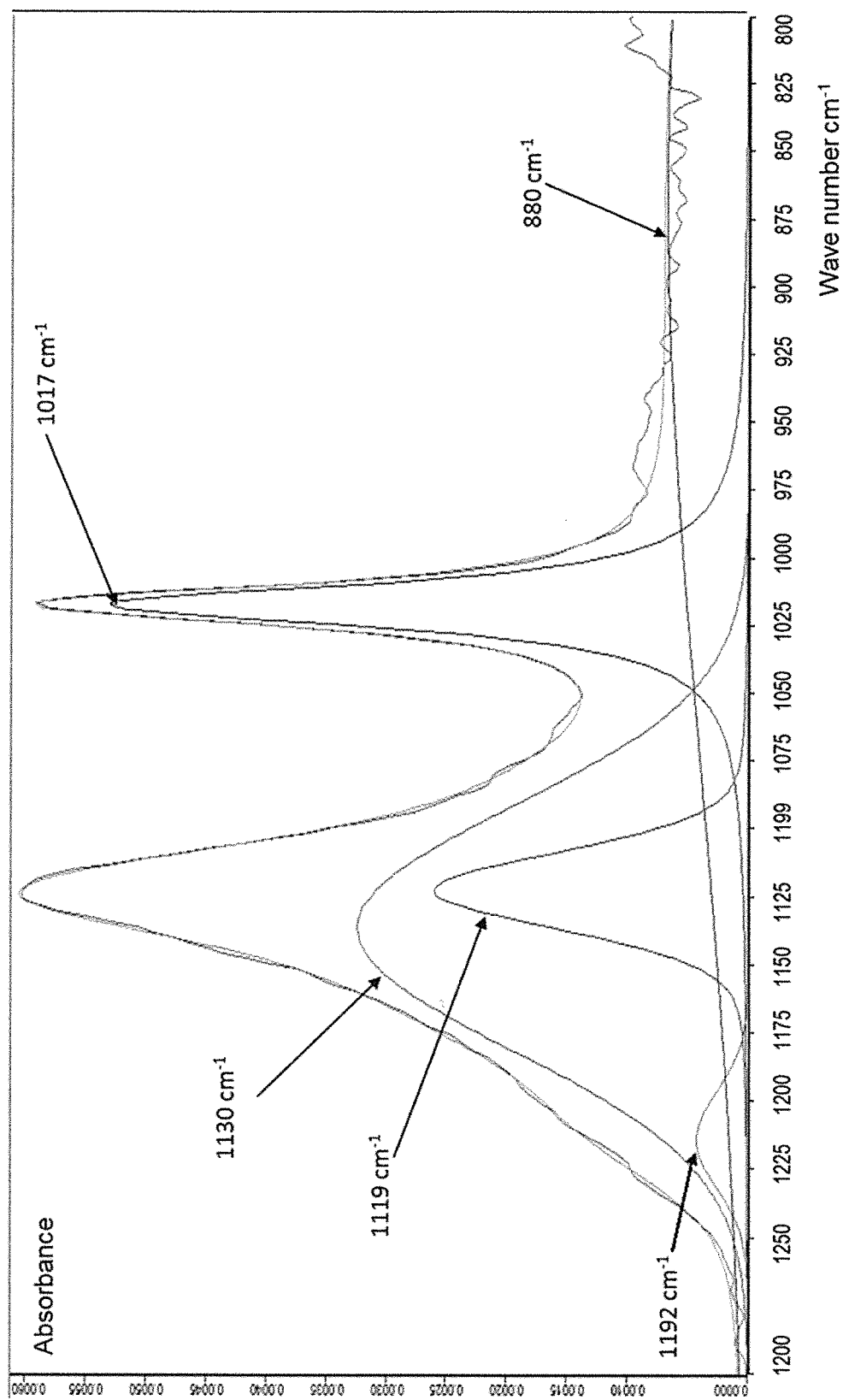

FIG. 29 Fourier Transform Infrared (FTIR) spectrum of the SNSA sample b-131 recorded by ATR technique with Tensor 37 spectrometer of BRUKER.

Figure 30:
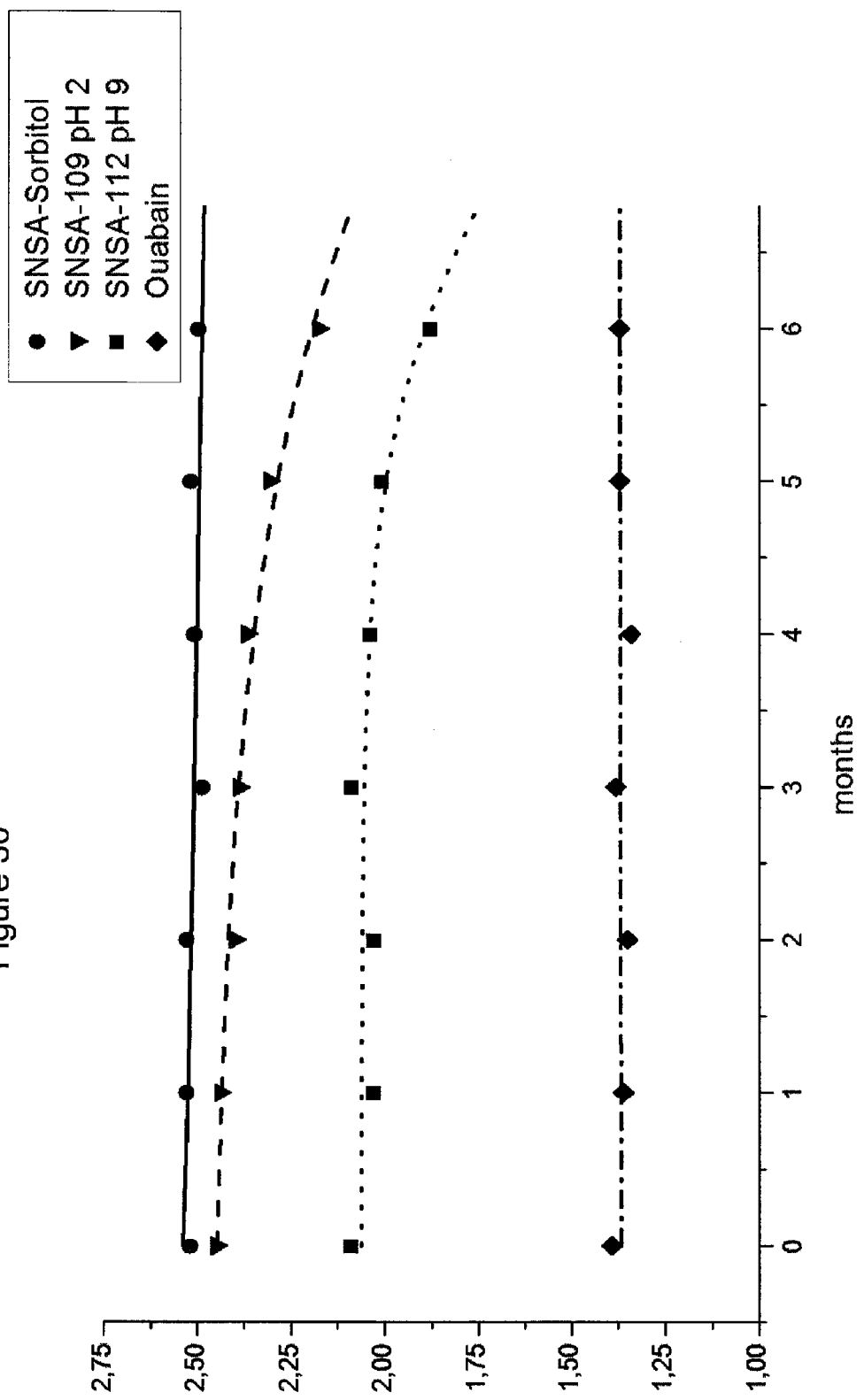

FIG. 30 Stability on long time storage of SNSA solutions at pH=2 and) and on solid support. Assessment by the Na,K-ATPase inhibition (Example 22)

Figure 31:
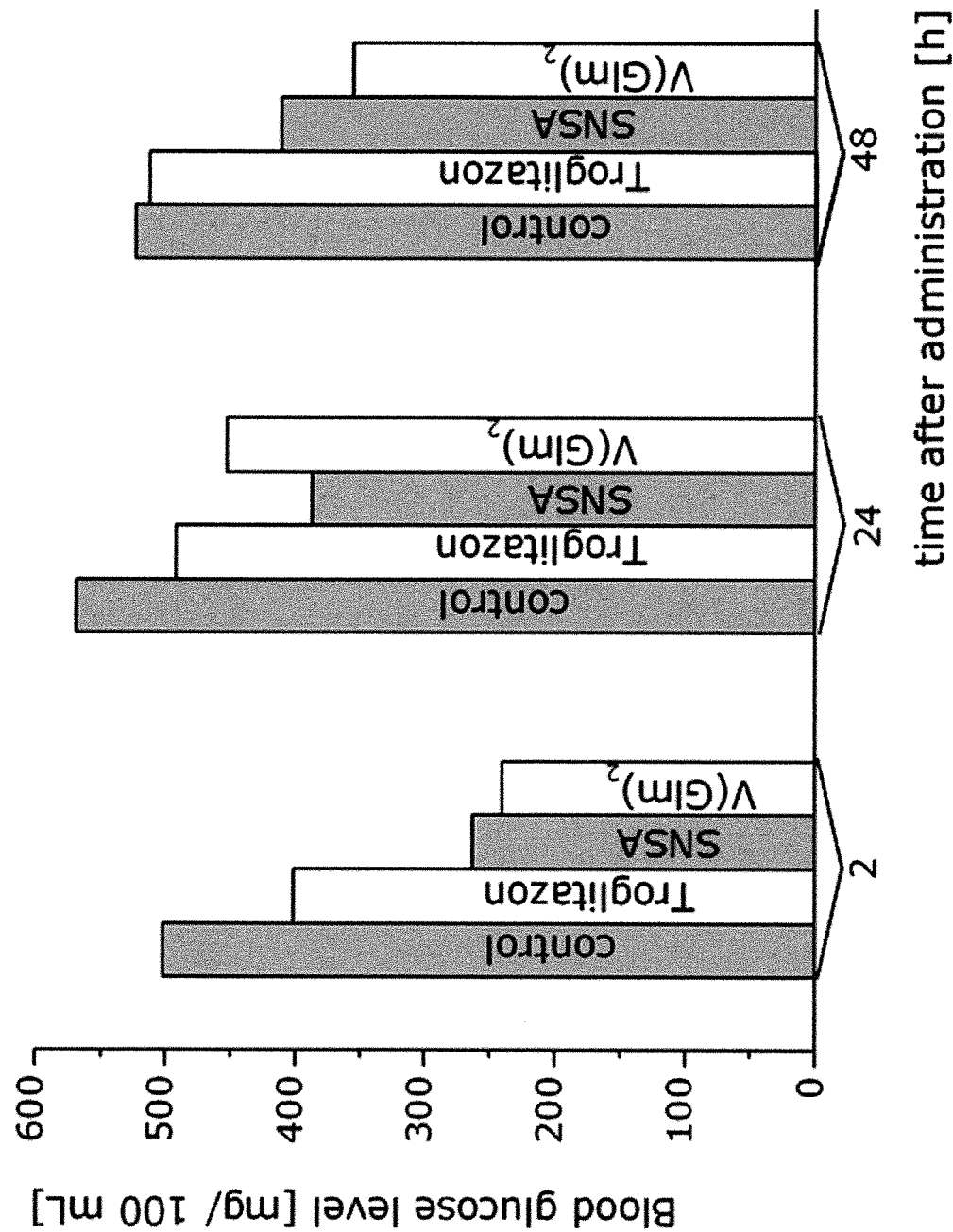

FIG. 31 Anti-diabetes efficacy of SNSA assessed on Streptozotocin induced diabetes model in rats as described by example 23.

Figure 32:
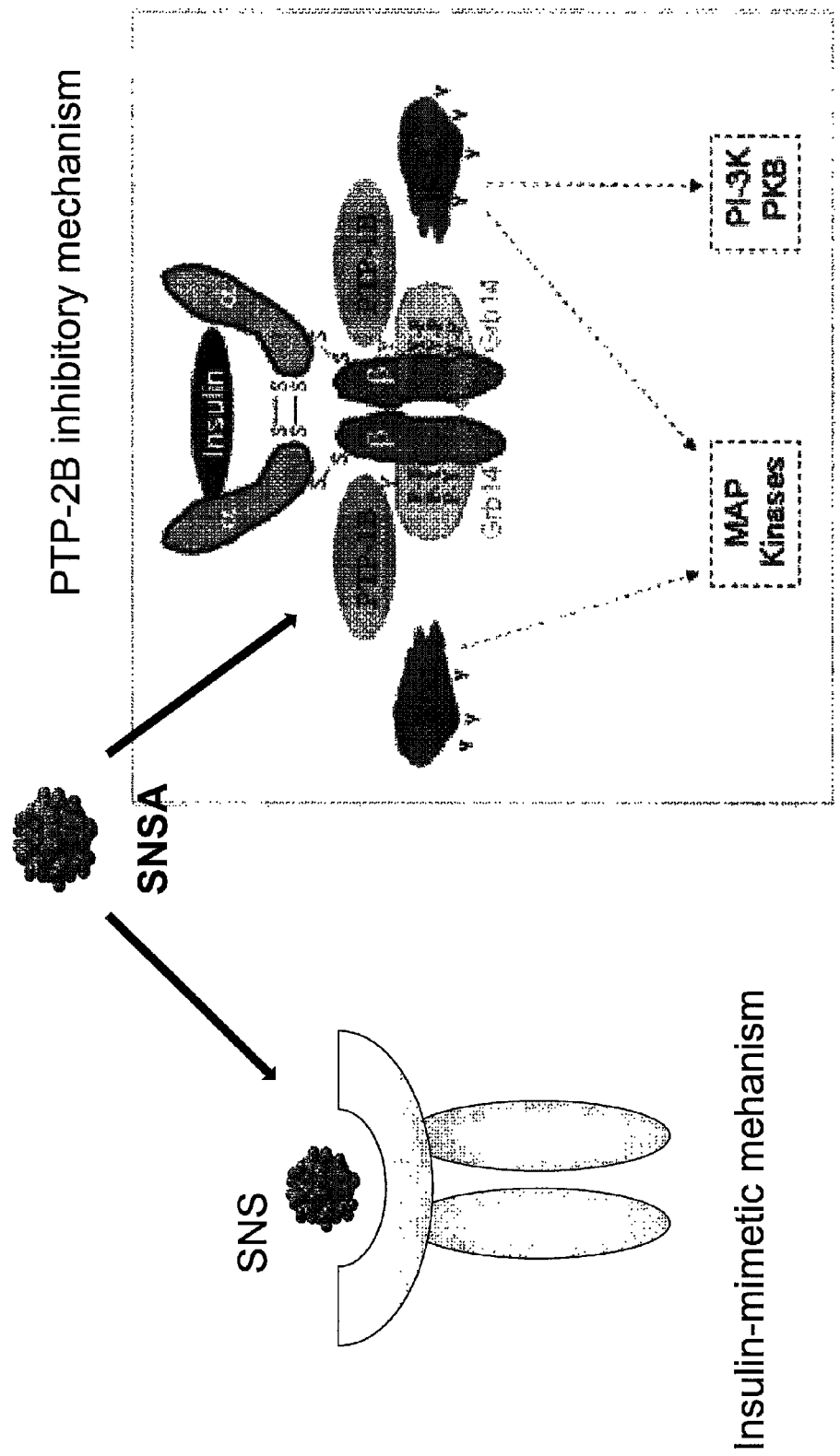

FIG. 32 Anti-diabetes mechanism of SNSA as insulin-mimetic or PTP1B inhibitor

FIG. 33 Effect of SNSA in two doses on branching of breast cancer cells MB-435

EXAMPLES

Example 1

Structure of the inventive sub-nano-silicic acid corresponding to the formula $Si_{36}O_{90}H_{36}$ is disclosed by the ball-stick model on the FIG. 11. Large balls correspond to Si atoms middle to O atoms ant the small white balls to the H atoms.

Example 2

Structure of the inventive sub-nano-silicic acid with the formula $Si_{46}O_{115}H_{46}$ shown by the space filling model (FIG. 12). Large spheres are Si atoms, middle O and the smalls of white colour are the hydrogens.

Example 3

Structure of an inventive sub-nano-silicic acid with the formula $Si_{42}O_{100}H_{32}$ is disclosed by the ball-stick model on the FIG. 13. Large balls correspond to Si atoms middle to O atoms ant the small white balls to the H atoms.

Example 4 A

Preparation of SNSA from tetra-alkyl-ortho-silicate

The amount of 29.5 ml (200 mMol) Tetramethoxysilane, $Si(OMe)_4$ purchased from ABCR was mixed with 100 ml distilled water in 500 ml round bottle PTE vessel. In the induction phase the pH of the solution was tuned from the 6.2 to 4.1 by adding gradually small volumes of diluted acetic acid. The temperature in the induction phase was increased in less than 5 minutes to 42° C. During the condensation phase the pH of the solution was tuned from 4.1 to 3.9 and the temperature decreased from 42° C. to 25° C. Duration of the condensation phase is between 40-50 min according to the data of in-process control by Size-exclusion chromatography SEC. At the beginning of the stabilization phase the pH of the solution is raised with 1N NaOH rapidly to 9.0. The methanol resulted by the hydrolysis of TMOS was removed by a vacuum rotatory evaporator (Büchi Rotavap) with gently heated water bath (40-45° C.). The pH of the final solution is controlled and adjusted to 8.9-9.1 using a 0.1N NaOH solution.

Content in sub-nano-silicic acid SNSA of the final product is assayed by Size-exclusion chromatography which confirms the higher polymeric side products. Quality assessment of SNS performed by Dynamic Light Scattering (DLS) shows the existence of a sharp peak at 1.6 nm and the absence of higher molar mass associates.

Example 4 B

Preparation of SNSA from Water Soluble Alkaline Silicate 10 ml of commercially available solution of sodium silicate (reagent grade, Sigma-Aldrich) is diluted 1:10 with water resulting in a solution with 2.7% $SiO_2$. The 100 ml of diluted solution in a polypropylene flask is cooled with external bath and is treated with similarly cooled solution of 1N HCl to reach rapidly the pH=2 with a temperature gradient started by 8-10° C. to 20° C. at the end of the induction phase in less than 10 min. The condensation phase was conducted 30 min at pH=4.0 and temperature of 38±2° C. Stabilization was accomplished by rapid rising of the pH to >9.2 with NaOH 1N.

Example 5

Preparation of SNSA from Soluble Alkaline Silicate 6 g powdered Silica gel 60 Sigma Aldrich is suspended in 50 ml 1N NaOH and solved at 100° C. The filtered and cooled (8-10° C.) final solution is acidified by adding gradually and with slow stirring the amount of previously neutral-washed cationic resin of the type Amberlite 120A which raises the pH of the solution to =4.1±0.2. The supernatant is rapidly separated by vacuum filtration. After this induction phase the temperature of the solution is heated from 8-10° C. to 40±2° C. with a non-linear gradient. Condensation phase was conducted for 60 minutes at temperature between 32 and 35° C. Stabilization of the final solution by admixture of hydrochloric acid 1N to reach pH 2.1.

Example 6

Dynamic Light Scattering and Zeta Potential of the SNSA

The Dynamic Light Scattering and Zeta Potential of the SNSA (batch-116) was assessed by the Zetasizer device of Malvern Instruments. The measurement samples were diluted from the SNSA stock solution of 24.0 mg/ml concentration as provided by the synthesis batch 116. It resulted a molecular diameter of 1.6 nm corresponding to a molar mass of 4.1 kDa.

Example 7

Dynamic Light Scattering and Zeta Potential of the SNSA

The Dynamic Light Scattering and Zeta Potential of the SNSA (batch-118) was assessed by the Zetasizer device of Malvern Instruments Measurement samples were diluted from the SNSA stock solution of 24.0 mg/ml concentration as provided by the synthesis batch 118. The data showed a molecular diameter of 2.2 nm for the SNSA sample corresponding to a molar mass of 6.2 kg/mol (kDa) (FIG. 14).

Example 8

Size Exclusion Chromatography Analysis of SNSA

The Size exclusion chromatogram of FIG. 15 was obtained for the SNSA sample batch 118, working with Kontron Instruments Pump System 525, TSK Gel G2500 PWXL column of dimensions: 300×7.8 mm, solvent=water, flow rate=0.5 ml/min Detection by Jasco refractive index detector: RI-2031 Plus. Correlation of the measured retention time 11.2 min values in the SEC with the polyethylene glycol standard curve FIG. 16 provided molar mass values of the inventive substance sample SNSA-118 corresponding to 6.2 kDa. The SEC method allows the rigorous control of the manufacture process and of the stability f the product by long time storage.

These data correlates with DLS diagram of the sample SNSA b 118 shown in FIG. 14 which shows a molecular diameter value at the narrow range of 2.2 nm which corresponds approximately to a molar mass of 6.2 kDa and n value of n=92-96.

Example 9

Size Exclusion Chromatography Standard Curve

The Size exclusion standard curve representing the retention time molar mass function on FIG. 16 was obtained working with Kontron Instruments Pump System 525, TSK Gel G2500 PWXL column of dimensions: 300×7.8 mm, solvent=water, flow rate=0.5 ml/min Detection by Jasco refractive index detector: RI-2031 Plus.

Samples of 20-80 µl of commercially purchased polyethylene-glycol (PEG) poly-styrol-sulphonate, or polyacrylic acid standards were used comparatively to establish the standard curve. FIG. 16 gives the data with PEG standards.

Example 10

29Si NMR Spectral Investigation of SNSA

The NMR spectra of the liquid samples were collected with a JEOL Eclipse 400 NMR spectrometer operating at 100.6 MHz. For comparison, solid state $^{29}$Si CP-MAS NMR spectra of the samples were recorded on a Bruker MSL 300 spectrometer operating at 59.6 MHz, using a 4 mm probe. A n/2 pulse delay of 5.1 µs, contact time of 10 ms, and recycle delay of 12 s were used for the cross-polarizing measurement. The solution of active silica is measured in a PTFE (=teflon) tube to avoid the common "glass hill" of the usual NMR tubes.

FIG. 17 shows the $^{29}$Si NMR spectrum of the SNSA sample b-109 at concentration of 24 mg/ml in water.

Example 11

SNSA Inhibits the Rabbit Medulla Na,K-ATPase

Membrane preparation with a high concentration of Na,K-ATPase was prepared from the outer medulla providing specific ATPase activity values in the range of 2.000 to 2.400 µmol $P_i$/h/mg protein at 37° C. for the rabbit enzyme. The enzyme activity of the Na,K-ATPase was determined in a buffer containing 25 mM imidazole (pH 7.2), 100 mM NaCl, 10 mM KCl, 5 mM $MgCl_2$, 1.5 mM $Na_2$ATP 5 nM Na,K-ATPase, 2 mM PEP, 450 units/ml of pyruvate IC50nase and lactate dehydrogenase, and initially 80 µM NADH. All experiments performed at 37° C.

The enzyme activity in absence of inhibitor was used as reference. Inhibition of rabbit Na,K-ATPase by the SNS probe is shown in (FIG. 18). The concentration-dependent inhibition of the enzyme activity, was used to calculate the half-inhibitory concentration $IC_{50}$ of SNS resulting values in the range of ($IC_{50}$=0.32-0.5 µg mL$^-$ Calculated with the molar mass value of $M_r$=6.2 kDa established by Size Exclusion chromatography (SEC) for the SNSA sample (b-118) and the $IC_{50}$=0.45 µg mL$^{-1}$ it results an $IC_{50}$=72 nanoMol L$^{-1}$ for this sample. This inhibitory potential of SNS is comparable with that of vanadates and is of >10 fold higher as that of ouabain and hellebrin, two water soluble cardiac glycosides which inhibits the same enzyme with $IC_{50}$=1.0 µMol L$^{-1}$.

Phosphoenolpyruvate (PEP), pyruvate kinase, lactate dehydrogenase, NADH and ATP (disodium salt) were from Roche (Mannheim). All other reagents were purchased from Merck (Darmstadt) or Sigma-Aldrich (Deisenhofen) at the highest quality available. The pyruvate kinase/lactate dehydrogenase assay was not affected by SNSA. The inhibitory action of the SNS compounds was fully developed within the time of mixing the buffer in the cuvette with the inhibitor solution added (1-10 µl). In the presence of excess ouabain the Na,K-ATPase preparation was fully inhibited, a fact which confirmed the high degree of purity of the enzyme preparation as additionally controlled by SDS electrophoresis (data not shown). The normalized specific activity was calculated as the ratio of the residual activity upon addition of increasing amounts of SNSA, and the reference activity.

Example 12

Inhibition of the Rabbit Muscle Ca-ATPase by SNSA

Ca-ATPase was prepared from rabbit psoas muscle with the whole procedure was performed at temperatures below 4° C. The protein content of the membrane preparation was determined as described previously and was found to be 2-3 mg/ml for the most active fractions after the final density gradient separation. The specific enzymatic activity was about 2 μmol $P_i$/h/mg protein at 20° C.

The enzyme activity was determined (FIG. 19) by the same coupled pyruvate kinase/lactate dehydrogenase assay as in the case of the Na,K-ATPase using buffer (pH 7.5) containing 25 mM HEPES, 1 mM $MgCl_2$, 50 mM KCl, and 0.2 mM $Ca^{2+}$. Phosphoenolpyruvate (PEP), pyruvate kinase, lactate dehydrogenase, NADH and ATP (disodium salt) were from Roche (Mannheim). All other reagents were purchased from Merck (Darmstadt) or Sigma-Aldrich (Deisenhofen) at the highest quality available.

Background enzyme activity of the isolated preparation was obtained by addition of 1 μM tharpsigargin. The specific activity of the Ca-ATPase preparation was at ~1.8 units/mg at 20° C. and pH 7.5 (corresponding to 1.8 μmol ATP hydrolyzed per mg protein/min).

Example 13

Inhibition of the Hog Gastric H/K-ATPase by SNSA

The gastric H,K-ATPase was derived from hog gastric mucosa by previously published methods, which involve differential and density gradient centrifugation. The crude gastric mucosa membranes were collected from the stomach and homogenized in a solution of 0.25 M sucrose, 5 mM PIPES/Tris, pH 6.8, and 1 mM EGTA. The homogenate was centrifuged at 11,000 rpm in a Sorvall GSA rotor for 45 min. The supernatant was centrifuged at 30,000 rpm in a Beckman (Fullerton, Calif.) type-30 rotor for 1 h. The microsomal pellet was re-suspended in a solution of 0.25 M sucrose, 5 mM PIPES/Tris, pH 6.8, and 1 mM EGTA.

The microsomal suspension was purified using Z-60 zonal rotor. In the isolated vesicles; 90% of the H,K-ATPase is oriented as in the parietal cell with the cytoplasmic side outward. Specific ATPase activity of the H,K-ATPase was determined by the pyruvate-kinase/lactate dehydrogenase assay; Phosphoenolpyruvate (PEP), pyruvate kinase, lactate dehydrogenase, NADH and ATP (disodium salt) were from Roche (Mannheim). All other reagents were purchased from Merck (Darmstadt) or Sigma-Aldrich (Deisenhofen) at the highest quality available. The specific activity of the H,K-ATPase-containing vesicles preparations was in the range of 80-120 mmol Pi per milligram total protein one hour at 37° C. The $IC_{50}$ values were defined as the inhibitor concentration that produced 50% inhibition of K-stimulated ATPase activity. The $IC_{50}$=0.78 μg/ml value was calculated by non-linear least-squares fitting of a sigmoidal function to the experimental data using Origin™ 5.0. The sample size was based on three assays each measured in triplicate for each compound.

The graphical determination of the half-inhibitory concentration $IC_{50}$=0.78 μg/ml is given in (FIG. 20)

Example 14

Activity of SNSA on PTEN (Phosphatase and Tensin Homolog on Chromosome 10)

Materials

NIH3T3 fibroblast cells (LGC Promochem, ATCC) Dulbecco's Modified Eagle's Media (DMEM from Sigma) Newborn Calf Serum (NCS from GIBCO Invitrogen) Wortmannin (Calbiochem) Anti-P-PKB(S473) antibody (Cell Signalling) Anti-Mass-PKB antibody (Upstate) ECL Western Blotting Analysis System (Amersham Biosciences).

Method:

Fibroblast cells NIH3T3 were grown in 6-well-plates until they were dense enough. Cells were then starved in 0% DMEM overnight in order to reduce their metabolism and of the Protein-Kinas B (PKB). Prior the test the media was removed and newborn calf serum, (NCS) added to stimulate PKB phosphorylation. After adding 1.5% serum cells were incubated for 5 min followed by adding of either 200 nM Wortmannin a PI3K-inhibitor, or SNSA b-101 (120 μg/ml) to the fibroblasts and incubated for 25 min, removed washed with PBS. Finally, cells were lysed with 4×SDS gel-loading buffer and boiled for 10 min.

All cell lysate samples were ran on 9% SDS-PAGE (Laemmli et al.), transferred to nitrocellulose membranes, blocked with 5% milk powder in TBST buffer for 30-60 min. Western Blot analysis carried out by incubating the membranes with anti PKB antibody (1:1000) or anti phospho-PKB (S473) antibody (1:2000) in 3% milk powder in TBST overnight at 4° C. Membranes were then washed with TBST buffer for at least three times 10 min. Finally, membranes were incubated for 1 h at room temperature with a secondary anti-mouse serum coupled with horseradish peroxidase (BIORAD) (1:1000) in 3% milk powder in TBST. Membranes were washed with TBST buffer for three times 10 min. Finally, the Western Blots were developed with ECL solution (Amersham Biosciences) and signals detected in a Digital Black Box from Fuji-Film.

Results

120 μg/ml of the inventive silicic acid SNSA leads to a visible and potent up-regulation of PKB dephosphorylation (FIG. 21) which may be explained as an inhibitory effect on PTEN (FIG. 22) which was proved in a similar experiment in comparison with the PI3K inhibitory standard Wortmanin (FIG. 23).

Example 15

Activity of SNSA on ERK-Phosphatase in TPH1

Upon treatment of leukaemia cell line THP1 SNSA induces stimulation of signalling, leads to ERK1 and ERK2 activation (phosphorylation). The effect of SNSA (b-101) is very similar to vanadates by the activation of ERK1 and ERK2. The peroxydation of sodium vanadate with $H_2O_2$ increases strongly the activation of ERK1 and ERK2 (FIG. 24). Conversely the treatment of SNSA with $H_2O_2$ has a less significant effect on ERKs, which reveals that SNSA is not sensible to peroxydation than vanadates.

Proliferation of THP1 cells upon treatment with SNSA is not significantly changed after 24 and 48 hrs. A weak inhibition of proliferation was observed after 96 hrs of observation. SNSA doesn't inhibit the viability of cancer THP1 cells (c=160 μl/ml of growth media). In comparison with Vanadate SNSA is definitely not toxic for cells.

Cancer cell BC cell line BT20 treated with SNSA shows weak increasing of EGFR phosphorylation as well.

Example 16

Interaction of SNSA with Proteins

Interaction of the biologically active silicic acid SNSA with human IgG protein was quantitatively assessed by the ELISA technique as follows:

The 96 well ELISA plate was coated with 200 μl of a 100 μg/ml solution of human IgG (Sigma 14506) in sodium carbonate buffer pH 9.5 (40 mM $NaCO_3$ and 60 mM $NaHCO_3$) and incubated overnight at 4° C. Solution removed on next day, plate washed 3× with PBS & 0.05% Tween20. It followed incubation with 200 μl 2% BSA in PBS at room temperature for the saturation of the free binding sites. BSA solution removed after 1 h, the plate washed 3× with PBS & 0.05% Tween20 and 3× with PBS. The wells were treated with 100 μl of previously diluted stock solutions of SNSA (b-118) in the range of: 1000-10 ng/ml. Incubation with SNSA for 2 h at room temperature, remove and wash 3× with PBS & 0.05% Tween20 and 3× with PBS.

Incubation for 2 h at room temperature with 100 μl per well ProteinA-alkaline phosphatase conjugate (Sigma P-7488) 1:2000 diluted in PBS. Solution removed and the plate washed 3× with PBS & 0.05% Tween20 and 3× with $H_2O$. Each well incubated with 100 μl of the substrate solution pNPP (Sigma N1891) at room temperature for 120 min and Optical density (OD) at 405 nm measured with MRX Microplate Reader (Dynatech Laboratories).

The methodology for the sensitive assay of SNSA is illustrated on diagram in FIG. 25 with the results obtained by the ELISA method. Since the wells were incubated with the same amount of IgG (20 μg/well) which reacts selectively with Protein A, it was expected to result a colour reaction of the same intensity in all wells. Surprisingly it resulted in a linear enhancement of the colour reaction proportional to the amounts of the inventive silicic acid in solution Remarkably the OD curve increases linearly in the concentration range from 10 ng to 300 ng/ml of SNSA (FIG. 26) and becomes flattened only by higher concentrations of SNSA. The observation of this SNSA-dose dependent enhancement of the interaction of the IgG molecule with protein A is of high applicative potential since it allows the very sensitive assay of the inventive substance SNSA in the nanogram range in various samples including of biological origin.

Example 17

Assay of SNSA

The 96 well ELISA plate was coated with 200 μl of a 100 μg/ml solution of ChromPure human IgG Fc Fragment (Dianova) in sodium carbonate buffer pH 9.5 (40 mM $Na2CO_3$ and 60 mM $NaHCO_3$) and incubated overnight at 4° C. Solution removed on next day, plate washed 3× with PBS & 0.05% Tween20, followed by incubation with 200 μl 2% BSA in PBS at room temperature for saturation of the free binding sites. BSA solution was removed after 1 h, the plate washed 3× with PBS & 0.05% Tween20 and 3× with PBS. The wells were treated with 100 μl of previously diluted stock solutions SNSA (b-118) in the range of: 1000-10 ng/ml. Incubation with SNSA for 2 h at room temperature, remove and wash 3× with PBS & 0.05% Tween20 and 3× with PBS. Incubation for 2 h at room temperature with 100 μl per well ProteinA-alkaline phosphatase conjugate (Sigma P-7488) 1:2000 diluted in PBS. Solution removed and the plate washed 3× with PBS & 0.05% Tween20 and 3× with $H_2O$. Each well incubated with 100 μl of the substrate solution pNPP (Sigma N1891) at room temperature for 120 min and Optical density (OD) at 405 nm measured with MRX Microplate Reader (Dynatech Laboratories).

The diagram in FIG. 27 illustrates the results obtained by the ELISA method with human Fc fragment. Since the wells were incubated with the same amount of Fc (20 μg) which reacts selectively with Protein A, it was expected to result a colour reaction of the same intensity in all wells. Surprisingly it resulted in a linear enhancement of the colour reaction parallel with the increased amounts of the silicic acid doses! Remarkably the OD increases linearly in the concentration range from 10 to 300 ng/ml of SNSA. The standard curve established with known concentrations of SNSA allows the quantitative assay of SNSA in samples with unknown concentrations in the 1-1000 ng/ml range.

Example 18

Application of SNS in Diabetes Model

Administration of SNSA (b-118) in a dose of 24 mg/kg body weight in diabetes mice db/db lowered blood glucose level within 2 h of administration by 48% compared with the higher reduction of the vanadate (52.5%) and the 22% of the diabetes drug. The long term reduction of the blood glucose level by SNSA was modest at only 19% at 24 and 48 h after administration in comparison to the control animals treated with vehicle. The long time efficacy of SNSA by this test was weaker than of the bis-L-Glutamyl Vanadate with 32% reduction of BGL even after 48 hours.

Example 20

Characterization of SNSA by Transmission-Electron Microscopy (TEM)

Specimens of the sub-nano-silicic-acid solutions were drop-coated deposited on carbon-coated parlodion films supported on 400 mesh copper grids (Ted Pella) and allowed to dry under controlled conditions. The TEM measurements were recorded by the Philips CM 20 transmission electron microscope with the applied magnetic field parallel to the nano-silicic acid film surface plane.

The characteristic TEM image (FIG. 28) of the investigated SNSA specimen (b-119) was obtained with acceleration voltage of 200 kV and with a magnifications of 480,000. The diagram shows the existence of spheroidal silica species with molecular diameter in the range of 2.5-4.0 nm which are definitely lower than typical silica nano-particles with molecular diameters >5.0 nm.

It should be noted that the applied Transmission Electron Microscopy technique shows actually the image of the "solid" particles resulted after the rapid evaporation of the solvent water. Actually the rapid "dehydration" of the SNSA solution removes not only the solvent water molecules will cause inherently elimination of water within and between the condensed silicic acid molecules. The results of these intra- or intermolecular water condensations are the structurally modified or aggregated SNSA derivatives of higher molar mass in comparison with the genuine species.

Example 21

Characterization of SNSA by Fourier-Transform IR Spectroscopy

Fourier-Transform Infra Red (FTIR) spectroscopy was applied to characterize the inventive sub-nano-silicic acid. The spectra were recorded with the Tensor 37 FTIR spectrometer of BRUKER-Optics (Rosenheim Germany) applying the ATR Miracle Pike method in the range of 4000-400 cm-1 with 64 scans with a resolution of 4 $cm^{-1}$.

The samples were prepared from the SNSA (b130 and b131) stock solution with concentration of 24 mg/ml water, pH 8.9, as thin liquid film between two polyethylene foils. The spectra of the PE-foils and of the solvent were separately measured and subtracted as background. Peak curve fitting was performed with Gauss-Lorentz sum function.

Results: The FTIR spectrum of the SNSA (b-130) specimen in watery solution is shown on FIG. 29. It comprises the main infrared absorption bands in the range 1300 and 800 $cm^{-1}$ as predicted for the dissolved SNSA with the structure disclosed by the instant invention.

The most dominant band at 1130 $cm^{-1}$ is assigned to the asymmetric stretching vibrations of the inner Si—O—Si bonds corresponding to the $Q^4$ type Si atoms as described by the invention. This absorption band is a superimposition of several individual peaks. The fitting of this broad band at 1130 $cm^{-1}$ with peaks at 1192 $cm^{-1}$, 1160 $cm^{-1}$ and 1119 $cm^{-1}$ was found satisfactory.

The intense peak at 1017 $cm^{-1}$ is located between the asymmetric stretching vibration TO3 at 1087 $cm^{-1}$ and the stretching vibration of the silanol group at 942 $cm^{-1}$ In silica sols with colloidal silica particles with ☐>5 nm the intensity of this band is lower and the peak is shifted to 1060 $cm^{-1}$ which is not identified in the spectrum of SNSA. Similarly absent is the IR absorption band at 1060 $cm^{-1}$ corresponding to Si—O—Si bonds on the external surface of solid silica particles.

Further arguments supporting the structure of the inventive SNSA molecules with high density of free Si—OH groups on the surface of the spheroid is the frequency of further IR bands such as the position at 880 $cm^{-1}$. The Fourier-Transform Infrared spectra of the sub-nano-silicic acids according to the invention are in agreement with their structure here disclosed. This include the assumed equilibrated ratio between $Q^4:Q^3$ and $Q^2$ type Si atoms and the high density of the free silanol groups on the external shell of the spheroidal molecule.

Example 22

Stability of SNSA at Long Time Storage

Stability of the inventive silicic acid (SNSA) samples was investigated at long time storage by experimental determination of their inhibitory potential on the Na,K-ATPase enzyme isolated from rabbit medulla. The test method is described in detail by the Example 11 of the instant patent application.

Three different SNSA preparations have been investigated for their stability at 8 month storage at room temperature and compared with the inhibitory potential of a standard Ouabain.$8H_2O$ (Sigma-Munich) sample freshly prepared for each measurement set. The mean $IC_{50}$ value the cardiac steroid Ouabain is at 0.72 µg/ml corresponding to the $1/IC_{50}=1.36$ or 1 $µmol.L^{-1}$ of this standard.

1) SNSA (b 109), conc. 23.8 mg/ml, pH=2.0-2.1
2) SNSA (b 111), conc. 24.2 mg/ml, pH=8.9-9.1
3) SNSA (b 102) deposed 4.8% m/m on Sorbitol (Sigma) as solid support.

The inhibitory potential of the samples is expressed for each measurement set as IC50 as defined by Example 11. In case of the SNSA deposed on solid support the IC50 is calculated for the actual SNSA content of the solution.

The diagram in FIG. 30 shows the results of the study. The stability of the inventive Sub-nano-silicic acid at slight acidic pH=2.0 is remarkable high. A significant decrease of the activity is observed only after 4-5 months storage. Similar conclusions are valid for the stability of the inventive SNSA at basic value at pH=9.0 or higher. It is worth to note the practically unaltered stability of the inventive SNSA substance deposed on solid support according to the invention.

Example 23

SNSA Reduces Blood Glucose in Diabetes Model STZ

The investigation aimed to establish whether the oral application of the inventive Sub-nano-silic-acid is able to reduce the elevated blood glucose level in streptozotocin (STZ) induced diabetes rat model. The putative effect of SNSA should was compared with that of the Vanadate L-Glutamine complex with previously confirmed efficacy in this diabetes model.

Twenty non-diabetic male Wistar rats (185-205 g) were treated by single intravenous injection of Streptozotocin in 50 mg/kg body weight dose for each animal.

On day 5 after the administration 16 of the STZ treated rats manifested elevated blood glucose levels (>250 mg/dL) corresponding to their diabetes status.

The rats with STZ induced diabetes were divided into four groups according to the applied therapeutics: SNSA group (6 rats), Vanadate group (3 rats) Troglitazone group (4 rats), Control group (3 rats). The daily applied doses were 12.5 mg/kg b.w. SNSA, 20 mg/mg b.w Trogiltazone and 25 mg/kg b.w. Vanadate-bis-L-Glutamine complex [$VO_3$ $(Glm)_2$]. The control group animals received the same volume of the vehicle. One animal of the SNSA group was below the "diabetes" level and excluded from the study.

Results: the mean glucose level values assayed after 12; 24 and 48 hours after the therapy onset are shown in FIG. 31.

The experiment on STZ induced diabetes model revealed that the inventive silicic acids SNSA provides a considerable lowering of the blood glucose level in the diabetes animals. It is worth to note that this anti-diabetes effect was provided significantly lower doses of SNSA as of the vanadate complex and the diabetes drug troglitazone used as comparator. The two order of magnitude lower toxicity of SNSA in comparison with vanadates is a further important argument to favour the application of the inventive biological active silicic acid in the diabetes therapy.

Possible mechanism of SNSA may be as shown in FIG. 32 the insulin-mimetic action by interaction with the Insulin receptor (IR). This may involve the inhibition of the phosphotyrosine phosphatase PTP1B coupled to the insulin receptor. This phosphatase reduces the degree of phosphorylation of the insulin receptor which decreases insulin signalling and insulin sensitivity.

Example 24

Application of SNSA to Treat Duodenal Ulcers

SNSA according to the invention is a very potent inhibitor of the Proton Pump also described as H/K-ATPase. This pharmacologic action is of practical importance in treating gastric hyperacidity one of the main causes of gastric/duodenal ulceration.

24 Female Wistar rats with an initial body weight of 200±10 g with ad libitum access to standard lab-chow and tap water were used. Three injections of aqueous 10% cysteamine-hydrochloride (Sigma-Aldrich) solution are given subcutaneously at 3 to 4-hour intervals in a single day. This administration mode assured a high ulcerogenic response and low mortality.

The animals were treated in groups as follows:
SNSA-5 group, 8 rats received every 3 hours p.o. 5 mg SNSA/0.5 ml water
SNSA-3 group, 8 rats received every 3 hours p.o. 3 mg SNSA/0.5 ml water
Control group, 8 rats received only the vehicle

| GROUP | Total animals | Developed ulcer | % |
|---|---|---|---|
| SNSA 5 | 8 | 4 | 50.0% |
| SNSA 3 | 8 | 5 | 62.5% |
| CONTROL | 8 | 7 | 87.5% |

In conclusion the SNSA treated animals had a significantly lower incidence to develop duodenal ulceration as the control group animals. The anatomo-pathologic investigation evidenced the very efficient protective role of the inventive silicic acid products SNSA by reduction of the gastric hyperacidity.

Example 25

Effect of SNSA on Branching and Spreading of Cancer Cells

MDA-MB-435 cells were cultured in Dulbecco's modified Eagle's high glucose medium obtained from Invitrogen (Bremen DE) at 37° C. in an environment of 95% air and 5% $CO_2$. For the migration and invasion assays serum-free cell culture media with final concentration of $1·10^5$ cells/ml were used. Culture media containing 10% fetal bovine serum (FBS) as chemoattractant, was added to all the wells of the 24-well plate.

A FluorBlok insert with a 0.8 mm pore size porous membrane (BD Bioscience) was transferred to each well containing the chemo-attractant, creating an upper and lower chamber. Cells ($5·10^4$) were placed into the upper chamber and incubated for 24 h at 37° C. Invasion studies were completed as stated above over a 48 h period using Fluor-Blok membranes pre-coated with 62.5 mg/ml of Matrigel (Bioscience, Canaan, Conn.) diluted in cell culture media. Insert membranes were pre-coated and allowed to set for 1 h in a tissue culture incubator before the addition of the cells and media.

To assess the extent of cell migration or invasion, cells adhering to both the top and the bottom of the membrane were rinsed with Hank's balanced salt solution (HBSS/Invitrogen). Cells were fixed with HemaColor solution 1 fixative. Random digital images (10 from the top and 10 from the bottom of the filter) were acquired using Leica microscope equipped with a digital CCD camera (Hamamatsu Photonics, Japan).

The microscope image of the investigated segments (FIG. 33) evidences the branching of the non treated breast cancer cells. Inhibition or prevention of the branching of cells is evident on the slides with SNSA treated cells. The tendency of branching is already present at the lower dose SNSA but is absent at higher dose of the inventive biological active silicic acid.

Example 26

Application of the Inventive SNSA in the Osteoporosis Model

The goal of the present study was to investigate the inventive sub-nano-silicic acid SNSA in bone health application by the osteoporosis model in ovariectomized (Ovx) rats. The Ovx rat model is attested to be appropriate for evaluation of agents to prevent bone loss in postmenopausal women. Aim of the investigation was to assess the effect of daily administered SNSA on bone building of the animals in comparison with control groups.

Eighteen Wistar rats, 6 months old were either ovariectomized or sham-operated according to standard surgical procedure. The surgery of sham-operation is the same as by ovariectomized animals, however the ovary is not cut off. Since sham-operated rats suffer pain and stress as animals in the control group the comparison of the two groups is more significant.

The study was conducted in 18 animals randomly assigned in three groups: two groups (Ovx) with ovariectomized rats and one group of sham operated animals.

Ovx-SNS group animals (8 rats) received supplementary to their standard feed & water supply daily doses of either 5.0 mg/kg b.w. SNSA per oral.

Ovx-Control group with 5 ovariectomized rats received standard feed and water supply for the whole duration of the study, Sham-group rats (5 animals) which are sham-operated i.e. they ovary was not removed. The study duration was of 12 weeks started 10 days after the operation. All animals were sacrificed at the end of the treatment. Blood chemistry, body weight and organ weight were measured and compared among the groups. Bone mineral densities (BMD) of the lumbar spine at L2-L5 were measured by dual-energy X-ray absorptiometry (DEXA) using the osteodensitometer ODR-1000/W (Hologic Inc.) After removing soft tissue, the un-decalcified bone sample of the third lumbar vertebral body was investigated.

Results: Our data revealed that the plasma 17β-estradiol levels in the Ovx group at the end of the experiment were significantly lower than in the sham group. Ovariectomized rats showed increased body weight compared to sham group.

SNSA treated animals manifested an increased bone formation characterized by enhanced osteoid surface (OS/BS) compared with that of the control group. The SNSA treated animals showed no significant decrease of the trabecular bone volume (BV/TV) as observed in the sham-operated group. In comparison with the deteriorated bone formation parameters of the OVX-control group the SNSA treated animals have similar values with the sham groups.

Administration of SNSA in daily doses of 5 mg/animal counterbalanced efficiently the bone deterioration produced by ovariectomy. In conclusion the inventive sub-nano-silicic acid is a useful drug to prevent and treat efficiently osteoporosis with significant contribution to bone health.

Example 27

Wound Healing Efficacy of SNSA in Sulphur Mustard Model

Efficacy of the inventive sub-nano-silicic acid in topical formulation to treat severe dermal damages produced by aggressive chemicals was tested in a standard animal model. The blistering chemical warfare agent sulfur mustard with chemical name: bis-(2-chloroethyl)sulphide, abbreviation (HD) was applied as test substance on weanling pigs.

Two female weanling pigs were exposed to liquid HD for 2 h, generating six 3-4 cm diameter full-thickness dermal lesions on the ventral surface. The HD treatment produced with a delayed onset of 2 to 6 hours an intense erythema which was transformed in a blister. The lesions were noted A1-A6 on the first and B1-B6 on the second animal. The topical treatments with the investigational products started 24 h after HD application, with 3-time daily application in doses as specified below:

A1-A3 treated with 0.5 ml SNSA (1.5 mg/ml) in topical composition

A4-A5 treated with 0.5 ml vehicle (placebo control)

B1-B3 with 0.5 ml SNSA (2.5 mg/ml) in topical composition

B4-B6 mafenide acetate (50 mg/ml) in buffer

The animals were under clinical observation for 8 weeks measuring the diameter, pathologic evolution and healing of the blisters. Clinical pathology findings and the urinary excretion of the major HD metabolite (thiodiglycol, TDG) was performed in the first 12 days by urinalysis coupled with gas chromatography/mass spectrometry assay. Reepithelisation and regain of the barrier function for transepidermal water loss (TEWL) was monitored.

Results: The transepidermal water lost was severely disrupted on day 3 or 4 after exposure to liquid HD without clear cut correlation with the applied medication. Full reepithelialization of the dermal injuries was observed 36 to 46 days after exposure. The time of the dermal recovery was favorably influenced by the application of the inventive sub-nano-silicic acid SNSA with best results by its higher (2.5 mg) dose application.

Application of the inventive SNSA in the daily dose of 2.5 mg provided a 23% shorter period of reepitelization (35.7 days instead of 46.3). Significant 22.5% shortening of the regain of the TEWL barrier function was provided by the application of the inventive SNSA in 41.3 days in comparison to 53.3 days recovery of the placebo treated control wounds.

The inventive SNSA in 2.5 mg dose was already superior to the standard treatment with 5% mafenide acetate. This is a remarkable technical progress provided by the inventive SNSA in comparison to a prior art product applied in 20 fold higher doses (50 mg vs. 2.5 mg).

| | CONTROL | SNSA (1.5 mg) | SNSA (2.5 mg) | Mafenide (50 mg) |
|---|---|---|---|---|
| Blister formation | 3 hours | 3 hours | 3 hours | 3 hours |
| Disrupted TEWL | day 3 | day 3 | day 4 | day 4 |
| Re-epitelization* | 46.3 days | 40.3 days | 35.7 days | 38.0 days |
| Recovered TE barrier* | 53.3 days | 47.0 days | 41.3 days | 44.3 days |

*mean value of three blisters

In conclusion the inventive sub-nano-silicic acid provides an efficient recovery of the damaged skin area with significantly shorter time of reepitelization and recovery of the full functionality.

Example 28

Use of a Topical Composition of Sub-Nano-Silicic Acid to Treat Sunburn

The inventive sub-nano-silicic acid was tested by topical application to treat sunburn caused by prolonged, unprotected exposure to sun, particularly to ultraviolet radiation of type UV-A (300-400 nm) and UV-B (260-290 nm).

A young man (23y) and woman (21y) both with skin of Type II in Fitzpatrick classification displayed (involuntary) sunburn grade I of their thoracic skin region. Cause of the sunburn was their unprotected ca. 1.5 hour exposure to midday sun, summer time in subalpine region of Bavaria, altitude of 950 m.

Their skin had turned deep-red and aching, and he could not stand the contact of clothes over the burnt zone.

The efficacy of the inventive sub-nano-silicic-acid (SNSA) in sunburn was tested by a topical composition containing 0.5% m/v SNSA, 1.5% m/v sodium bicarbonate and 15% m/v glycerin and the balance distilled water. The topical formulation with SNSA according to the invention was sprayed in a thin uniform layer over 75% of the reddening area while 25% surface remained untreated.

The first application was 2.5 hours after the sun exposure. The applied dose was of 2.5 mg SNSA/100 cm² skin surface area. An immediate pain relief was manifested and the test persons related the amelioration of the burning sensation. The application of the SNSA containing composition was repeated 3 times in the first day and twice in the following day. The skin temperature was assigned by digital contact thermometer with precision of ±0.15° C., pain score by a visual analogue scale (VAN) and the color of skin by comparison with a standard color scale used in pharmaceutical analysis for colorimetric classification of solutions.

After the first application of SNSA the skin temperature was reduced with 1.8-2.4° C. The summed pain, color and temperature measurement's score of the NSA treated skin area was compared with the summed parameters of the non-treated skin area in the thoracic region.

According to the pain, temperature and color assignments the therapy with SNSA provided a 62-76% amelioration of the treated skin region in comparison with the untreated skin area as control.

The invention claimed is:

1. Substances of the general formula (I)

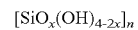

wherein the Si atoms are $Q^1$, $Q^2$, $Q^3$ and $Q^4$ type Si atoms and n represents an integer between 12 and 2000 and X represents a number between 1.2 and 1.8 and wherein the substances have a spherical or almost spherical form and a diameter in the range of 0.3 nm to 5.0 nm and consist of an inner core and an outer shell and wherein more than 75% of the $Q^4$ type Si atoms are contained in the inner core and more than 75% of $Q^3$ and $Q^2$ and $Q^1$ type Si atoms are contained in the outer shell.

2. Substances according to claim 1, wherein the substances have a diameter in the range of 0.6 nm to 3.0 nm.

3. Substances according to claim 1 having a molar mass in the range of 0.7-140 kDa.

4. Substances according to claim 3 having a molar mass in the range of 1.4-20 kDa.

5. Substances according to claim 1, wherein the Si—OH groups attached to
the Si atoms of type $Q^3$, $Q^2$ and $Q^1$ of the outer shell are densely and evenly distributed.

6. Substances according to claim 1, wherein n is an integer within the range 20 and 300.

7. Substances according to claim 1, wherein n represents an integer between 14 and 1500, and wherein the substances have a range of distribution around a preselected n value, wherein the maximum range of distribution is from n−0.15n to n+0.15n.

8. Substances according to claim 1, wherein the numerical ratio between the sum of the $Q^3$ and $Q^2$ type Si atoms and the $Q^4$ type Si atoms is between 1.5 and 2.5.

9. Substances according to claim 1 which are stabilized by deposition on a neutral, polyhydroxylated carrier in solid or non-volatile liquid form or by deposition directly on a pharmaceutically accepted carrier of a solid or non-volatile liquid form.

10. Substance according to claim 1 having a long time stability with maintenance of >85% of its biological activity for at least 3 months of storage at room temperature.

11. A method for modulating the activity of Na,K-ATPase, Ca-ATPase, and H/K-ATPase comprising contacting them with an effective dose of the compound of claim 1.

12. A method for the treatment of diabetes comprising administering an effective dose of the compound of claim 1 to a subject in need thereof.

13. Pharmaceutical formulation comprising at least one substance of claim 1 together with at least one pharmaceutically acceptable carrier, adjuvant and/or solvent.

14. Substances according to claim 1, wherein X=1.5.

* * * * *